US006972179B2

(12) United States Patent
Friedman et al.

(10) Patent No.: US 6,972,179 B2
(45) Date of Patent: Dec. 6, 2005

(54) RRP SEQUENCES AND KNOCKOUT MICE AND USES THEREOF

(75) Inventors: Lori Friedman, San Francisco, CA (US); Marcia Belvin, Albany, CA (US); Jeffrey S. Larson, Burlingame, CA (US); Helen Francis-Lang, San Francisco, CA (US); Gregory D. Plowman, San Carlos, CA (US)

(73) Assignee: Exelixis, Inc., South San Francisco, CA (US)

( * ) Notice: Subject to any disclaimer, the term of this patent is extended or adjusted under 35 U.S.C. 154(b) by 317 days.

(21) Appl. No.: 10/056,790

(22) Filed: Jan. 23, 2002

(65) Prior Publication Data

US 2003/0165497 A1 Sep. 4, 2003

Related U.S. Application Data

(63) Continuation-in-part of application No. 09/908,419, filed on Jul. 18, 2001.
(60) Provisional application No. 60/219,289, filed on Jul. 19, 2000, provisional application No. 60/277,487, filed on Mar. 21, 2001, provisional application No. 60/277,471, filed on Mar. 21, 2001, provisional application No. 60/304,863, filed on Jul. 12, 2001, provisional application No. 60/296,076, filed on Jun. 5, 2001, provisional application No. 60/305,017, filed on Jul. 12, 2001, provisional application No. 60/328,605, filed on Oct. 10, 2001, and provisional application No. 60/328,491, filed on Oct. 10, 2001.

(51) Int. Cl.[7] .................. G01N 33/53; G01N 33/48; C12Q 1/70; A01N 61/00

(52) U.S. Cl. .................. 435/7.1; 435/5; 436/64; 424/130.1; 514/2

(58) Field of Search .................. 436/64; 435/3; 424/130.1; 514/2; 536/24.5

(56) References Cited

FOREIGN PATENT DOCUMENTS

WO    WO 02/05843    1/2002

OTHER PUBLICATIONS

Barg S et al (Neuron. Jan. 17, 2002;33(2):287–99).*
Savino TM et al (J Cell Sci. Jun. 1999;112 ( Pt 12):1889–900).*
Szakmary et al (PNAS USA 1996; 93:1607–1612).*
Database EMBL 'Online!, Accession No. Q9NX52, Oct. 1, 2000, K. Watanabe et al.: "NEDO human cDNA sequencing project" XP002192453.
Golembo, M., et al., "The Drosophila embryonic midline is the site of Spitz processing, and induces activation of the EGF receptor in the ventral ectoderm", Development, 1996, 122:3363–3370, The Company of Biologists Limited, Great Britain.

Wasserman, J.D., et al., "A family of rhomboid–like genes: Drosophilia rhomboid–1 and roughoid/rhomboid–3 cooperate to activate EFG receptor signaling", Genes & Development, 2000, 14:1651–1653, Cold Spring Harbor Laboratory Press.
Schweitzer, R., et al., "Secreted Spitz triggers the DER signaling pathway and is a limiting component in embryonic ventral ectoderm determination", Genes & Development, 1995, 9:1518–1529, Cold Spring Harbor Laboratory Press.
Duffy, J.B., et al., "Recent advances in understanding signal transduction pathways in worms and flies" Current Opinion in Cell Biology, 1996, 8:231–238, Current Biology Publishing.
Pascall, J.C., et al., "Characterization of a mammalian cDNA encoding a protein with high sequence similarity to the Drosophila regulatory protein Rhomboid" FEBS Letters, 1998, 429:337–340, Federation of European Biochemical Societies.
Pascall,J.C., "Homo sapiens mRNA for rhomboid–related protein" Genbank GI No. 3287190, Jun. 30, 1998.
NIH–MGC, "602365464F1 NIH_MGC_90 Homo sapiens cDNA clone IMAGE:4473855 5',mRNA sequence" Genbank GI No. 12762689, Feb. 13, 2001.
NIH–MGC, "602251313F1 NIH_MGC_84 Homo sapiens cDNA clone IMAGE:4343882 5', mRNA sequence" Genbank GI No. 12096415, Jan. 12, 2001.
NCI–CGAP, "xv57g07.x1 NCI_CGAP_Lu28 Homo sapiens cDNA clone IMAGE:2817276 3' similar to SW:Rhom_Drome P20350 Rhomboid Protein ;, mRNA sequence" Genbank GI No. 6657080, Jan. 3, 2000.
Dias Neto,E., et al., "QV0–CT0225–230300–169–e09 CT0225 Homo sapiens cDNA, mRNA sequence" Genbank GI No. 7947756, May 19, 2000.
NCI–CGAP, "on76e02.s1 Soares_NFL_T_GBC_S1 Homo sapiens cDNA clone" Genbank GI No. 3117010, Jun. 23, 1998.
NIH–MGC, "601310502F1 NIH_MGC_44 Homo sapiens cDNA clone IMAGE:3631824 5', mRNA sequence" Genbank GI No. 9339870, Jul. 21, 2000.
NCI–CGAP, "hd76f05.x1 NCI_CGAP_Lu28 Homo sapiens cDNA clone IMAGE:2915457 3' similar to TR:O75783 O75783 Rhomboid–Related Protein. ;, mRNA sequence" Genbank GI No. 7152496, Mar. 3, 2000.
Dias Neto,E., et al., "RC0–EN0025–200600–031–d10 EN0025 Homo sapiens cDNA, mRNA sequence" Genbank GI No. 11317512, Nov. 22, 2000.

(Continued)

*Primary Examiner*—G. Nickol
*Assistant Examiner*—C. Yaen

(57) ABSTRACT

RRP genes are identified as modulators of the p53 or p21 pathway, and thus are therapeutic targets for disorders associated with defective p53 or p21 function. Methods for identifying modulators of p53 or p21, comprising screening for agents that modulate the activity of RRP are provided. Modulating agents identified using the methods of the invention can be used to specifically inhibit growth of tumor cells that overexpress an RRP protein. mRRP1 knockout mice are also provided.

5 Claims, 4 Drawing Sheets

OTHER PUBLICATIONS

Dias Neto,E., et al., "RC0–EN0025–200600–031–e08 EN0025 Homo sapiens cDNA, mRNA sequence" Genbank GI No. 11317513, Nov. 22, 2000.

Dias Neto,E., et al., "RC0–EN0025–200600–031–c01 EN0025 Homo sapiens cDNA, mRNA sequence" Genbank GI No. 11317511, Nov. 22, 2000.

NIH–MGC, "601463932F1 NIH_MGC_67 Homo sapiens cDNA clone IMAGE:3867487 5', mRNA sequence" Genbank GI No. 10199673, Oct. 20, 2000.

Adams,M.D., "EST59487 Infant brain Homo sapiens cDNA 5' end, mRNA sequence" Genbank GI No. 2003992, Apr. 21, 1997.

Pascall,J.C., "rhomboid–related protein" Genbank GI No. 3287191, Jun. 30, 1998.

Watanabe,K., et al., "hypothetical protein FLJ20435" Genbank GI No. 8923409, Feb. 10, 2002.

NCBI Annotation Project, "hairy (Drosophila)–homolog" Genbank GI No. 12729522, Feb. 9, 2001.

NCBI Annotation Project, "hypothetical protein FLJ20435 " Genbank GI No. 11421817, Nov. 16, 2000.

Pellegrini,L., et al., "Homo sapiens presenilins associated rhomboid–like protein (PARL) mRNA, complete cds" Genbank GI No. 11066249, Jan. 5, 2001.

Kawabata,A., et al., "Homo sapiens hypothetical protein FLJ22357 similar to epidermal growth factor receptor–related protein (FLJ22357), mRNA" Genbank GI No. 11967982, Dec. 19, 2000.

Kawabata,A., et al., "Homo sapiens cDNA: FLJ22341 fis, clone HRC06032." Genbank GI No. 10438685, Sep. 29, 2000.

Xiao,H., et al., "Homo sapiens NPD007 protein (NPD007), mRNA." Genbank GI No. 10190733, Dec. 10, 2001.

Dunham I, et al., "Homo sapiens chromosome 22 open reading frame 3 (C22orf3), mRNA" Genbank GI No. 11072100, Jun. 22, 2001.

Pellegrini,L., et al., "presenilins associated rhomboid–like protein [Homo sapiens]." Genbank GI No. 11066250, Jan. 5, 2001.

Kawabata,A., et al., "hypothetical protein FLJ22357 similar to epidermal growth factorreceptor–related protein [Homo sapiens]." Genbank GI No. 11967983, Dec. 19, 2000.

Kawabata,A., et al., "unnamed protein product [Homo sapiens]." Genbank GI No. 10438686, Sep. 29, 2000.

Xiao,H., et al., "NPD007 protein [Homo sapiens]." Genbank GI No. 10190734, Dec. 10, 2001.

Dunham I, et al., "chromosome 22 open reading frame 3; hypothetical protein [Homo sapiens]." Genbank GI No. 11072101, Jun. 22, 2001.

* cited by examiner

FIG.1 pEasyfloxFRTGK12 mRRP1

FIG.2 mRRP1 gene targeting

FIG.4
RRP1 target allele (HR)
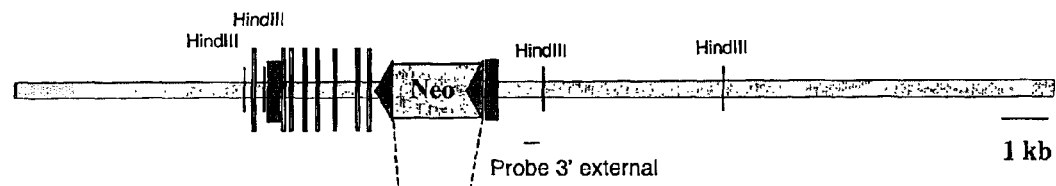
Probe 3' external
HindIII    HR: 5.8 kb, WT: 4.3 kb
RRP1 target allele FLP deletion
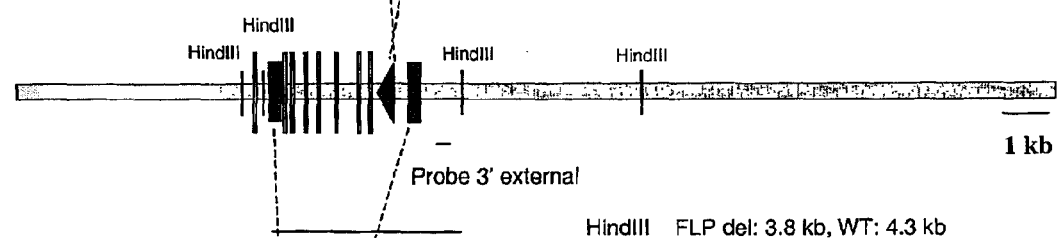
Probe 3' external
HindIII    FLP del: 3.8 kb, WT: 4.3 kb
RRP1 target allele Cre deletion
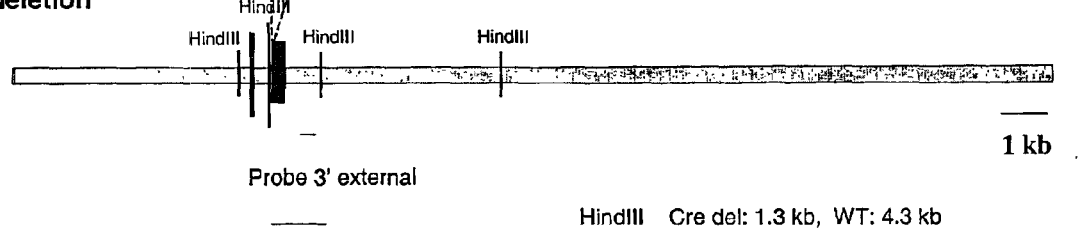
Probe 3' external
HindIII    Cre del: 1.3 kb, WT: 4.3 kb

SEQUENCE LISTING

<160> NUMBER OF SEQ ID NOS: 70

<210> SEQ ID NO 1
<211> LENGTH: 1559
<212> TYPE: DNA
<213> ORGANISM: Homo sapiens

<400> SEQUENCE: 1

```
cttggacctt ggccctcgct ttccaggatg ggtagggtgg aagacggggg aacaactgag      60
gagctggagg actgggaccc aggcaccagt gccctgccag ctcctgggat caagcagggt     120
cccagggaac agacaggcac ggggcccctg tcccaaaagt gctgggagcc tgagcctgat     180
gctcccagcc agcctggccc agccctttgg tccagggtc gggcccgcac tcaggccttg     240
gctggcggct cctcactgca gcagctggac cccgagaaca caggcttcat cggtgcggac     300
accttcactg gcctggtgca cagccatgag ctgcccctgg acccggccaa gctggacatg     360
ctggtggccc tggctcagag caacgagcag ggccaggtct gctaccagga gctggtggac     420
ctgatcagca gcaagcgctc cagcagtttc aagcgggcca ttgctaacgg acagcgggca     480
ctgccccggg acgggccgct ggatgagcca ggcctaggtg tctacaagcg gtttgtgcgt     540
tacgtggcct acgagatcct gccttgtgag gtggaccgcc gctggtactt ctaccgtcac     600
cgcagctgcc caccccccgt gttcatggcc tcggtcactc ttgcccagat catcgtgttc     660
ctgtgttacg gggcccgcct caacaagtgg gtgctgcaga cctaccaccc cgagtacatg     720
aagagccccc ttgtgtacca ccccgggcac cgtgcccgcg cctggcgctt cctcacctac     780
atgttcatgc acgttgggct ggagcagctg gggttcaacg ccctcctgca gctgatgatc     840
ggggtgcccc tggagatggt gcacggcctg ctccgcatca gcctgctcta cctggcaggc     900
gtgctggcag gctccctaac cgtctccatc accgacatgc gggcccggt ggtgggaggc     960 tccggcgggg tctacgccct gtgctcggca cacctggcca acgttgtcat gaactgggct    1020
gggatgagat gtccctacaa gttgctgagg atggtgctgg ccttggtgtg catgagctcc    1080
gaggtgggcc gggccgtgtg gctgcgcttc tccccgccgc tgcccgcctc gggcccacag    1140
cccagcttca tggcgcacct ggcaggcgcg gtggtggggg tgagcatggg cctgaccatc    1200
ctgcggagct acgaggagcg cctgcgggac cagtgcggct ggtgggtggt gctgctggcc    1260
tacggcacct tcctgctctt cgccgtcttc tggaacgtct tcgcctacga cctgctgggc    1320
```

-continued

```
gcccacatcc ccccaccgcc ctgaccggct acctgaggct gcacaggcca gggctcgggc      1380
atgtggtggc cgcccaccag gggccttcac gtctgccctt tgtgaacgga cgtctcaggg      1440
ctgctgtgcc ccttgggtgt gggtggcctc aaaggaggcc ctgtcccagc cacccacccc      1500
ccactcccag gacttgcggt ctgagccttt ttggataatt aataaatatt ttacacagc       1559
```

<210> SEQ ID NO 2
<211> LENGTH: 438
<212> TYPE: PRT
<213> ORGANISM: Homo sapiens

<400> SEQUENCE: 2

```
Met Gly Arg Val Glu Asp Gly Gly Thr Thr Glu Glu Leu Glu Asp Trp
1               5                   10                  15

Asp Pro Gly Thr Ser Ala Leu Pro Ala Pro Gly Ile Lys Gln Gly Pro
            20                  25                  30

Arg Glu Gln Thr Gly Thr Gly Pro Leu Ser Gln Lys Cys Trp Glu Pro
        35                  40                  45

Glu Pro Asp Ala Pro Ser Gln Pro Gly Pro Ala Leu Trp Ser Arg Gly
    50                  55                  60

Arg Ala Arg Thr Gln Ala Leu Ala Gly Ser Ser Leu Gln Gln Leu
65                  70                  75                  80

Asp Pro Glu Asn Thr Gly Phe Ile Gly Ala Asp Thr Phe Thr Gly Leu
                85                  90                  95

Val His Ser His Glu Leu Pro Leu Asp Pro Ala Lys Leu Asp Met Leu
            100                 105                 110

Val Ala Leu Ala Gln Ser Asn Glu Gln Gly Gln Val Cys Tyr Gln Glu
        115                 120                 125

Leu Val Asp Leu Ile Ser Ser Lys Arg Ser Ser Phe Lys Arg Ala
    130                 135                 140

Ile Ala Asn Gly Gln Arg Ala Leu Pro Arg Asp Gly Pro Leu Asp Glu
145                 150                 155                 160

Pro Gly Leu Gly Val Tyr Lys Arg Phe Val Arg Tyr Val Ala Tyr Glu
                165                 170                 175

Ile Leu Pro Cys Glu Val Asp Arg Arg Trp Tyr Phe Tyr Arg His Arg
            180                 185                 190

Ser Cys Pro Pro Pro Val Phe Met Ala Ser Val Thr Leu Ala Gln Ile
        195                 200                 205

Ile Val Phe Leu Cys Tyr Gly Ala Arg Leu Asn Lys Trp Val Leu Gln
    210                 215                 220

Thr Tyr His Pro Glu Tyr Met Lys Ser Pro Leu Val Tyr His Pro Gly
225                 230                 235                 240

His Arg Ala Arg Ala Trp Arg Phe Leu Thr Tyr Met Phe Met His Val
                245                 250                 255

Gly Leu Glu Gln Leu Gly Phe Asn Ala Leu Leu Gln Leu Met Ile Gly
            260                 265                 270

Val Pro Leu Glu Met Val His Gly Leu Leu Arg Ile Ser Leu Leu Tyr
        275                 280                 285

Leu Ala Gly Val Leu Ala Gly Ser Leu Thr Val Ser Ile Thr Asp Met
    290                 295                 300

Arg Ala Pro Val Val Gly Gly Ser Gly Gly Val Tyr Ala Leu Cys Ser
305                 310                 315                 320

Ala His Leu Ala Asn Val Val Met Asn Trp Ala Gly Met Arg Cys Pro
                325                 330                 335
```

```
Tyr Lys Leu Leu Arg Met Val Leu Ala Leu Val Cys Met Ser Ser Glu
            340                 345                 350

Val Gly Arg Ala Val Trp Leu Arg Phe Ser Pro Pro Leu Pro Ala Ser
        355                 360                 365

Gly Pro Gln Pro Ser Phe Met Ala His Leu Ala Gly Ala Val Val Gly
    370                 375                 380

Val Ser Met Gly Leu Thr Ile Leu Arg Ser Tyr Glu Glu Arg Leu Arg
385                 390                 395                 400

Asp Gln Cys Gly Trp Trp Val Val Leu Leu Ala Tyr Gly Thr Phe Leu
                405                 410                 415

Leu Phe Ala Val Phe Trp Asn Val Phe Ala Tyr Asp Leu Leu Gly Ala
                420                 425                 430

His Ile Pro Pro Pro Pro
            435
```

<210> SEQ ID NO 3
<211> LENGTH: 1224
<212> TYPE: DNA
<213> ORGANISM: Homo sapiens

<400> SEQUENCE: 3

```
gggccattta ggaggtttag atcatttga tcatcttcag ctgtcttctc ttcacataca     60
ggaaaggcct tggaaagcag tcgttgcgcc agacagccca gggaagagcg gcagcctgag    120
gacctagggc cacctgctgt tccctgggat tcatgtcctt ctggggagga gggaggaccc    180
aggacaatgg ctgctgttca tgatctggag atggagagca tgaatctgaa tatggggaga    240
gagatgaaag aagagctgga ggaagaggag aaaatgagag aggatggggg aggtaaagat    300
cgggccaaga gtaaaaaggt ccacaggatt gtctcaaaat ggatgctgcc cgaaaagtcc    360
cgaggaacat acttggagag agctaactgc ttcccgcctc ccgtgttcat catctccatc    420
agcctggccg agctggcagt gtttatttac tatgctgtgt ggaagcctca gaaacagtgg    480
atcacgttgg acacaggcat cttggagagt ccctttatct acagtcctga agagggag     540
gaagcctgga ggtttatctc atacatgctg gtacatgctg gagttcagca catcttgggg    600
aatctttgta tgcagcttgt tttgggtatt cccttggaaa tggtccacaa aggcctccgt    660
gtggggctgg tgtacctggc aggagtgatt gcagggtccc ttgccagctc catctttgac    720
ccactcagat atcttgtggg agcttcagga ggagtctatg ctctgatggg aggctatttt    780
atgaatgttc tggtgaattt tcaagaaatg attcctgcct ttggaatttt cagactgctg    840
atcatcatcc tgataattgt gttggacatg ggatttgctc tctatagaag gttctttgtt    900
cctgaagatg ggtctccggt gtcttttgca gctcacattg caggtggatt tgctggaatg    960
tccattggct acacggtgtt tagctgcttt gataaagcac tgctgaaaga tccaaggttt   1020
tggatagcaa ttgctgcata tttagcttgt gtcttatttg ctgtgttttt caacattttc   1080
ctatctccag caaactgacc tgcccctatt gtaagtcaat taataaaaag agccatctgg   1140
aggaaataaa aaaaaaagga agactctatg aagaaacaga gaagtctcag aaaaggctaa   1200
caatttaga tagagaacaa aggg                                          1224
```

<210> SEQ ID NO 4
<211> LENGTH: 303
<212> TYPE: PRT
<213> ORGANISM: Homo sapiens

<400> SEQUENCE: 4

-continued

```
Met Ala Ala Val His Asp Leu Glu Met Glu Ser Met Asn Leu Asn Met
  1               5                  10                  15

Gly Arg Glu Met Lys Glu Leu Glu Glu Glu Lys Met Arg Glu
              20                  25                  30

Asp Gly Gly Gly Lys Asp Arg Ala Lys Ser Lys Val His Arg Ile
              35                  40                  45

Val Ser Lys Trp Met Leu Pro Glu Lys Ser Arg Gly Thr Tyr Leu Glu
 50                          55                  60

Arg Ala Asn Cys Phe Pro Pro Val Phe Ile Ser Ile Ser Leu
 65              70              75                  80

Ala Glu Leu Ala Val Phe Ile Tyr Tyr Ala Val Trp Lys Pro Gln Lys
                  85                  90                  95

Gln Trp Ile Thr Leu Asp Thr Gly Ile Leu Glu Ser Pro Phe Ile Tyr
                 100                 105                 110

Ser Pro Glu Lys Arg Glu Ala Trp Arg Phe Ile Ser Tyr Met Leu
                 115                 120                 125

Val His Ala Gly Val Gln His Ile Leu Gly Asn Leu Cys Met Gln Leu
    130                 135                 140

Val Leu Gly Ile Pro Leu Glu Met Val His Lys Gly Leu Arg Val Gly
145                 150                 155                 160

Leu Val Tyr Leu Ala Gly Val Ile Ala Gly Ser Leu Ala Ser Ser Ile
                 165                 170                 175

Phe Asp Pro Leu Arg Tyr Leu Val Gly Ala Ser Gly Val Tyr Ala
                 180                 185                 190

Leu Met Gly Gly Tyr Phe Met Asn Val Leu Val Asn Phe Gln Glu Met
                 195                 200                 205

Ile Pro Ala Phe Gly Ile Phe Arg Leu Leu Ile Ile Ile Leu Ile Ile
                 210                 215                 220

Val Leu Asp Met Gly Phe Ala Leu Tyr Arg Arg Phe Phe Val Pro Glu
225                 230                 235                 240

Asp Gly Ser Pro Val Ser Phe Ala Ala His Ile Ala Gly Gly Phe Ala
                 245                 250                 255

Gly Met Ser Ile Gly Tyr Thr Val Phe Ser Cys Phe Asp Lys Ala Leu
                 260                 265                 270

Leu Lys Asp Pro Arg Phe Trp Ile Ala Ile Ala Ala Tyr Leu Ala Cys
                 275                 280                 285

Val Leu Phe Ala Val Phe Phe Asn Ile Phe Leu Ser Pro Ala Asn
                 290                 295                 300
```

<210> SEQ ID NO 5
<211> LENGTH: 1376
<212> TYPE: DNA
<213> ORGANISM: Homo sapiens

<400> SEQUENCE: 5

```
ctgaactgat gaggttttca tgggaaatca gtgcctgtct gttcatctga acacccacta      60
gttattcatc caacaaatct tgattgagtg ctgataatgc caggctctgt gctaagtacc     120
ggggataagt tgtgataccg acccgcgagg cgccgcggtc caaggaggag caaaagcag     180 acagacatca gtgtgggctg gaggcccaga ggtctggaca gaacagaggg ttccgtgaga     240
acaggccatg gctgagtttg accctgggaa cacaggctac attagcacag caagttccg     300 gagtcttctg gagagccaca gctccaagct ggaccgcac aaaagggagg tcctcctggc     360
tcttgccgac agccacgcgg atgggcagat cggctaccag gattttgtca gcctagtgag     420
```

```
caacaagcgt tccaacagct tccgccaagc catcctgcag ggcaaccgca ggctaagcag    480
caaggccctg ctggaggaga aggggctgag cctctcgcag cgacttatcc gccatgtggc    540
ctatgagacc ctgccccggg aaattgaccg caagtggtac tatgacagct acacctgctg    600
cccccacccc tggttcatga tcacagtcac gctgctggag gttgcctttt tcctctacaa    660
tgggtgtca ctaggtcaat ttgtactgca ggtaactcat ccacgttact gaagaactc     720
cctggtttac cacccacagc tgcgagcaca ggtttggcgc tacctgacat acatcttcat    780
gcatgcaggg atagaacacc tgggactcaa tgtggtgctg cagctgctgg tgggggtgcc    840
cctggagatg gtgcatggag ccacccgaat tgggcttgtc tacgtggccg tgttgtggc    900
agggtccttg gcagtgtctg tggctgacat gaccgctcca gtcgtgggct cttctggagg    960
ggtgtatgct ctcgtctctg cccatctggc aacattgtc atgaactggt caggcatgaa   1020
gtgccagttc aagctgctgc ggatggctgt ggcccttatc tgtatgagca tggagtttgg   1080
gcgggccgtg tggctccgct ccacccgtc ggcctatccc ccgtgccctc acccaagctt   1140
tgtggcgcac ttgggtggcg tggccgtggg catcaccctg ggcgtggtgg tcctgaggaa   1200
ctacgagcag aggctccagg accagtcact gtggtggatt tttgtggcca tgtacaccgt   1260
cttcgtgctg ttcgctgtct tctgaacat ctttgcctac accctgctgg acttaaagct   1320
gccgcctccc ccctgagggc tggaggccca aggtcgggga ggggagggaa aagcag       1376
```

<210> SEQ ID NO 6
<211> LENGTH: 362
<212> TYPE: PRT
<213> ORGANISM: Homo sapiens

<400> SEQUENCE: 6

```
Met Ala Glu Phe Asp Pro Gly Asn Thr Gly Tyr Ile Ser Thr Gly Lys
  1               5                  10                  15

Phe Arg Ser Leu Leu Glu Ser His Ser Ser Lys Leu Asp Pro His Lys
                 20                  25                  30

Arg Glu Val Leu Leu Ala Leu Ala Asp Ser His Ala Asp Gly Gln Ile
             35                  40                  45

Gly Tyr Gln Asp Phe Val Ser Leu Val Ser Asn Lys Arg Ser Asn Ser
         50                  55                  60

Phe Arg Gln Ala Ile Leu Gln Gly Asn Arg Arg Leu Ser Ser Lys Ala
 65                  70                  75                  80

Leu Leu Glu Glu Lys Gly Leu Ser Leu Ser Gln Arg Leu Ile Arg His
                 85                  90                  95

Val Ala Tyr Glu Thr Leu Pro Arg Glu Ile Asp Arg Lys Trp Tyr Tyr
                100                 105                 110

Asp Ser Tyr Thr Cys Cys Pro Pro Trp Phe Met Ile Thr Val Thr
            115                 120                 125

Leu Leu Glu Val Ala Phe Phe Leu Tyr Asn Gly Val Ser Leu Gly Gln
        130                 135                 140

Phe Val Leu Gln Val Thr His Pro Arg Tyr Leu Lys Asn Ser Leu Val
145                 150                 155                 160

Tyr His Pro Gln Leu Arg Ala Gln Val Trp Arg Tyr Leu Thr Tyr Ile
                165                 170                 175

Phe Met His Ala Gly Ile Glu His Leu Gly Leu Asn Val Val Leu Gln
            180                 185                 190

Leu Leu Val Gly Val Pro Leu Glu Met Val His Gly Ala Thr Arg Ile
        195                 200                 205
```

Gly Leu Val Tyr Val Ala Gly Val Ala Gly Ser Leu Ala Val Ser
    210                 215                 220

Val Ala Asp Met Thr Ala Pro Val Val Gly Ser Ser Gly Gly Val Tyr
225                 230                 235                 240

Ala Leu Val Ser Ala His Leu Ala Asn Ile Val Met Asn Trp Ser Gly
                245                 250                 255

Met Lys Cys Gln Phe Lys Leu Leu Arg Met Ala Val Ala Leu Ile Cys
            260                 265                 270

Met Ser Met Glu Phe Gly Arg Ala Val Trp Leu Arg Phe His Pro Ser
        275                 280                 285

Ala Tyr Pro Pro Cys Pro His Pro Ser Phe Val Ala His Leu Gly Gly
    290                 295                 300

Val Ala Val Gly Ile Thr Leu Gly Val Val Val Leu Arg Asn Tyr Glu
305                 310                 315                 320

Gln Arg Leu Gln Asp Gln Ser Leu Trp Trp Ile Phe Val Ala Met Tyr
                325                 330                 335

Thr Val Phe Val Leu Phe Ala Val Phe Trp Asn Ile Phe Ala Tyr Thr
            340                 345                 350

Leu Leu Asp Leu Lys Leu Pro Pro Pro Pro
        355                 360

<210> SEQ ID NO 7
<211> LENGTH: 1140
<212> TYPE: DNA
<213> ORGANISM: Homo sapiens

<400> SEQUENCE: 7
atggcgtggc gaggctgggc gcagagaggc tggggctgcg ccaggcgtg gggtgcgtcg      60 gtgggcggcc gcagctgcga ggagctcact gcggtcctaa ccccgccgca gctcctcgga    120
cgcaggttta acttctttat caacaaaaa tgcggattca gaaaagcacc caggaaggtt     180
gaacctcgaa gatcagaccc aggacaagt ggtgaagcat acaagagaag tgctttgatt    240
cctcctgtgg aagaaacagt cttttatcct tctccctatc ctataaggag tctcataaaa    300 ccttttatttt ttactgttgg gtttacaggc tgtgcatttg gatcagctgc tatttggcaa   360
tatgaatcac tgaaatccag ggtccagagt tattttgatg gtataaaagc tgattggttg    420
gatagcataa gaccacaaaa agaaggagac ttcagaaagg agattaacaa gtggtggaat    480
aacctaagtg atggccagcg gactgtgaca ggtattatag ctgcaaatgt ccttgtattc    540
tgtttatgga gagtaccttc tctgcagcgg acaatgatca gatatttcac atcgaatcca    600
gcctcaaagg tcctttgttc tccaatgttg ctgtcaacat tcagtcactt ctccttattt    660
cacatggcag caaatatgta tgttttgtgg agcttctctt ccagcatagt gaacattctg    720
ggtcaagagc agttcatggc agtgtaccta tctgcaggtg ttatttccaa ttttgtcagt    780
tacctgggta agttgccac aggaagatat ggaccatcac ttggtgcatc tggtgccatc    840
atgacagtcc tcgcagctgt ctgcactaag atcccagaag ggaggcttgc cattattttc    900
cttccgatgt tcacgttcac agcagggaat gccctgaaag ccattatcgc catggataca    960
gcaggaatga tcctgggatg gaaattttt gatcatgcgg cacatcttgg gggagctctt   1020
tttggaatat ggtatgttac ttacggtcat gaactgattt ggaagaacag ggagccgcta   1080
gtgaaaatct ggcatgaaat aaggactaat ggccccaaaa aaggaggtgg ctctaagtaa   1140

<210> SEQ ID NO 8

```
<211> LENGTH: 379
<212> TYPE: PRT
<213> ORGANISM: Homo sapiens

<400> SEQUENCE: 8

Met Ala Trp Arg Gly Trp Ala Gln Arg Gly Trp Gly Cys Gly Gln Ala
1               5                   10                  15

Trp Gly Ala Ser Val Gly Gly Arg Ser Cys Glu Glu Leu Thr Ala Val
            20                  25                  30

Leu Thr Pro Pro Gln Leu Leu Gly Arg Arg Phe Asn Phe Phe Ile Gln
        35                  40                  45

Gln Lys Cys Gly Phe Arg Lys Ala Pro Arg Lys Val Glu Pro Arg Arg
    50                  55                  60

Ser Asp Pro Gly Thr Ser Gly Glu Ala Tyr Lys Arg Ser Ala Leu Ile
65                  70                  75                  80

Pro Pro Val Glu Glu Thr Val Phe Tyr Pro Ser Pro Tyr Pro Ile Arg
                85                  90                  95

Ser Leu Ile Lys Pro Leu Phe Phe Thr Val Gly Phe Thr Gly Cys Ala
            100                 105                 110

Phe Gly Ser Ala Ala Ile Trp Gln Tyr Glu Ser Leu Lys Ser Arg Val
        115                 120                 125

Gln Ser Tyr Phe Asp Gly Ile Lys Ala Asp Trp Leu Asp Ser Ile Arg
    130                 135                 140

Pro Gln Lys Glu Gly Asp Phe Arg Lys Glu Ile Asn Lys Trp Trp Asn
145                 150                 155                 160

Asn Leu Ser Asp Gly Gln Arg Thr Val Thr Gly Ile Ile Ala Ala Asn
                165                 170                 175

Val Leu Val Phe Cys Leu Trp Arg Val Pro Ser Leu Gln Arg Thr Met
            180                 185                 190

Ile Arg Tyr Phe Thr Ser Asn Pro Ala Ser Lys Val Leu Cys Ser Pro
        195                 200                 205

Met Leu Leu Ser Thr Phe Ser His Phe Ser Leu Phe His Met Ala Ala
    210                 215                 220

Asn Met Tyr Val Leu Trp Ser Phe Ser Ser Ser Ile Val Asn Ile Leu
225                 230                 235                 240

Gly Gln Glu Gln Phe Met Ala Val Tyr Leu Ser Ala Gly Val Ile Ser
                245                 250                 255

Asn Phe Val Ser Tyr Leu Gly Lys Val Ala Thr Gly Arg Tyr Gly Pro
            260                 265                 270

Ser Leu Gly Ala Ser Gly Ala Ile Met Thr Val Leu Ala Ala Val Cys
        275                 280                 285

Thr Lys Ile Pro Glu Gly Arg Leu Ala Ile Ile Phe Leu Pro Met Phe
    290                 295                 300

Thr Phe Thr Ala Gly Asn Ala Leu Lys Ala Ile Ile Ala Met Asp Thr
305                 310                 315                 320

Ala Gly Met Ile Leu Gly Trp Lys Phe Phe Asp His Ala Ala His Leu
                325                 330                 335

Gly Gly Ala Leu Phe Gly Ile Trp Tyr Val Thr Tyr Gly His Glu Leu
            340                 345                 350

Ile Trp Lys Asn Arg Glu Pro Leu Val Lys Ile Trp His Glu Ile Arg
        355                 360                 365

Thr Asn Gly Pro Lys Lys Gly Gly Ser Lys
    370                 375
```

<210> SEQ ID NO 9
<211> LENGTH: 2964
<212> TYPE: DNA
<213> ORGANISM: Homo sapiens

<400> SEQUENCE: 9

| | | | | | |
|---|---|---|---|---|---|
| gactcggcgc | gggcgccctc | ccggccagcg | gcggcagccc | ctcctcccccg | gcgccctcag | 60 |
| gaccccccag | agaccccccgg | cggcggcagc | ctgccttgct | ctgccaggaa | ccatgagtga | 120 |
| ggcccgcagg | gacagcacga | gcagcctgca | gcgcaagaag | ccaccctggc | taaagctgga | 180 |
| cattccctct | gcggtgcccc | tgacggcaga | agagcccagc | ttcctgcagc | ccctgaggcg | 240 |
| acaggctttc | ctgaggagtg | tgagtatgcc | agccgagaca | gcccacatct | cttcacccca | 300 |
| ccatgagctc | cggcggccgg | tgctgcaacg | ccagacgtcc | atcacacaga | ccatccgcag | 360 |
| ggggaccgcc | gactggtttg | gagtgagcaa | ggacagtgac | agcacccaga | aatggcagcg | 420 |
| caagagcatc | cgtcactgca | gccagcgcta | cgggaagctg | aagccccagg | tcctccggga | 480 |
| gctggacctg | cccagccagg | acaacgtgtc | gctgaccagc | accgagacgc | cacccccact | 540 |
| ctacgtgggg | ccatgccagc | tgggcatgca | gaagatcata | gaccccctgg | cccgtggccg | 600 |
| tgccttccgt | gtggcagatg | acactgcgga | aggcctgagt | gccccacaca | ctcccgtcac | 660 |
| gccgggtgct | gcctccctct | gctccttctc | cagctcccgc | tcaggttttcc | accggctccc | 720 |
| gcggcggcgc | aagcgagagt | cggtggccaa | gatgagcttc | cgggcggccg | cagcgctgat | 780 |
| gaaaggccgc | tccgttaggg | atggcacctt | tcgccgggca | cagcgtcgaa | gcttcactcc | 840 |
| agctagctttt | ctggaggagg | acacaactga | tttccccgat | gagctggaca | catccttctt | 900 |
| tgcccgggaa | ggtatcctcc | atgaagagct | gtccacatac | ccggatgaag | ttttcgagtc | 960 |
| cccatcggag | gcagcgctaa | aggactggga | gaaggcaccg | gagcaggcgg | acctcaccgg | 1020 |
| cggggccctg | gaccgcagcg | agcttgagcg | cagccacctg | atgctgccct | ggagcgagg | 1080 |
| ctggcggaag | cagaaggagg | gcgccgcagc | cccgcagccc | aaggtgcggc | tccgacagga | 1140 |
| ggtggtgagc | accgcggggc | cgcgacgggg | ccagcgtatc | gcggtgccgg | tgcgcaagct | 1200 |
| cttcgcccgg | gagaagcggc | cgtatgggct | gggcatggtg | ggacggctca | ccaaccgcac | 1260 |
| ctaccgcaag | cgcatcgaca | gcttcgtcaa | gcgccagatc | gaggacatgg | acgaccacag | 1320 |
| gcccttcttc | acctactggc | ttaccttcgt | gcactcgctc | gtcgccatcc | tagccgtgtg | 1380 |
| catctatggc | atcgcgcccg | tgggcttctc | gcagcatgag | acggtggact | cggtgctgcg | 1440 |
| gaaccgcggg | gtctacgaga | acgtcaagta | cgtgcagcag | gagaacttct | ggatcgggcc | 1500 |
| cagctcggag | gccctcatcc | acctgggcgc | caagttttcg | ccctgcatgc | gccaggaccc | 1560 |
| gcaggtgcac | agcttcattc | gctcggcgcg | cgagcgcgag | aagcactccg | cctgctgcgt | 1620 |
| gcgcaacgac | aggtcgggct | gcgtgcagac | ctcggaggag | gagtgctcgt | ccacgctggc | 1680 |
| agtgtgggtg | aagtggccca | tccatcccag | cgccccagag | cttgcgggcc | acaagagaca | 1740 |
| gtttggctct | gtctgccacc | aggatcccag | ggtgtgtgat | gagccctcct | ccgaagaccc | 1800 |
| tcatgagtgg | ccagaagaca | tcaccaagtg | gccgatctgc | accaaaaaca | gcgctgggaa | 1860 |
| ccacaccaac | catccccaca | tggactgtgt | catcacagga | cggccctgct | gcattggcac | 1920 |
| caagggcagg | tgtgagatca | cctcccggga | gtactgtgac | ttcatgaggg | gctacttcca | 1980 |
| tgaggaggcc | acgctctgct | ctcaggtgca | ctgcatggat | gatgtgtgtg | ggctcctgcc | 2040 |
| ttttctcaac | cccgaggtgc | ctgaccagtt | ctaccgcctg | tggctatccc | tcttcctgca | 2100 |
| cgccgggatc | ttgcactgcc | tggtgtccat | ctgcttccag | atgactgtcc | tgcgggacct | 2160 |

```
ggagaagctg gcaggctggc accgcatagc catcatctac ctgctgagtg gtgtcaccgg    2220
caacctggcc agtgccatct tcctgccata ccgagcagag gtgggtcctg ctggctccca    2280
gttcggcatc ctggcctgcc tcttcgtgga gctcttccag agctggcaga tcctggcgcg    2340
gccctggcgt gccttcttca agctgctggc tgtggtgctc ttcctcttca cctttgggct    2400
gctgccgtgg attgacaact tgcccacat  ctcggggttc atcagtggcc tcttcctctc    2460
cttcgccttc ttgccctaca tcagctttgg caagttcgac ctgtaccgga aacgctgcca    2520
gatcatcatc tttcaggtgg tcttcctggg cctcctggct ggcctggtgg tcctcttcta    2580
cgtctatcct gtccgctgtg agtggtgtga gttcctcacc tgcatcccct tcactgacaa    2640
gttctgtgag aagtacgaac tggacgctca gctccactga gctggctgcg ggctccagcg    2700
gccgtgtgct ccagcaggcc agagccagac acgacctccc tgagcctcac aggcttacag    2760
gagtcacctg ctccatgtgg ggactggcct gtttcctgaa cacagacctc tttcttgtgc    2820
cttgttcact tctgttgaac ccctcgtact gccgggcatt tattatacta cttcctgtca    2880
taaccttcta acttgtttct tgacgaccac ctcatgtggc aataaatga  actgggagcg    2940 ttttaaaaaa aaaaaaaaaa aaaa                                           2964
```

<210> SEQ ID NO 10
<211> LENGTH: 855
<212> TYPE: PRT
<213> ORGANISM: Homo sapiens

<400> SEQUENCE: 10

```
Met Ser Glu Ala Arg Arg Asp Ser Thr Ser Ser Leu Gln Arg Lys Lys
1               5                   10                  15

Pro Pro Trp Leu Lys Leu Asp Ile Pro Ser Ala Val Pro Leu Thr Ala
            20                  25                  30

Glu Glu Pro Ser Phe Leu Gln Pro Leu Arg Arg Gln Ala Phe Leu Arg
        35                  40                  45

Ser Val Ser Met Pro Ala Glu Thr Ala His Ile Ser Ser Pro His His
    50                  55                  60

Glu Leu Arg Arg Pro Val Leu Gln Arg Gln Thr Ser Ile Thr Gln Thr
65                  70                  75                  80

Ile Arg Arg Gly Thr Ala Asp Trp Phe Gly Val Ser Lys Asp Ser Asp
                85                  90                  95

Ser Thr Gln Lys Trp Gln Arg Lys Ser Ile Arg His Cys Ser Gln Arg
            100                 105                 110

Tyr Gly Lys Leu Lys Pro Gln Val Leu Arg Glu Leu Asp Leu Pro Ser
        115                 120                 125

Gln Asp Asn Val Ser Leu Thr Ser Thr Glu Thr Pro Pro Pro Leu Tyr
    130                 135                 140

Val Gly Pro Cys Gln Leu Gly Met Gln Lys Ile Ile Asp Pro Leu Ala
145                 150                 155                 160

Arg Gly Arg Ala Phe Arg Val Ala Asp Asp Thr Ala Glu Gly Leu Ser
                165                 170                 175

Ala Pro His Thr Pro Val Thr Pro Gly Ala Ala Ser Leu Cys Ser Phe
            180                 185                 190

Ser Ser Ser Arg Ser Gly Phe His Arg Leu Pro Arg Arg Lys Arg
        195                 200                 205

Glu Ser Val Ala Lys Met Ser Phe Arg Ala Ala Ala Leu Met Lys
    210                 215                 220

Gly Arg Ser Val Arg Asp Gly Thr Phe Arg Arg Ala Gln Arg Arg Ser
```

```
                225                 230                 235                 240
Phe Thr Pro Ala Ser Phe Leu Glu Glu Asp Thr Thr Asp Phe Pro Asp
                245                 250                 255
Glu Leu Asp Thr Ser Phe Phe Ala Arg Glu Gly Ile Leu His Glu Glu
                260                 265                 270
Leu Ser Thr Tyr Pro Asp Glu Val Phe Glu Ser Pro Ser Glu Ala Ala
                275                 280                 285
Leu Lys Asp Trp Glu Lys Ala Pro Glu Gln Ala Asp Leu Thr Gly Gly
                290                 295                 300
Ala Leu Asp Arg Ser Glu Leu Glu Arg Ser His Leu Met Leu Pro Leu
305                 310                 315                 320
Glu Arg Gly Trp Arg Lys Gln Lys Glu Gly Ala Ala Ala Pro Gln Pro
                325                 330                 335
Lys Val Arg Leu Arg Gln Glu Val Val Ser Thr Ala Gly Pro Arg Arg
                340                 345                 350
Gly Gln Arg Ile Ala Val Pro Val Arg Lys Leu Phe Ala Arg Glu Lys
                355                 360                 365
Arg Pro Tyr Gly Leu Gly Met Val Gly Arg Leu Thr Asn Arg Thr Tyr
370                 375                 380
Arg Lys Arg Ile Asp Ser Phe Val Lys Arg Gln Ile Glu Asp Met Asp
385                 390                 395                 400
Asp His Arg Pro Phe Phe Thr Tyr Trp Leu Thr Phe Val His Ser Leu
                405                 410                 415
Val Ala Ile Leu Ala Val Cys Ile Tyr Gly Ile Ala Pro Val Gly Phe
                420                 425                 430
Ser Gln His Glu Thr Val Asp Ser Val Leu Arg Asn Arg Gly Val Tyr
                435                 440                 445
Glu Asn Val Lys Tyr Val Gln Gln Glu Asn Phe Trp Ile Gly Pro Ser
                450                 455                 460
Ser Glu Ala Leu Ile His Leu Gly Ala Lys Phe Ser Pro Cys Met Arg
465                 470                 475                 480
Gln Asp Pro Gln Val His Ser Phe Ile Arg Ser Ala Arg Glu Arg Glu
                485                 490                 495
Lys His Ser Ala Cys Cys Val Arg Asn Asp Arg Ser Gly Cys Val Gln
                500                 505                 510
Thr Ser Glu Glu Glu Cys Ser Ser Thr Leu Ala Val Trp Val Lys Trp
                515                 520                 525
Pro Ile His Pro Ser Ala Pro Glu Leu Ala Gly His Lys Arg Gln Phe
                530                 535                 540
Gly Ser Val Cys His Gln Asp Pro Arg Val Cys Asp Glu Pro Ser Ser
545                 550                 555                 560
Glu Asp Pro His Glu Trp Pro Glu Asp Ile Thr Lys Trp Pro Ile Cys
                565                 570                 575
Thr Lys Asn Ser Ala Gly Asn His Thr Asn His Pro His Met Asp Cys
                580                 585                 590
Val Ile Thr Gly Arg Pro Cys Cys Ile Gly Thr Lys Gly Arg Cys Glu
                595                 600                 605
Ile Thr Ser Arg Glu Tyr Cys Asp Phe Met Arg Gly Tyr Phe His Glu
                610                 615                 620
Glu Ala Thr Leu Cys Ser Gln Val His Cys Met Asp Asp Val Cys Gly
625                 630                 635                 640
Leu Leu Pro Phe Leu Asn Pro Glu Val Pro Asp Gln Phe Tyr Arg Leu
                645                 650                 655
```

```
Trp Leu Ser Leu Phe Leu His Ala Gly Ile Leu His Cys Leu Val Ser
              660                 665                 670
Ile Cys Phe Gln Met Thr Val Leu Arg Asp Leu Glu Lys Leu Ala Gly
          675                 680                 685
Trp His Arg Ile Ala Ile Ile Tyr Leu Leu Ser Gly Val Thr Gly Asn
      690                 695                 700
Leu Ala Ser Ala Ile Phe Leu Pro Tyr Arg Ala Glu Val Gly Pro Ala
705                 710                 715                 720
Gly Ser Gln Phe Gly Ile Leu Ala Cys Leu Phe Val Glu Leu Phe Gln
              725                 730                 735
Ser Trp Gln Ile Leu Ala Arg Pro Trp Arg Ala Phe Lys Leu Leu
          740                 745                 750
Ala Val Val Leu Phe Leu Phe Thr Phe Gly Leu Leu Pro Trp Ile Asp
              755                 760                 765
Asn Phe Ala His Ile Ser Gly Phe Ile Ser Gly Leu Phe Leu Ser Phe
      770                 775                 780
Ala Phe Leu Pro Tyr Ile Ser Phe Gly Lys Phe Asp Leu Tyr Arg Lys
785                 790                 795                 800
Arg Cys Gln Ile Ile Ile Phe Gln Val Val Phe Leu Gly Leu Leu Ala
              805                 810                 815
Gly Leu Val Val Leu Phe Tyr Val Tyr Pro Val Arg Cys Glu Trp Cys
          820                 825                 830
Glu Phe Leu Thr Cys Ile Pro Phe Thr Asp Lys Phe Cys Glu Lys Tyr
      835                 840                 845
Glu Leu Asp Ala Gln Leu His
  850                 855

<210> SEQ ID NO 11
<211> LENGTH: 2643
<212> TYPE: DNA
<213> ORGANISM: Homo sapiens

<400> SEQUENCE: 11
gctactccca cctgccacgc cgcaagagaa tgtctgtggc ccacatgagc ttgcaagctg      60
ccgctgccct cctcaagggg cgctcggtgc tggatgccac cggacagcgg tgccgggtgg     120
tcaagcgcag ctttgccttc ccgagcttcc tggaggagga tgtggtcgat ggggcagaca     180
cgtttgactc ctcctttttt agtaaggaag aaatgagctc catgcctgat gatgtctttg     240
agtcccccca actctctgcc agctacttcc gagggatccc acactcagcc tcccctgtct     300
cccccgatgg ggtgcaaatc cctctgaagg agtatggccg agcccccagtc cccggggcccc     360
ggcgcggcaa gcgcatcgcc tccaaggtga agcactttgc ctttgatcgg aagaagcggc     420
actacggcct cggcgtggtg ggcaactggc tgaaccgcag ctaccgccgc agcatcagca     480
gcactgtgca gcggcagctg gagagcttcg acagccaccg gccctacttc acctactggc     540
tgaccttcgt ccatgtcatc atcacgctgc tggtgatttg cacgtatggc atcgcacccg     600
tgggcttttgc ccagcacgtc accacccagc tggtgctgcg gaacaaaggt gtgtacgaga     660
gcgtgaagta catccagcag gagaacttct gggttggccc cagctcgatt gacctgatcc     720
acctggggggc caagttctca ccctgcatcc ggaaggacgg gcagatcgag cagctggtgc     780
tgcgcgagcg agacctggag cgggactcag gctgctgtgt ccagaatgac cactccggat     840
gcatccagac ccagcggaag gactgctcgg agactttggc cactttttgtc aagtggcagg     900
atgacactgg gcccccatg gacaagtctg atctgggcca agagcggact tcgggggctg     960
```

-continued

```
tctgccacca ggacccagg acctgcgagg agccagcctc cagcggtgcc cacatctggc      1020
ccgatgacat cactaagtgg ccgatctgca cagagcaggc caggagcaac cacacaggct      1080
tcctgcacat ggactgcgag atcaagggcc gcccctgctg catcggcacc aagggcagct      1140
gtgagatcac cacccgggaa tactgtgagt tcatgcacgg ctatttccat gaggaagcaa      1200
cactctgctc ccaggtgcac tgcttggaca aggtgtgtgg gctgctgccc ttcctcaacc      1260
ctgaggtccc agatcagttc tacaggctct ggctgtctct cttcctacat gctggcgtgg      1320
tgcactgcct cgtgtctgtg gtctttcaaa tgaccatcct gagggacctg agaagctgg       1380
ccggctggca ccgtatcgcc atcatcttca tcctcagtgg catcacaggc aacctcgcca      1440
gtgccatctt tctcccatac cgggcagagg tgggcccggc cggctcacag ttcggcctcc      1500
tcgcctgcct cttcgtggag ctcttccaga gctggccgct gctggagagg ccctggaagg      1560
ccttcctcaa cctctcggcc atcgtgctct tcctgttcat ctgtggcctc ttgccctgga      1620
tcgacaacat cgcccacatc ttcggcttcc tcagtggcct gctgctggcc ttcgccttcc      1680
tgccctacat caccttcggc accagcgaca gtaccgcaa gcgggcactc atcctggtgt       1740
cactgctggc ctttgccggc ctcttcgccg ccctcgtgct gtggctgtac atctacccca     1800
ttaactggcc ctggatcgag cacctcacct gcttcccctt caccagccgc ttctgcgaga      1860
agtatgagct ggaccaggtg ctgcactgac cgctgggcca cacggctgcc cctcagcccc      1920
gctggaacag ggtctgcctg cgagggctgc cctctgcaga gcgctctctg tgtgccagag      1980
agccagagac ccaagacagg gcccgggctc tggacctggg tgcccccctg ccaggcgagg      2040
ctgactccgc gtgagatggt tggttaaggc ggggttttc tggggcgtga ggcctgtgag       2100
atcctgaccc aagctcaggc acacccaagg cacctgcctc tctgagtctt gggtctcagt      2160
tcctaatatc ccgctccttg ctgagaccat ctcctggggc agggtccttt tcttcccagg      2220
tcctcagcgc tgcctctgct ggtgccttct cccccactac tactgagcg tgcccttgct       2280
ggggacgtgg ctgtgccctc agttgccccc agggctgggt gcccaccatg cccttcctc      2340
tttctcctcc tacctctgcc ctgtgagccc atccataagg ctctcagatg ggacattgta      2400
ggaaaggctt tggccatggt ctgggggcag agaacaaggg gggagacaca gtagacctc      2460
aggtagaacg acaccgggcg gagccacccc agggcctgct cccagggagt gctcgaggcg      2520
catcaggccc gttttttacc agtttatatc acggtcttca tttttaaaag taacgctaac      2580
tttgtacgga cgatgtctca tggattaaat aatattcttt atggcaaaaa aaaaaaaaaa      2640
aaa                                                                   2643
```

<210> SEQ ID NO 12
<211> LENGTH: 619
<212> TYPE: PRT
<213> ORGANISM: Homo sapiens

<400> SEQUENCE: 12

```
Met Ser Val Ala His Met Ser Leu Gln Ala Ala Ala Leu Leu Lys
1               5                  10                  15

Gly Arg Ser Val Leu Asp Ala Thr Gly Gln Arg Cys Arg Val Val Lys
                20                  25                  30

Arg Ser Phe Ala Phe Pro Ser Phe Leu Glu Glu Asp Val Val Asp Gly
            35                  40                  45

Ala Asp Thr Phe Asp Ser Ser Phe Phe Ser Lys Glu Glu Met Ser Ser
        50                  55                  60
```

```
Met Pro Asp Asp Val Phe Glu Ser Pro Pro Leu Ser Ala Ser Tyr Phe
 65              70              75                 80

Arg Gly Ile Pro His Ser Ala Ser Pro Val Ser Pro Asp Gly Val Gln
             85              90              95

Ile Pro Leu Lys Glu Tyr Gly Arg Ala Pro Val Pro Gly Pro Arg Arg
            100             105             110

Gly Lys Arg Ile Ala Ser Lys Val Lys His Phe Ala Phe Asp Arg Lys
            115             120             125

Lys Arg His Tyr Gly Leu Gly Val Val Gly Asn Trp Leu Asn Arg Ser
130             135             140

Tyr Arg Arg Ser Ile Ser Ser Thr Val Gln Arg Gln Leu Glu Ser Phe
145             150             155             160

Asp Ser His Arg Pro Tyr Phe Thr Tyr Trp Leu Thr Phe Val His Val
                165             170             175

Ile Ile Thr Leu Leu Val Ile Cys Thr Tyr Gly Ile Ala Pro Val Gly
            180             185             190

Phe Ala Gln His Val Thr Thr Gln Leu Val Leu Arg Asn Lys Gly Val
            195             200             205

Tyr Glu Ser Val Lys Tyr Ile Gln Gln Glu Asn Phe Trp Val Gly Pro
            210             215             220

Ser Ser Ile Asp Leu Ile His Leu Gly Ala Lys Phe Ser Pro Cys Ile
225             230             235             240

Arg Lys Asp Gly Gln Ile Glu Gln Leu Val Leu Arg Glu Arg Asp Leu
            245             250             255

Glu Arg Asp Ser Gly Cys Cys Val Gln Asn Asp His Ser Gly Cys Ile
            260             265             270

Gln Thr Gln Arg Lys Asp Cys Ser Glu Thr Leu Ala Thr Phe Val Lys
            275             280             285

Trp Gln Asp Asp Thr Gly Pro Pro Met Asp Lys Ser Asp Leu Gly Gln
290             295             300

Lys Arg Thr Ser Gly Ala Val Cys His Gln Asp Pro Arg Thr Cys Glu
305             310             315             320

Glu Pro Ala Ser Ser Gly Ala His Ile Trp Pro Asp Asp Ile Thr Lys
            325             330             335

Trp Pro Ile Cys Thr Glu Gln Ala Arg Ser Asn His Thr Gly Phe Leu
            340             345             350

His Met Asp Cys Glu Ile Lys Gly Arg Pro Cys Cys Ile Gly Thr Lys
            355             360             365

Gly Ser Cys Glu Ile Thr Thr Arg Glu Tyr Cys Glu Phe Met His Gly
            370             375             380

Tyr Phe His Glu Glu Ala Thr Leu Cys Ser Gln Val His Cys Leu Asp
385             390             395             400

Lys Val Cys Gly Leu Leu Pro Phe Leu Asn Pro Glu Val Pro Asp Gln
            405             410             415

Phe Tyr Arg Leu Trp Leu Ser Leu Phe Leu His Ala Gly Val Val His
            420             425             430

Cys Leu Val Ser Val Val Phe Gln Met Thr Ile Leu Arg Asp Leu Glu
            435             440             445

Lys Leu Ala Gly Trp His Arg Ile Ala Ile Phe Ile Leu Ser Gly
450             455             460

Ile Thr Gly Asn Leu Ala Ser Ala Ile Phe Leu Pro Tyr Arg Ala Glu
465             470             475             480

Val Gly Pro Ala Gly Ser Gln Phe Gly Leu Leu Ala Cys Leu Phe Val
```

```
                485               490               495
Glu Leu Phe Gln Ser Trp Pro Leu Leu Glu Arg Pro Trp Lys Ala Phe
            500               505               510
Leu Asn Leu Ser Ala Ile Val Leu Phe Leu Phe Ile Cys Gly Leu Leu
            515               520               525
Pro Trp Ile Asp Asn Ile Ala His Ile Phe Gly Phe Leu Ser Gly Leu
            530               535               540
Leu Leu Ala Phe Ala Phe Leu Pro Tyr Ile Thr Phe Gly Thr Ser Asp
545               550               555               560
Lys Tyr Arg Lys Arg Ala Leu Ile Leu Val Ser Leu Leu Ala Phe Ala
                565               570               575
Gly Leu Phe Ala Ala Leu Val Leu Trp Leu Tyr Ile Tyr Pro Ile Asn
            580               585               590
Trp Pro Trp Ile Glu His Leu Thr Cys Phe Pro Phe Thr Ser Arg Phe
            595               600               605
Cys Glu Lys Tyr Glu Leu Asp Gln Val Leu His
            610               615

<210> SEQ ID NO 13
<211> LENGTH: 1305
<212> TYPE: DNA
<213> ORGANISM: Homo sapiens

<400> SEQUENCE: 13
atggggcggg gcctctggga ggcgtggcct ccggccggct cctctgctgt tgccaaggga    60
aactgccgcg aggaggcgga aggagcagag gaccggcagc cggcgtcgag gcggggcgcg   120
ggaacgacgg cggccatggc ggcctcgggg cccgggtgtc gcagctggtg cttgtgtccc   180
gaggtgccat ccgccaccct cttcactgcg ctgctctcgc tgctggtttc cgggcctcgc   240
ctgttcctgc tgcagcagcc cctggcgccc tcgggcctca cgctgaagtc cgaggccctt   300
cgcaactggc aagtttacag gctggtaacc tacatctttg tctacgagaa tcccatctcc   360
ctgctctgcg cgctatcat catctggcgc tttgctggca atttcgagag aaccgtgggc   420
accgtccgcc actgcttctt caccgtgatc ttcgccatct tctccgctat catcttcctg   480
tcattcgagg ctgtgtcatc actgtcaaag ctgggggaag tggaggatgc agaggtttc    540
accccagtgg cctttgccat gctgggagtc accaccgtcc gttctcggat gaggcgggcc   600
ctggtgtttg gcatggttgt gccctcagtc ctggttccgt ggctcctgct gggtgcctcg   660
tggctcattc cccagacctc tttcctcagt aatgtctgcg ggctgtccat cgggctggcc   720
tatgctcacc tactgctatt ccatcgacct ctcagagcga gtggcgctga agctcgatca   780
gaccttcccc ttcagcctga tgaggaggat atccgtgttc aagtacgtct cagggtcttc   840
agccgagagg agggcagccc agagccggaa actgaacccg gtgcctggct cctaccccac   900
acagagctgc caccctcacc tgtccccaag ccaccctgtg tcccagacgc agcacgccag   960
tggtcagaag ctggcctcct ggcctcctgc acccccgggc acatgcccac cttgcctccg  1020
taccagcctg cctccggcct gtgctatgtg cagaaccact ttggtccaaa ccccacctcc  1080
tccagtgtct acccagcttc tgcgggcacc tccctgggca tccagccccc cacgcctgtg  1140
aacagccctg gcacggtgta ttctggggcc ttgggacacc aggggctgca ggctccaagg  1200
agtcctccag ggtccccatg ccctgagaga atttctaggg aagtcatctc acttggcctt  1260
ctgaaggtcc tccctaagag tctcctgaca aaagttactt attga                  1305
```

```
<210> SEQ ID NO 14
<211> LENGTH: 434
<212> TYPE: PRT
<213> ORGANISM: Homo sapiens

<400> SEQUENCE: 14

Met Gly Arg Gly Leu Trp Glu Ala Trp Pro Ala Gly Ser Ser Ala
1               5                   10                  15

Val Ala Lys Gly Asn Cys Arg Glu Glu Ala Gly Ala Glu Asp Arg
                20                  25                  30

Gln Pro Ala Ser Arg Arg Gly Ala Gly Thr Thr Ala Ala Met Ala Ala
                35                  40                  45

Ser Gly Pro Gly Cys Arg Ser Trp Cys Leu Cys Pro Glu Val Pro Ser
    50                  55                  60

Ala Thr Phe Phe Thr Ala Leu Leu Ser Leu Leu Val Ser Gly Pro Arg
65                  70                  75                  80

Leu Phe Leu Leu Gln Gln Pro Leu Ala Pro Ser Gly Leu Thr Leu Lys
                85                  90                  95

Ser Glu Ala Leu Arg Asn Trp Gln Val Tyr Arg Leu Val Thr Tyr Ile
                100                 105                 110

Phe Val Tyr Glu Asn Pro Ile Ser Leu Leu Cys Gly Ala Ile Ile Ile
                115                 120                 125

Trp Arg Phe Ala Gly Asn Phe Glu Arg Thr Val Gly Thr Val Arg His
            130                 135                 140

Cys Phe Phe Thr Val Ile Phe Ala Ile Phe Ser Ala Ile Ile Phe Leu
145                 150                 155                 160

Ser Phe Glu Ala Val Ser Ser Leu Ser Lys Leu Gly Glu Val Glu Asp
                165                 170                 175

Ala Arg Gly Phe Thr Pro Val Ala Phe Ala Met Leu Gly Val Thr Thr
                180                 185                 190

Val Arg Ser Arg Met Arg Arg Ala Leu Val Phe Gly Met Val Val Pro
            195                 200                 205

Ser Val Leu Val Pro Trp Leu Leu Leu Gly Ala Ser Trp Leu Ile Pro
    210                 215                 220

Gln Thr Ser Phe Leu Ser Asn Val Cys Gly Leu Ser Ile Gly Leu Ala
225                 230                 235                 240

Tyr Ala His Leu Leu Leu Phe His Arg Pro Leu Arg Ala Ser Gly Ala
                245                 250                 255

Glu Ala Arg Ser Asp Leu Pro Leu Gln Pro Asp Glu Glu Asp Ile Arg
                260                 265                 270

Val Gln Val Arg Leu Arg Val Phe Ser Arg Glu Glu Gly Ser Pro Glu
            275                 280                 285

Pro Glu Thr Glu Pro Gly Ala Trp Leu Leu Pro His Thr Glu Leu Pro
    290                 295                 300

Pro Ser Pro Val Pro Lys Pro Pro Cys Val Pro Asp Ala Ala Arg Gln
305                 310                 315                 320

Trp Ser Glu Ala Gly Leu Leu Ala Ser Cys Thr Pro Gly His Met Pro
                325                 330                 335

Thr Leu Pro Pro Tyr Gln Pro Ala Ser Gly Leu Cys Tyr Val Gln Asn
                340                 345                 350

His Phe Gly Pro Asn Pro Thr Ser Ser Val Tyr Pro Ala Ser Ala
            355                 360                 365

Gly Thr Ser Leu Gly Ile Gln Pro Pro Thr Pro Val Asn Ser Pro Gly
    370                 375                 380
```

-continued

| Thr | Val | Tyr | Ser | Gly | Ala | Leu | Gly | His | Gln | Gly | Leu | Gln | Ala | Pro | Arg |
| | | | 385 | | | | 390 | | | | 395 | | | | 400 |

| Ser | Pro | Pro | Gly | Ser | Pro | Cys | Pro | Glu | Arg | Ile | Ser | Arg | Glu | Val | Ile |
| | | | | 405 | | | | 410 | | | | | 415 | | |

| Ser | Leu | Gly | Leu | Leu | Lys | Val | Leu | Pro | Lys | Ser | Leu | Leu | Thr | Lys | Val |
| | | | 420 | | | | | 425 | | | | 430 | | | |

Thr Tyr

<210> SEQ ID NO 15
<211> LENGTH: 1738
<212> TYPE: DNA
<213> ORGANISM: Homo sapiens

<400> SEQUENCE: 15

| tgctgactaa | tccgcgggcc | gcggggaatg | ggtggcgcgc | cagccggtcg | gcagggggtca | 60 |
| cgcggccggg | tgtgcgcgga | atggattcag | ggttctcggg | tcgcgcccgg | gagctagagt | 120 |
| cctgactccc | agccgggggtc | cccgaccggc | ctttcggggt | tgccgggcgc | gctctgcaaa | 180 |
| ggggaaactg | aggcccaagg | aaattgagta | tctctgcaaa | gtcaccagct | gagttcgaac | 240 |
| cagacagatc | ctgggacccc | ctactctatc | cgccaccgga | agaatctccg | tccttgtctt | 300 |
| tccattctgc | cctcccggct | tcccagtaag | cacacagccc | caggaccacc | cttgaccgtc | 360 |
| ctcaaccaag | cgatgcatgc | cagggccccc | catggccaac | tgtccccagc | actgcctctg | 420 |
| gcctcctcag | tcctgatgct | gctgatgagc | accctgtggc | tggtgggggc | cggccccggc | 480 |
| ctggtcctgg | ccccggagct | gttgctggac | ccctggcagg | tgcaccggct | gctgacccat | 540 |
| gccctgggcc | acacggccct | gccaggcctg | ctcctgagcc | tgctgctcct | gcccactgtg | 600 |
| ggctggcagc | aggagtgcca | cctgggcacg | ctgagattcc | tgcatgcctc | agccctgctc | 660 |
| gccctggctt | ctgggctgct | ggcagtgctg | ctggcaggcc | ttgggctgtc | cagtgcagcc | 720 |
| ggcagctgtg | gatacatgcc | tgtccacctg | gccatgctgg | ctggggaggg | acaccgccct | 780 |
| agacggcccc | gtgggggcact | gccaccgtgg | ctgtcgccgt | ggctgctgct | tgccctgacc | 840 |
| ccactgctca | gctctgagcc | acccttcctg | cagctcctttt | gcggcctcct | tgccggcctg | 900 |
| gcctatgcag | ctggggcctt | ccggtggctg | aaccctcag | agcgacggct | gcaggtgctg | 960 |
| caggagggcg | tcttgtgcag | gaccttggcg | gggtgctggc | ccctgaggct | ccttgccacc | 1020 |
| ccgggtagcc | tggcggagct | gcctgtcacc | catcctgccg | gagtgaggcc | tcccatccct | 1080 |
| ggaccgcctt | atgtgcctc | ccctgacctc | tggtcccact | gggaagactc | agccctgccc | 1140 |
| ccaccaagcc | tgaggcctgt | gcagcccacc | tgggaggggct | cctcagaggc | aggcctggac | 1200 |
| tgggctgggg | ccagcttctc | cccagggact | ccgatgtggg | cggccttgga | tgagcagatg | 1260 |
| ctgcaggagg | gcatccaggc | ctcgcttctt | gacgggccag | cccaggaacc | ccagagcgca | 1320 |
| ccatggctgt | ccaagtcctc | tgtctcctct | ctgcggctgc | agcagctgga | gcgcatgggc | 1380 |
| ttccctacgg | agcaggcggt | ggtggcactg | gcagccacag | gccgtgtgga | gggtgccgtg | 1440 |
| tcactgttgg | ttggaggaca | agtgggcact | gagaccctgg | tgacccatgg | aaagggtggg | 1500 |
| cctgcccact | ccgagggtcc | tgggcctccc | tagcccaggc | agagagtggg | gcacaggcag | 1560 |
| gcccttgggt | gctaagggct | gggctgcatg | tgggtagccc | gagctcctac | tctgtctaaa | 1620 |
| gagggccaca | gtggggagca | ggggcacctc | tggaggcagg | agaggccccc | cagcatgctg | 1680 |
| ccctagtacg | tgtttagaat | aaaaaccagt | ttgttttttca | acctggacct | ccttggag | 1738 |

<210> SEQ ID NO 16

```
<211> LENGTH: 386
<212> TYPE: PRT
<213> ORGANISM: Homo sapiens

<400> SEQUENCE: 16

Met His Ala Arg Gly Pro His Gly Gln Leu Ser Pro Ala Leu Pro Leu
 1               5                  10                  15

Ala Ser Ser Val Leu Met Leu Leu Met Ser Thr Leu Trp Leu Val Gly
             20                  25                  30

Ala Gly Pro Gly Leu Val Leu Ala Pro Glu Leu Leu Leu Asp Pro Trp
         35                  40                  45

Gln Val His Arg Leu Leu Thr His Ala Leu Gly His Thr Ala Leu Pro
     50                  55                  60

Gly Leu Leu Ser Leu Leu Leu Pro Thr Val Gly Trp Gln Gln
 65                  70                  75                  80

Glu Cys His Leu Gly Thr Leu Arg Phe Leu His Ala Ser Ala Leu Leu
                 85                  90                  95

Ala Leu Ala Ser Gly Leu Leu Ala Val Leu Leu Ala Gly Leu Gly Leu
            100                 105                 110

Ser Ser Ala Ala Gly Ser Cys Gly Tyr Met Pro Val His Leu Ala Met
            115                 120                 125

Leu Ala Gly Glu Gly His Arg Pro Arg Arg Pro Arg Gly Ala Leu Pro
        130                 135                 140

Pro Trp Leu Ser Pro Trp Leu Leu Ala Leu Thr Pro Leu Leu Ser
145                 150                 155                 160

Ser Glu Pro Pro Phe Leu Gln Leu Leu Cys Gly Leu Leu Ala Gly Leu
                165                 170                 175

Ala Tyr Ala Ala Gly Ala Phe Arg Trp Leu Glu Pro Ser Glu Arg Arg
            180                 185                 190

Leu Gln Val Leu Gln Glu Gly Val Leu Cys Arg Thr Leu Ala Gly Cys
        195                 200                 205

Trp Pro Leu Arg Leu Leu Ala Thr Pro Gly Ser Leu Ala Glu Leu Pro
210                 215                 220

Val Thr His Pro Ala Gly Val Arg Pro Pro Ile Pro Gly Pro Pro Tyr
225                 230                 235                 240

Val Ala Ser Pro Asp Leu Trp Ser His Trp Glu Asp Ser Ala Leu Pro
                245                 250                 255

Pro Pro Ser Leu Arg Pro Val Gln Pro Thr Trp Glu Gly Ser Ser Glu
            260                 265                 270

Ala Gly Leu Asp Trp Ala Gly Ala Ser Phe Ser Pro Gly Thr Pro Met
        275                 280                 285

Trp Ala Ala Leu Asp Glu Gln Met Leu Gln Glu Gly Ile Gln Ala Ser
    290                 295                 300

Leu Leu Asp Gly Pro Ala Gln Glu Pro Gln Ser Ala Pro Trp Leu Ser
305                 310                 315                 320

Lys Ser Ser Val Ser Ser Leu Arg Leu Gln Gln Leu Glu Arg Met Gly
                325                 330                 335

Phe Pro Thr Glu Gln Ala Val Val Leu Ala Ala Thr Gly Arg Val
        340                 345                 350

Glu Gly Ala Val Ser Leu Leu Val Gly Gly Gln Val Gly Thr Glu Thr
        355                 360                 365

Leu Val Thr His Gly Lys Gly Gly Pro Ala His Ser Glu Gly Pro Gly
    370                 375                 380

Pro Pro
```

<210> SEQ ID NO 17
<211> LENGTH: 19
<212> TYPE: PRT
<213> ORGANISM: Homo sapiens

<400> SEQUENCE: 17

Met Gly Arg Val Glu Asp Gly Gly Thr Thr Glu Glu Leu Glu Asp Trp
1               5                   10                  15
Asp Pro Gly

<210> SEQ ID NO 18
<211> LENGTH: 1559
<212> TYPE: DNA
<213> ORGANISM: Homo sapiens

<400> SEQUENCE: 18

```
cttggacctt ggccctcgct ttccaggatg ggtagggtgg aagacggggg aacaactgag      60
gagctggagg actgggaccc aggcaccagt gccctgccag ctcctgggat caagcagggt     120
cccagggaac agacaggcac ggggcccctg tcccaaaagt gctgggagcc tgagcctgat     180
gctcccagcc agcctggccc agcccttttgg tccaggggtc gggcccgcac tcaggccttg    240
gctggcggct cctcactgca gcagctggac cccgagaaca caggcttcat cggtgcggac    300
accttcactg gcctggtgca cagccatgag ctgcccctgg acccggccaa gctggacatg    360
ctggtggccc tggctcagag caacgagcag ggccaggtct gctaccagga gctggtggac    420
ctgatcagca gcaagcgctc cagcagtttc aagcgggcca ttgctaacgg acagcgggca    480
ctgccccggg acgggccgct ggatgagcca ggcctaggtg tctacaagcg gtttgtgcgt    540
tacgtggcct acgagatcct gccttgtgag gtggaccgcc gctggtactt ctaccgtcac    600
cgcagctgcc accccccgt gttcatggcc tcggtcactc ttgcccagat catcgtgttc    660
ctgtgttacg gggcccgcct caacaagtgg gtgctgcaga cctaccaccc cgagtacatg    720
aagagccccc ttgtgtacca ccccgggcac cgtgcccgcg cctggcgctt cctcacctac    780
atgttcatgc acgttgggct ggagcagctg gggttcaacg ccctcctgca gctgatgatc    840
ggggtgcccc tggagatggt gcacggcctg ctccgcatca gcctgctcta cctggcaggc    900
gtgctggcag gctccctaac cgtctccatc accgacatgc gggccccggt ggtgggaggc    960
tccggcgggg tctacgccct gtgctcggca cacctggcca acgttgtcat gaactgggct   1020
gggatgagat gtccctacaa gttgctgagg atggtgctgg ccttggtgtg catgagctcc   1080
gaggtgggcc gggccgtgtg gctgcgcttc tccccgccgc tgcccgcctc gggcccacag   1140
cccagcttca tggcgcacct ggcaggcgcg gtggtggggg tgagcatggg cctgaccatc   1200
ctgcggagct acgaggagcg cctgcgggac cagtgcggct ggtgggtggt gctgctggcc   1260
tacggcacct tcctgctctt cgccgtcttc tggaacgtct tcgcctacga cctgctgggc   1320
gcccacatcc ccccaccgcc ctgaccggct acctgaggct gcacaggcca gggctcgggc   1380
atgtggtggc cgcccaccag gggccttcac gtctgcccctt tgtgaacgga cgtctcaggg   1440
ctgctgtgcc ccttgggtgt gggtggcctc aaaggaggcc ctgtcccagc cacccacccc   1500
ccactcccag gacttgcggt ctgagccttt ttggataatt aataaatatt ttacacagc    1559
```

<210> SEQ ID NO 19
<211> LENGTH: 593
<212> TYPE: DNA
<213> ORGANISM: Homo sapiens -continued

```
<400> SEQUENCE: 19
atttactatg ctgtgtggaa gcctcagaaa cagtggatca cgttggacac aggcatcttg      60
gagagtccct ttatctacag tcctgagaag agggaggaag cctggaggtt tatctcatac     120
atgctggtac atgctggagt tcagcacatc ttggggaatc tttgtatgca gcttgttttg     180
ggtattccct tggaaatggt ccacaaaggc ctccgtgtgg ggctggtgta cctggcagga     240
gtgattgcag ggtcccttgc cagctccatc tttgacccac tcagatatct tgtgggagct     300
tcaggaggag tctatgctct gatgggaggc tattttatga atgttctggt gaattttcaa     360
gaaatgattc ctgcctttgg aattttcaga ctgctgatca tcatcctgat aattgtgttg     420
gacatgggat ttgctctcta tagaaggttc tttgttcctg aagatgggtc tccggtgtct     480
tttgcagctc acattgcagg tggatttgct ggaatgtcca ttggctacac ggtgtttagc     540
tgctttgata agcactgct gaaagatcca aggttatgga tagcaattgc tgc             593

<210> SEQ ID NO 20
<211> LENGTH: 708
<212> TYPE: DNA
<213> ORGANISM: Homo sapiens

<400> SEQUENCE: 20
aaggaggagc gcctggcaga gcgggatctt cagggcagcg ggcaacccct tggcccagga      60
agcctggaac gcaaggaccg gagggcgtgg gctgggacgc ccctacgttg gtctttcagg     120
gaaaggcctt ggaaagcagt cgttgcgcca gacagcccag ggaagagcgg cagcctgagg     180
acctagggcc acctgctgtt ccctgggatt catgtccttc tggggaggag ggaggaccca     240
ggacaatggc tgctgttcat gatctggaga tggagagcat gaatctgaat atggggagag     300
agatgaaaga agagctggag gaagaggaga aaatgagaga ggatggggga ggtaaagatc     360
gggccaagag taaaaaggtc cacaggattg tctcaaaatg gatgctgccc gaaaagtccc     420
gaggaacata cttggagaga gctaactgct tcccgcctcc cgtgttcatc atctccatca     480
gcctggccga gctggcagtg tttatttact atgctgtgtg gaagcctcag aaacagtgga     540
tcacgttgga cacaggcatc ttggagagtc cctttatcta cagtcctgag aagagggagg     600
aagcctggag gtttatctca tacatgctgg tacatgctgg gtaagcaatg atagttaagc     660
cctggtatca gaggtgatta tcattgta acctcttaaa acaaaaaa                     708

<210> SEQ ID NO 21
<211> LENGTH: 616
<212> TYPE: DNA
<213> ORGANISM: Homo sapiens
<220> FEATURE:
<221> NAME/KEY: misc_feature
<222> LOCATION: (498)..(498)
<223> OTHER INFORMATION: "n" is A, C, G, or T

<400> SEQUENCE: 21
cttcttccct ttctacatta agaagcccct tccttaaatc ctaaggtcct tttataggca      60
atctttgcaa ctgatgagtt taatgctgtt ttgtcctcta tataaaattg ttagcctttg     120
ctgagacttc tctgtttctt catagaggct tccctttttt tttttatttc ctccagatgg     180
ctctttttat taattgactt acaatagggg caggtcagtt tgctggagat aggaaaatgt     240
tgaaaaacac agcaaataag acacaagcta aatatgcagc aattgctatc caaaaccttg     300
gatctttcat cagtgcttta tcaaagcagc taaacaccgt gtagccaatg gacattccag     360
```

```
caaatccacc tgcaatgtga gctgcaaaag acaccggaga cccatcttca ggaacaaaga      420
accttctata gagagcaaat cccatgtcca acacaattat caggatgatg atcagcagtc      480
tgaaaattcc aaaggcanga atcatttctt gaaaattcac cagaacattc ataaaatagc      540
ctcccatcag agcatagact cctcctgaag ctcccacaag atatctgagt gggtcaaaga      600
tggagctggc aaggga                                                     616

<210> SEQ ID NO 22
<211> LENGTH: 354
<212> TYPE: DNA
<213> ORGANISM: Homo sapiens

<400> SEQUENCE: 22
tggatcacgt tggacacagg catttggaga gtccctttat ctacagtcct gagaagaggg       60
aggaagcctg gaggtttatc tcacacatgc tggtacatgc tggagttcag cacatcttgg      120
ggaatctttg tatgcagctt gttttgggta ttcccttgga aatggtccac aaaggcctcc      180
gtgtggggct ggtgtacctg caggagtga ttgcagggtc ccttgccagc tccatctttg       240
acccactcag atatcttgtg ggagcttcag gaggagtcta tgctctgatg ggaggctatt      300
ttatgaatgt tctggtgaat tttcaagaaa tgattcctgc ctttggaatt ttca            354

<210> SEQ ID NO 23
<211> LENGTH: 356
<212> TYPE: DNA
<213> ORGANISM: Homo sapiens
<220> FEATURE:
<221> NAME/KEY: misc_feature
<222> LOCATION: (356)..(356)
<223> OTHER INFORMATION: "n" is A, C, G, or T

<400> SEQUENCE: 23
tttaaaacaa ttacagagaa aactttattt tgggccattt aggaggttta gatcattttg       60
atcatcttca gctgtcttct cttcacatac aggaaaggcc ttggaaagca gtcgttgcgc      120
cagacagccc agggaagagc ggcacgctga ggacctaggg ccacctgctg ttccctggga      180
ttcatgtcct tctggggagg agggaggacc caggacaatg gctgctgttc atgatctgga      240
gatggagagc atgaatctga atatggggag agagatgaaa gaagctgga aggaagagga       300 gaaaatgaga gaggatgggg gaggtaaaga tcgggccaag agtaaaaagg tccacn         356

<210> SEQ ID NO 24
<211> LENGTH: 524
<212> TYPE: DNA
<213> ORGANISM: Homo sapiens

<400> SEQUENCE: 24
gggtctccgg tgtcttttgc agctcacatt gcaggtggat ttgctggaat gtccattggc       60
tacacggtgt ttagctgctt tgataaagca ctgatgaaag atccaaggtt ttggatagca      120
attgctgcat atttagcttg tgtcttattt gctgtgtttt tcaacatttt cctatctcca      180
gcaaactgac ctgccctat tgtaagtcaa ttaataaaaa gagccatctg gaggaaataa       240 aaaaaaagg aagactctat gaagaaacag agaagtctca gcaaaggcta acaattttat       300
atagaggaca aaacagcatt aaactcatca gttgcaaaga ttgcctataa aaggaccttaa      360 ggatttaagg aaggggcttc ttaatgtaga aagggaagaa gaagagagaa aagaagggta      420
gtaaaaacta gagattgggg ccaggcgcag tggctcacgc ctgtaatccc agcactttgg      480
gaggctgagg cgggtgaaat cacctgaggt catgagttca agac                      524
```

<210> SEQ ID NO 25
<211> LENGTH: 428
<212> TYPE: DNA
<213> ORGANISM: Homo sapiens

<400> SEQUENCE: 25

```
ttttttttcc ctttctacat taagaagccc cttccttaaa tcctaaggtc cttttatagg      60
caatctttgc aactgatgag tttaatgctg ttttgtcctc tatataaaat tgttagcctt     120
ttctgagact tctctgtttc ttcatagagt cttcctttt  tttattattt cctccagatg     180
gctctttta  ttaattgact tacaataggg gcaggtcagt ttgctggaga taggaaaatg     240
ttgaaaaaca cagcaaataa gacacaagct aaatatgcag caattgctat ccaaaacctt     300
ggatctttca gcagtgcttt atcaaagcag ctaaacaccg tgtagccaat ggacattcca     360
gcaaatccac ctgcaatgtg agctgcaaaa gacaccttgg gagaaaagga gggaaaatgg     420
aaataagt                                                             428
```

<210> SEQ ID NO 26
<211> LENGTH: 271
<212> TYPE: DNA
<213> ORGANISM: Homo sapiens

<400> SEQUENCE: 26

```
ctcgaaactg tgaaaacaca gcaaataaga cacaagctaa atatgcagca attgctatcc      60
aaaaccttgg atctttcagc agtgctttat caaagcagct aaacaccgtg tagccaatgg     120
acattccagc aaatccacct gcaatgtgag ctgcaaaaga cacctgggag aaaggagggg     180
aaaatggaaa tcagtgaaga caatgctaat tgtgtatttc agttgcatct ctcttattca     240
aacacaaata ccgtcacagt taaacaagcg t                                   271
```

<210> SEQ ID NO 27
<211> LENGTH: 262
<212> TYPE: DNA
<213> ORGANISM: Homo sapiens

<400> SEQUENCE: 27

```
tgaaatacac agcaaataga cacaagctaa atatgcagca attgctatcc aaaagcttgg      60
atctttcagc agtgctttat caaagcagct aaacaccgtg tagcgcatgg acattccagc     120
aaatccacct gcaatgtgag ctgcaaaaga caccttggga gaaaaggagg gaaaatggaa     180
ataagtgaag acaatgctaa ttgtgtattt cagttgcatc tctcttattc aaacacaaat     240
accgtcacag ttaaacaagc gt                                             262
```

<210> SEQ ID NO 28
<211> LENGTH: 120
<212> TYPE: DNA
<213> ORGANISM: Homo sapiens

<400> SEQUENCE: 28

```
gctcggtccg aaactgttga aaacacagc  aaataagaca caacgctaaa tatgcagcaa      60
ttgctatcca aaaccttgga tctttcagca gtgctttatc aaagcagcta acaccgtgt      120
```

<210> SEQ ID NO 29
<211> LENGTH: 894
<212> TYPE: DNA
<213> ORGANISM: Homo sapiens

```
<400> SEQUENCE: 29
ctcatccacg ttacttgaag aactccctgg tttaccaccc acagctgcga gcacaggttt    60
ggcgctacct gacatacatc ttcatgcatg cagggtatag aacacctgga ctcaatgtgg   120
tgctgcagct gtggtggggg tgcccctgga gatggtgcat ggagccaccc gaattgggct   180
tgtctacgtg gccggtgttg tggcagggtc cttggcagtg tctagtggct gacatgaccg   240
ctccagtcgt gggctcttct ggagggtgt atgctctcgt ctctgcccat ctggccaaca    300
ttgtcatgaa ctggtcaggc atgaagtgcc agttcaagct gctgcggatg gctgtggccc   360
ttatctgtat gagcatggag cttgggcggg ccgtgtggcc ccgcttccac ccgtcggcta   420
tcccccgtgc cctcacccaa gctttgtggc gcacttgggt ggcgtggccg tgtgcatcac   480
cctggccgtg gtggtcctga ggaactacga gcagaggctc caggaccagt cactgtggtg   540
gatttttgtg gccatgtaca ccgtcttcgg gctgttcgct gtctctggaa catctttggc   600
tacacctgtt ggacttaaag ctgcgctccc ccctgaggct tgaggcccca gtccgcgagg   660
ggagggaaag caggacccca gggagcgcct ggaaggttct tcctcatcac aggttcagta   720
agcgggcaaa cacgcacaaa cactgcgcct gtattgtgtt atttggccac gggggcacct   780
ctgcgaaggg ctgcgggcga acacaagac aaacggacta acacaagaac aagggggcgaa   840 tcatcgcgcg ggagcacttg gaaagcaggt taaaacggga cacaaggaca cttt         894

<210> SEQ ID NO 30
<211> LENGTH: 344
<212> TYPE: DNA
<213> ORGANISM: Homo sapiens
<220> FEATURE:
<221> NAME/KEY: misc_feature
<222> LOCATION: (19)..(19)
<223> OTHER INFORMATION: "n" is A, C, G, or T
<221> NAME/KEY: misc_feature
<222> LOCATION: (49)..(49)
<223> OTHER INFORMATION: "n" is A, C, G, or T
<221> NAME/KEY: misc_feature
<222> LOCATION: (92)..(92)
<223> OTHER INFORMATION: "n" is A, C, G, or T
<221> NAME/KEY: misc_feature
<222> LOCATION: (130)..(130)
<223> OTHER INFORMATION: "n" is A, C, G, or T

<400> SEQUENCE: 30
cctccgccag atgcctttna gaaaagggtc tccactgtgt gtccaaatnt aaacacaaac    60
attacagtgg cccagagtct tctgtccttg tntgcccggc ctagctgagc tgatgatgag   120
aagaaacctn gcaggcgctc cctgtgggtg ctgcttttcc ctcccctccc cgaccttggg   180
cctccagccc tcaggggga ggcggcagct ttaagtccag cagggtgtag gcaaagatgt    240
tccagaagac agcgaacagc acgaagacgg tgtacatggc cacaaaaatc caccacagtg   300
actggtcctg gagcctctgc tcgtagttcc tcaggaccac cacg                    344

<210> SEQ ID NO 31
<211> LENGTH: 1140
<212> TYPE: DNA
<213> ORGANISM: Homo sapiens

<400> SEQUENCE: 31
atggcgtggc gaggctgggc gcagagaggc tggggctgcg gccaggcgtg gggtgcgtcg    60
gtgggcggcc gcagctgcga ggagctcact gcggtcctaa ccccgccgca gctcctcgga   120
cgcaggttta acttctttat tcaacaaaaa tgcggattca gaaaagcacc caggaaggtt   180
```

-continued

| | |
|---|---|
| gaacctcgaa gatcagaccc agggacaagt ggtgaagcat acaagagaag tgctttgatt | 240 |
| cctcctgtgg aagaaacagt cttttatcct tctccctatc ctataaggag tctcataaaa | 300 |
| cctttatttt ttactgttgg gtttacaggc tgtgcatttg gatcagctgc tatttggcaa | 360 |
| tatgaatcac tgaaatccag ggtccagagt tattttgatg gtataaaagc tgattggttg | 420 |
| gatagcataa gaccacaaaa agaaggagac ttcagaaagg agattaacaa gtggtggaat | 480 |
| aacctaagtg atggccagcg gactgtgaca ggtattatag ctgcaaatgt ccttgtattc | 540 |
| tgtttatgga gagtaccttc tctgcagcgg acaatgatca gatatttcac atcgaatcca | 600 |
| gcctcaaagg tcctttgttc tccaatgttg ctgtcaacat tcagtcactt ctccttattt | 660 |
| cacatggcag caaatatgta tgttttgtgg agcttctctt ccagcatagt gaacattctg | 720 |
| ggtcaagagc agttcatggc agtgtaccta tctgcaggtg ttatttccaa ttttgtcagt | 780 |
| tacctgggta agttgccac aggaagatat ggaccatcac ttggtgcatc tggtgccatc | 840 |
| atgacagtcc tcgcagctgt ctgcactaag atcccagaag ggaggcttgc cattattttc | 900 |
| cttccgatgt tcacgttcac agcagggaat gccctgaaag ccattatcgc catggataca | 960 |
| gcaggaatga tcctgggatg gaaattttt gatcatgcgg cacatcttgg gggagctctt | 1020 |
| tttggaatat ggtatgttac ttacggtcat gaactgattt ggaagaacag ggagccgcta | 1080 |
| gtgaaaatct ggcatgaaat aaggactaat ggccccaaaa aaggaggtgg ctctaagtaa | 1140 |

<210> SEQ ID NO 32
<211> LENGTH: 2964
<212> TYPE: DNA
<213> ORGANISM: Homo sapiens

<400> SEQUENCE: 32

| | |
|---|---|
| gactcggcgc gggcgccctc ccggccagcg gcggcagccc ctcctccccg gcgccctcag | 60 |
| gaccccccag agaccccggg cggcggcagc ctgccttgct ctgccaggaa ccatgagtga | 120 |
| ggcccgcagg gacagcacga gcagcctgca gcgcaagaag ccaccctggc taaagctgga | 180 |
| cattccctct gcggtgcccc tgacggcaga agagcccagc ttcctgcagc ccctgaggcg | 240 |
| acaggctttc ctgaggagtg tgagtatgcc agccgagaca gcccacatct cttcacccca | 300 |
| ccatgagctc cggcggccgg tgctgcaacg ccagacgtcc atcacacaga ccatccgcag | 360 |
| ggggaccgcc gactggtttg gagtgagcaa ggacagtgac agcacccaga aatggcagcg | 420 |
| caagagcatc cgtcactgca gccagcgcta cgggaagctg aagccccagg tcctccggga | 480 |
| gctggacctg cccagccagg acaacgtgtc gctgaccagc accgagacgc caccccccact | 540 |
| ctacgtgggg ccatgccagc tgggcatgca aaagatcata gacccctgg cccgtggccg | 600 |
| tgccttccgt gtggcagatg acactgcgga aggcctgagt gccccacaca ctcccgtcac | 660 |
| gccgggtgct gcctccctct gctccttctc cagctcccgc tcaggtttcc accggctccc | 720 |
| gcggcggcgc aagcgagagt cggtggccaa gatgagcttc cgggcggccg cagcgctgat | 780 |
| gaaaggccgc tccgttaggg atggcacctt tcgccgggca cagcgtcgaa gcttcactcc | 840 |
| agctagcttt ctggaggagg acacaactga tttccccgat gagctggaca catccttctt | 900 |
| tgcccgggaa ggtatcctcc atgaagagct gtccacatac ccggatgaag ttttcgagtc | 960 |
| cccatcggag gcagcgctaa aggactggga gaaggcaccg gagcaggcgg acctcaccgg | 1020 |
| cggggccctg gaccgcagcg agcttgagcg cagccacctg atgctgccct ggagcgagg | 1080 |
| ctggcggaag cagaaggagg gcgccgcagc cccgcagccc aaggtgcggc tccgacagga | 1140 |
| ggtggtgagc accgcggggc cgcgacgggg ccagcgtatc gcggtgccgg tgcgcaagct | 1200 |

-continued

```
cttcgcccgg gagaagcggc cgtatgggct gggcatggtg ggacggctca ccaaccgcac    1260
ctaccgcaag cgcatcgaca gcttcgtcaa gcgccagatc gaggacatgg acgaccacag    1320
gcccttcttc acctactggc ttaccttcgt gcactcgctc gtcgccatcc tagccgtgtg    1380
catctatggc atcgcgcccg tgggcttctc gcagcatgag acggtggact cggtgctgcg    1440
gaaccgcggg gtctacgaga acgtcaagta cgtgcagcag gagaacttct ggatcgggcc    1500
cagctcggag gccctcatcc acctgggcgc caagttttcg ccctgcatgc gccaggaccc    1560
gcaggtgcac agcttcattc gctcggcgcg cgagcgcgag aagcactccg cctgctgcgt    1620
gcgcaacgac aggtcgggct gcgtgcagac ctcggaggag gagtgctcgt ccacgctggc    1680
agtgtgggtg aagtggccca tccatcccag cgccccagag cttgcgggcc acaagagaca    1740
gtttggctct gtctgccacc aggatcccag ggtgtgtgat gagccctcct ccgaagaccc    1800
tcatgagtgg ccagaagaca tcaccaagtg gccgatctgc accaaaaaca gcgctgggaa    1860
ccacaccaac catccccaca tggactgtgt catcacagga cggccctgct gcattggcac    1920
caagggcagg tgtgagatca cctcccggga gtactgtgac ttcatgaggg gctacttcca    1980
tgaggaggcc acgctctgct ctcaggtgca ctgcatggat gatgtgtgtg ggctcctgcc    2040
ttttctcaac cccgaggtgc ctgaccagtt ctaccgcctg tggctatccc tcttcctgca    2100
cgccgggatc ttgcactgcc tggtgtccat ctgcttccag atgactgtcc tgcgggacct    2160
ggagaagctg gcaggctggc accgcatagc catcatctac ctgctgagtg gtgtcaccgg    2220
caacctggcc agtgccatct cctgccata ccgagcagga gtgggtcctg ctggctccca    2280
gttcggcatc ctggcctgcc tcttcgtgga gctcttccag agctggcaga tcctggcgcg    2340
gccctggcgt gccttcttca gctgctggc tgtggtgctc ttcctcttca cctttgggct    2400
gctgccgtgg attgacaact tgcccacat ctcggggttc atcagtggcc tcttcctctc    2460
cttcgccttc ttgccctaca tcagctttgg caagttcgac ctgtaccgga acgctgcca    2520 gatcatcatc tttcaggtgg tcttcctggg cctcctggct ggcctggtgg tcctcttcta    2580
cgtctatcct gtccgctgtg agtggtgtga gttcctcacc tgcatcccct tcactgacaa    2640
gttctgtgag aagtacgaac tggacgctca gctccactga gctggctgcg ggctccagcg    2700
gccgtgtgct ccagcaggcc agagccgac acgacctccc tgagcctcac aggcttacag    2760
gagtcacctg ctccatgtgg ggactggcct gtttcctgaa cacagacctc tttcttgtgc    2820
cttgttcact tctgttgaac ccctcgtact gccgggcatt tattatacta cttcctgtca    2880
taaccttcta acttgtttct tgacgaccac ctcatgtggc caataaatga actgggagcg    2940
ttttaaaaaa aaaaaaaaaa aaaa    2964
```

<210> SEQ ID NO 33
<211> LENGTH: 2643
<212> TYPE: DNA
<213> ORGANISM: Homo sapiens

<400> SEQUENCE: 33

```
gctactccca cctgccacgc cgcaagagaa tgtctgtggc ccacatgagc ttgcaagctg      60
ccgctgccct cctcaagggg cgctcggtgc tggatgccac cggacagcgg tgccgggtgg     120
tcaagcgcag ctttgccttc ccgagcttcc tggaggagga tgtggtcgat ggggcagaca     180
cgtttgactc ctccttttt agtaaggaag aaatgagctc catgcctgat gatgtctttg     240
agtccccccc actctctgcc agctacttcc gagggatccc acactcagcc tcccctgtct     300
```

-continued

```
ccccgatgg ggtgcaaatc cctctgaagg agtatggccg agccccagtc cccgggcccc      360
ggcgcggcaa gcgcatcgcc tccaaggtga agcactttgc ctttgatcgg aagaagcggc      420
actacggcct cggcgtggtg ggcaactggc tgaaccgcag ctaccgccgc agcatcagca      480
gcactgtgca gcggcagctg agagcttcg acagccaccg gccctacttc acctactggc       540
tgaccttcgt ccatgtcatc atcacgctgc tggtgatttg cacgtatggc atcgcacccg      600
tgggctttgc ccagcacgtc accacccagc tggtgctgcg aacaaaggt gtgtacgaga       660 gcgtgaagta catccagcag gagaacttct ggttggccc cagctcgatt gacctgatcc       720 acctggggc caagttctca ccctgcatcc ggaaggacgg gcagatcgag cagctggtgc       780
tgcgcgagcg agacctggag cgggactcag gctgctgtgt ccagaatgac cactccggat      840
gcatccagac ccagcggaag gactgctcgg agactttggc cacttttgtc aagtggcagg      900
atgacactgg gccccccatg acaagtctg atctgggcca agcggact tcggggggctg       960 tctgccacca ggaccccagg acctgcgagg agccagcctc cagcggtgcc cacatctggc     1020
ccgatgacat cactaagtgg ccgatctgca cagagcaggc caggagcaac cacacaggct     1080
tcctgcacat ggactgcgag atcaagggcc gcccctgctg catcggcacc aagggcagct     1140
gtgagatcac caccgggaa tactgtgagt tcatgcacgg ctatttccat gaggaagcaa      1200
cactctgctc ccaggtgcac tgcttggaca aggtgtgtgg gctgctgccc ttcctcaacc     1260
ctgaggtccc agatcagttc tacaggctct ggctgtctct cttcctacat gctggcgtgg     1320
tgcactgcct cgtgtctgtg gtctttcaaa tgaccatcct gagggacctg agaagctgg      1380 ccggctggca ccgtatcgcc atcatcttca tcctcagtgg catcacaggc aacctcgcca     1440
gtgccatctt tctcccatac cgggcagagg tgggcccggc cggctcacag ttcggcctcc     1500
tcgcctgcct cttcgtggag ctcttccaga gctggccgct gctggagagg ccctggaagg     1560
ccttcctcaa cctctcggcc atcgtgctct tcctgttcat ctgtggcctc ttgccctgga     1620
tcgacaacat cgcccacatc ttcggcttcc tcagtggcct gctgctggcc ttcgccttcc     1680
tgccctacat caccttcggc accagcgaca agtaccgcaa gcgggcactc atcctggtgt     1740
cactgctggc ctttgccggc ctcttcgccg ccctcgtgct gtggctgtac atctaccca     1800 ttaactggcc ctggatcgag cacctcacct gcttccccctt caccagccgc ttctgcgaga     1860
agtatgagct ggaccaggtg ctgcactgac cgctgggcca cacggctgcc cctcagccct     1920
gctggaacag gtctgcctg cgagggctgc cctctgcaga gcgctctctg tgtgccagag     1980
agccagagac ccaagacagg gcccgggctc tggacctggg tgcccccctg ccaggcgagg     2040
ctgactccgc gtgagatggt tggttaaggc ggggttttc tggggcgtga ggcctgtgag     2100
atcctgaccc aagctcaggc acacccaagg cacctgcctc tctgagtctt gggtctcagt     2160
tcctaatatc ccgctccttg ctgagaccat ctcctggggc agggtccttt tcttcccagg     2220
tcctcagcgc tgcctctgct ggtgccttct ccccactac tactggagcg tgcccttgct      2280
ggggacgtgg ctgtgccctc agttgccccc agggctgggt gcccaccatg ccccttcctc     2340
tttctcctcc tacctctgcc ctgtgagccc atccataagg ctctcagatg ggacattgta     2400
ggaaaggctt tggccatggt ctgggggcag agaacaaggg gggagacaca agtagacctc     2460
aggtagaacg acaccgggcg gagccacccc agggcctgct cccagggagt gctcgaggcg     2520
catcaggccc gtttttttacc agtttatatc acggtcttca ttttttaaaag taacgctaac     2580 tttgtacgga cgatgtctca tggattaaat aatattcttt atggcaaaaa aaaaaaaaa     2640 aaa                                                                   2643
```

<210> SEQ ID NO 34
<211> LENGTH: 1305
<212> TYPE: DNA
<213> ORGANISM: Homo sapiens

<400> SEQUENCE: 34

```
atgggggcggg gcctctggga ggcgtggcct ccggccggct cctctgctgt tgccaaggga      60
aactgccgcg aggaggcgga aggagcagag gaccggcagc cggcgtcgag gcggggcgcg     120
ggaacgacgg cggccatggc ggcctcgggg cccgggtgtc gcagctggtg cttgtgtccc     180
gaggtgccat ccgccacctt cttcactgcg ctgctctcgc tgctggtttc cgggcctcgc     240
ctgttcctgc tgcagcagcc cctggcgccc tcgggcctca cgctgaagtc cgaggccctt     300
cgcaactggc aagtttacag gctggtaacc tacatctttg tctacgagaa tcccatctcc     360
ctgctctgcg cgctatcat catctggcgc tttgctggca atttcgagag aaccgtgggc     420
accgtccgcc actgcttctt caccgtgatc ttcgccatct tctccgctat catcttcctg     480
tcattcgagg ctgtgtcatc actgtcaaag ctgggggaag tggaggatgc agaggtttc      540
acccccagtgg cctttgccat gctgggagtc accaccgtcc gttctcggat gaggcgggcc     600
ctggtgtttg gcatggttgt gccctcagtc ctggttccgt ggctcctgct gggtgcctcg     660
tggctcattc cccagacctc tttcctcagt aatgtctgcg ggctgtccat cgggctggcc     720
tatgctcacc tactgctatt ccatcgacct ctcagagcga gtggcgctga agctcgatca     780
gaccttcccc ttcagcctga tgaggaggat atccgtgttc aagtacgtct cagggtcttc     840
agccgagagg agggcagccc agagccggaa actgaacccg gtgcctggct cctaccccac     900
acagagctgc caccctcacc tgtccccaag ccaccctgtg tcccagacgc agcacgccag     960
tggtcagaag ctggcctcct ggcctcctgc accccgggc acatgcccac cttgcctccg    1020
taccagcctg cctccggcct gtgctatgtg cagaaccact ttggtccaaa ccccaccctcc    1080
tccagtgtct acccagcttc tgcgggcacc tccctgggca tccagccccc cacgcctgtg    1140
aacagccctg gcacggtgta ttctggggcc ttgggacacc aggggctgca ggctccaagg    1200
agtcctccag ggtccccatg ccctgagaga atttctaggg aagtcatctc acttggcctt    1260
ctgaaggtcc tccctaagag tctcctgaca aaagttactt attga                    1305
```

<210> SEQ ID NO 35
<211> LENGTH: 1738
<212> TYPE: DNA
<213> ORGANISM: Homo sapiens

<400> SEQUENCE: 35

```
tgctgactaa tccgcgggcc gcggggaatg ggtggcgcgc cagccggtcg gcagggtca      60
cgcggccggg tgtgcgcgga atggattcag ggttctcggg tcgcgcccgg gagctagagt     120
cctgactccc agccggggtc cccgaccggc ctttcgggt gccgggcgc gctctgcaaa      180
ggggaaactg aggcccaagg aaattgagta tctctgcaaa gtcaccagct gagttcgaac     240
cagacagatc ctgggacccc ctactctatc cgccaccgga agaatctccg tccttgtctt     300
tccattctgc cctcccggct tcccagtaag cacacagccc caggaccacc cttgaccgtc     360
ctcaaccaag cgatgcatgc caggggcccc catgccaac tgtccccagc actgcctctg     420
gcctcctcag tcctgatgct gctgatgagc accctgtggc tggtgggggc cggccccggc     480
ctggtcctgg ccccggagct gttgctggac ccctggcagg tgcaccggct gctgacccat     540
```

```
gccctgggcc acacggccct gccaggcctg ctcctgagcc tgctgctcct gcccactgtg      600
ggctggcagc aggagtgcca cctgggcacg ctgagattcc tgcatgcctc agccctgctc      660
gccctggctt ctgggctgct ggcagtgctg ctggcaggcc ttgggctgtc cagtgcagcc      720
ggcagctgtg gatacatgcc tgtccacctg gccatgctgg ctggggaggg acaccgccct      780
agacggcccc gtggggcact gccaccgtgg ctgtcgccgt ggctgctgct gccctgacc       840 ccactgctca gctctgagcc acccttcctg cagctccttt gcggcctcct tgccggcctg      900
gcctatgcag ctgggccctt ccggtggctg aaccctcag agcgacggct gcaggtgctg       960
caggagggcg tcttgtgcag gaccttggcg gggtgctggc ccctgaggct ccttgccacc     1020
ccgggtagcc tggcggagct gcctgtcacc catcctgccg gagtgaggcc tcccatccct     1080
ggaccgcctt atgtggcctc ccctgacctc tggtcccact gggaagactc agccctgccc     1140
ccaccaagcc tgaggcctgt gcagcccacc tgggagggct cctcagaggc aggcctggac     1200
tgggctgggg ccagcttctc cccagggact ccgatgtggg cggccttgga tgagcagatg     1260
ctgcaggagg gcatccaggc ctcgcttctt gacgggccag cccaggaacc ccagagcgca     1320
ccatggctgt ccaagtcctc tgtctcctct ctgcggctgc agcagctgga gcgcatgggc     1380
ttccctacgg agcaggcggt ggtggcactg gcagccacag gccgtgtgga gggtgccgtg     1440
tcactgttgg ttggaggaca agtgggcact gagaccctgg tgacccatgg aaagggtggg     1500
cctgcccact ccgagggtcc tgggcctccc tagcccaggc agagagtggg gcacaggcag     1560
gcccttgggt gctaagggct gggctgcatg tgggtagccc gagctcctac tctgtctaaa     1620
gagggccaca gtggggagca ggggcacctc tggaggcagg agaggccccc cagcatgctg     1680
ccctagtacg tgtttagaat aaaaaccagt ttgttttttca acctggacct ccttggag       1738

<210> SEQ ID NO 36
<211> LENGTH: 438
<212> TYPE: PRT
<213> ORGANISM: Homo sapiens

<400> SEQUENCE: 36

Met Gly Arg Val Glu Asp Gly Gly Thr Thr Glu Glu Leu Glu Asp Trp
1               5                   10                  15

Asp Pro Gly Thr Ser Ala Leu Pro Ala Pro Gly Ile Lys Gln Gly Pro
            20                  25                  30

Arg Glu Gln Thr Gly Thr Gly Pro Leu Ser Gln Lys Cys Trp Glu Pro
        35                  40                  45

Glu Pro Asp Ala Pro Ser Gln Pro Gly Pro Ala Leu Trp Ser Arg Gly
    50                  55                  60

Arg Ala Arg Thr Gln Ala Leu Ala Gly Gly Ser Ser Leu Gln Gln Leu
65                  70                  75                  80

Asp Pro Glu Asn Thr Gly Phe Ile Gly Ala Asp Thr Phe Thr Gly Leu
                85                  90                  95

Val His Ser His Glu Leu Pro Leu Asp Pro Ala Lys Leu Asp Met Leu
            100                 105                 110

Val Ala Leu Ala Gln Ser Asn Glu Gln Gly Gln Val Cys Tyr Gln Glu
        115                 120                 125

Leu Val Asp Leu Ile Ser Ser Lys Arg Ser Ser Phe Lys Arg Ala
    130                 135                 140

Ile Ala Asn Gly Gln Arg Ala Leu Pro Arg Asp Gly Leu Asp Glu
145                 150                 155                 160

Pro Gly Leu Gly Val Tyr Lys Arg Phe Val Arg Tyr Val Ala Tyr Glu
```

-continued

```
                165                 170                 175
Ile Leu Pro Cys Glu Val Asp Arg Arg Trp Tyr Phe Tyr Arg His Arg
            180                 185                 190
Ser Cys Pro Pro Val Phe Met Ala Ser Val Thr Leu Ala Gln Ile
        195                 200                 205
Ile Val Phe Leu Cys Tyr Gly Ala Arg Leu Asn Lys Trp Val Leu Gln
    210                 215                 220
Thr Tyr His Pro Glu Tyr Met Lys Ser Pro Leu Val Tyr His Pro Gly
225                 230                 235                 240
His Arg Ala Arg Ala Trp Arg Phe Leu Thr Tyr Met Phe Met His Val
                245                 250                 255
Gly Leu Glu Gln Leu Gly Phe Asn Ala Leu Leu Gln Leu Met Ile Gly
            260                 265                 270
Val Pro Leu Glu Met Val His Gly Leu Leu Arg Ile Ser Leu Leu Tyr
        275                 280                 285
Leu Ala Gly Val Leu Ala Gly Ser Leu Thr Val Ser Ile Thr Asp Met
    290                 295                 300
Arg Ala Pro Val Val Gly Gly Ser Gly Gly Val Tyr Ala Leu Cys Ser
305                 310                 315                 320
Ala His Leu Ala Asn Val Val Met Asn Trp Ala Gly Met Arg Cys Pro
                325                 330                 335
Tyr Lys Leu Leu Arg Met Val Leu Ala Leu Val Cys Met Ser Ser Glu
            340                 345                 350
Val Gly Arg Ala Val Trp Leu Arg Phe Ser Pro Pro Leu Pro Ala Ser
        355                 360                 365
Gly Pro Gln Pro Ser Phe Met Ala His Leu Ala Gly Ala Val Val Gly
    370                 375                 380
Val Ser Met Gly Leu Thr Ile Leu Arg Ser Tyr Glu Glu Arg Leu Arg
385                 390                 395                 400
Asp Gln Cys Gly Trp Trp Val Val Leu Leu Ala Tyr Gly Thr Phe Leu
                405                 410                 415
Leu Phe Ala Val Phe Trp Asn Val Phe Ala Tyr Asp Leu Leu Gly Ala
            420                 425                 430
His Ile Pro Pro Pro
        435

<210> SEQ ID NO 37
<211> LENGTH: 292
<212> TYPE: PRT
<213> ORGANISM: Homo sapiens

<400> SEQUENCE: 37

Met Asn Leu Asn Met Gly Arg Glu Met Lys Glu Glu Leu Glu Glu Glu
1               5                   10                  15
Glu Lys Met Arg Glu Asp Gly Gly Lys Asp Arg Ala Lys Ser Lys
            20                  25                  30
Lys Val His Arg Ile Val Ser Lys Trp Met Leu Pro Glu Lys Ser Arg
        35                  40                  45
Gly Thr Tyr Leu Glu Arg Ala Asn Cys Phe Pro Pro Val Phe Ile
    50                  55                  60
Ile Ser Ile Ser Leu Ala Glu Leu Ala Val Phe Ile Tyr Tyr Ala Val
65                  70                  75                  80
Trp Lys Pro Gln Lys Gln Trp Ile Thr Leu Asp Thr Gly Ile Leu Glu
                85                  90                  95
```

-continued

```
Ser Pro Phe Ile Tyr Ser Pro Glu Lys Arg Glu Ala Trp Arg Phe
            100                 105                 110
Ile Ser Tyr Met Leu Val His Ala Gly Val Gln His Ile Leu Gly Asn
        115                 120                 125
Leu Cys Met Gln Leu Val Leu Gly Ile Pro Leu Glu Met Val His Lys
130                 135                 140
Gly Leu Arg Val Gly Leu Val Tyr Leu Ala Gly Val Ile Ala Gly Ser
145                 150                 155                 160
Leu Ala Ser Ser Ile Phe Asp Pro Leu Arg Tyr Leu Val Gly Ala Ser
                165                 170                 175
Gly Gly Val Tyr Ala Leu Met Gly Gly Tyr Phe Met Asn Val Leu Val
            180                 185                 190
Asn Phe Gln Glu Met Ile Pro Ala Phe Gly Ile Phe Arg Leu Leu Ile
            195                 200                 205
Ile Ile Leu Ile Ile Val Leu Asp Met Gly Phe Ala Leu Tyr Arg Arg
        210                 215                 220
Phe Phe Val Pro Glu Asp Gly Ser Pro Val Ser Phe Ala Ala His Ile
225                 230                 235                 240
Ala Gly Gly Phe Ala Gly Met Ser Ile Gly Tyr Thr Val Phe Ser Cys
                245                 250                 255
Phe Asp Lys Ala Leu Leu Lys Asp Pro Arg Phe Trp Ile Ala Ile Ala
            260                 265                 270
Ala Tyr Leu Ala Cys Val Leu Phe Ala Val Phe Phe Asn Ile Phe Leu
            275                 280                 285
Ser Pro Ala Asn
    290
```

```
<210> SEQ ID NO 38
<211> LENGTH: 174
<212> TYPE: PRT
<213> ORGANISM: Homo sapiens

<400> SEQUENCE: 38
```

```
Leu Cys Arg Val Gln His Ile Leu Gly Asn Leu Cys Met Gln Leu Val
1               5                   10                  15
Leu Gly Ile Pro Leu Glu Met Val His Lys Gly Leu Arg Val Gly Leu
            20                  25                  30
Val Tyr Leu Ala Gly Val Ile Ala Gly Ser Leu Ala Ser Ser Ile Phe
        35                  40                  45
Asp Pro Leu Arg Tyr Leu Val Gly Ala Ser Gly Gly Val Tyr Ala Leu
    50                  55                  60
Met Gly Gly Tyr Phe Met Asn Val Leu Val Asn Phe Gln Glu Met Ile
65                  70                  75                  80
Pro Ala Phe Gly Ile Phe Arg Leu Leu Ile Ile Ile Leu Ile Ile Val
                85                  90                  95
Leu Asp Met Gly Phe Ala Leu Tyr Arg Arg Phe Val Pro Glu Asp
            100                 105                 110
Gly Ser Pro Val Ser Phe Ala Ala His Ile Ala Gly Gly Phe Ala Gly
        115                 120                 125
Met Ser Ile Gly Tyr Thr Val Phe Ser Cys Asp Lys Ala Leu Leu
    130                 135                 140
Lys Asp Pro Arg Phe Trp Ile Ala Ile Ala Ala Tyr Leu Ala Cys Val
145                 150                 155                 160
Leu Phe Ala Val Phe Phe Asn Ile Phe Leu Ser Pro Ala Asn
                165                 170
```

-continued

<210> SEQ ID NO 39
<211> LENGTH: 162
<212> TYPE: PRT
<213> ORGANISM: Homo sapiens

<400> SEQUENCE: 39

Met Gln Leu Val Leu Gly Ile Pro Leu Glu Met Val His Lys Gly Leu
1               5                   10                  15

Arg Val Gly Leu Val Tyr Leu Ala Gly Val Ile Ala Gly Ser Leu Ala
            20                  25                  30

Ser Ser Ile Phe Asp Pro Leu Arg Tyr Leu Val Gly Ala Ser Gly Gly
        35                  40                  45

Val Tyr Ala Leu Met Gly Gly Tyr Phe Met Asn Val Leu Val Asn Phe
    50                  55                  60

Gln Glu Met Ile Pro Ala Phe Gly Ile Phe Arg Leu Leu Ile Ile Ile
65                  70                  75                  80

Leu Ile Ile Val Leu Asp Met Gly Phe Ala Leu Tyr Arg Arg Phe Phe
                85                  90                  95

Val Pro Glu Asp Gly Ser Pro Val Ser Phe Ala Ala His Ile Ala Gly
            100                 105                 110

Gly Phe Ala Gly Met Ser Ile Gly Tyr Thr Val Phe Ser Cys Phe Asp
        115                 120                 125

Lys Ala Leu Leu Lys Asp Pro Arg Phe Trp Ile Ala Ile Ala Ala Tyr
    130                 135                 140

Leu Ala Cys Val Leu Phe Ala Val Phe Phe Asn Ile Phe Leu Ser Pro
145                 150                 155                 160

Ala Asn

<210> SEQ ID NO 40
<211> LENGTH: 379
<212> TYPE: PRT
<213> ORGANISM: Homo sapiens

<400> SEQUENCE: 40

Met Ala Trp Arg Gly Trp Ala Gln Arg Gly Trp Gly Cys Gly Gln Ala
1               5                   10                  15

Trp Gly Ala Ser Val Gly Gly Arg Ser Cys Glu Glu Leu Thr Ala Val
            20                  25                  30

Leu Thr Pro Pro Gln Leu Leu Gly Arg Arg Phe Asn Phe Phe Ile Gln
        35                  40                  45

Gln Lys Cys Gly Phe Arg Lys Ala Pro Arg Lys Val Glu Pro Arg Arg
    50                  55                  60

Ser Asp Pro Gly Thr Ser Gly Glu Ala Tyr Lys Arg Ser Ala Leu Ile
65                  70                  75                  80

Pro Pro Val Glu Glu Thr Val Phe Tyr Pro Ser Pro Tyr Pro Ile Arg
                85                  90                  95

Ser Leu Ile Lys Pro Leu Phe Phe Thr Val Gly Phe Thr Gly Cys Ala
            100                 105                 110

Phe Gly Ser Ala Ala Ile Trp Gln Tyr Glu Ser Leu Lys Ser Arg Val
        115                 120                 125

Gln Ser Tyr Phe Asp Gly Ile Lys Ala Asp Trp Leu Asp Ser Ile Arg
    130                 135                 140

Pro Gln Lys Glu Gly Asp Phe Arg Lys Glu Ile Asn Lys Trp Trp Asn
145                 150                 155                 160

```
Asn Leu Ser Asp Gly Gln Arg Thr Val Thr Gly Ile Ile Ala Ala Asn
                165                 170                 175
Val Leu Val Phe Cys Leu Trp Arg Val Pro Ser Leu Gln Arg Thr Met
            180                 185                 190
Ile Arg Tyr Phe Thr Ser Asn Pro Ala Ser Lys Val Leu Cys Ser Pro
        195                 200                 205
Met Leu Leu Ser Thr Phe Ser His Phe Ser Leu Phe His Met Ala Ala
    210                 215                 220
Asn Met Tyr Val Leu Trp Ser Phe Ser Ser Ile Val Asn Ile Leu
225                 230                 235                 240
Gly Gln Glu Gln Phe Met Ala Val Tyr Leu Ser Ala Gly Val Ile Ser
                245                 250                 255
Asn Phe Val Ser Tyr Leu Gly Lys Val Ala Thr Gly Arg Tyr Gly Pro
            260                 265                 270
Ser Leu Gly Ala Ser Gly Ala Ile Met Thr Val Leu Ala Ala Val Cys
        275                 280                 285
Thr Lys Ile Pro Glu Gly Arg Leu Ala Ile Ile Phe Leu Pro Met Phe
    290                 295                 300
Thr Phe Thr Ala Gly Asn Ala Leu Lys Ala Ile Ile Ala Met Asp Thr
305                 310                 315                 320
Ala Gly Met Ile Leu Gly Trp Lys Phe Phe Asp His Ala Ala His Leu
                325                 330                 335
Gly Gly Ala Leu Phe Gly Ile Trp Tyr Val Thr Tyr Gly His Glu Leu
            340                 345                 350
Ile Trp Lys Asn Arg Glu Pro Leu Val Lys Ile Trp His Glu Ile Arg
        355                 360                 365
Thr Asn Gly Pro Lys Lys Gly Gly Ser Lys
    370                 375

<210> SEQ ID NO 41
<211> LENGTH: 855
<212> TYPE: PRT
<213> ORGANISM: Homo sapiens

<400> SEQUENCE: 41

Met Ser Glu Ala Arg Arg Asp Ser Thr Ser Ser Leu Gln Arg Lys Lys
1               5                   10                  15
Pro Pro Trp Leu Lys Leu Asp Ile Pro Ser Ala Val Pro Leu Thr Ala
                20                  25                  30
Glu Glu Pro Ser Phe Leu Gln Pro Leu Arg Arg Gln Ala Phe Leu Arg
            35                  40                  45
Ser Val Ser Met Pro Ala Glu Thr Ala His Ile Ser Ser Pro His His
        50                  55                  60
Glu Leu Arg Arg Pro Val Leu Gln Arg Gln Thr Ser Ile Thr Gln Thr
65                  70                  75                  80
Ile Arg Arg Gly Thr Ala Asp Trp Phe Gly Val Ser Lys Asp Ser Asp
                85                  90                  95
Ser Thr Gln Lys Trp Gln Arg Lys Ser Ile Arg His Cys Ser Gln Arg
            100                 105                 110
Tyr Gly Lys Leu Lys Pro Gln Val Leu Arg Glu Leu Asp Leu Pro Ser
        115                 120                 125
Gln Asp Asn Val Ser Leu Thr Ser Thr Glu Thr Pro Pro Pro Leu Tyr
    130                 135                 140
Val Gly Pro Cys Gln Leu Gly Met Gln Lys Ile Ile Asp Pro Leu Ala
145                 150                 155                 160
```

```
Arg Gly Arg Ala Phe Arg Val Ala Asp Asp Thr Ala Glu Gly Leu Ser
                165                 170                 175
Ala Pro His Thr Pro Val Thr Pro Gly Ala Ala Ser Leu Cys Ser Phe
            180                 185                 190
Ser Ser Ser Arg Ser Gly Phe His Arg Leu Pro Arg Arg Lys Arg
        195                 200                 205
Glu Ser Val Ala Lys Met Ser Phe Arg Ala Ala Ala Leu Met Lys
    210                 215                 220
Gly Arg Ser Val Arg Asp Gly Thr Phe Arg Arg Ala Gln Arg Arg Ser
225                 230                 235                 240
Phe Thr Pro Ala Ser Phe Leu Glu Glu Asp Thr Thr Asp Phe Pro Asp
                245                 250                 255
Glu Leu Asp Thr Ser Phe Phe Ala Arg Glu Gly Ile Leu His Glu Glu
            260                 265                 270
Leu Ser Thr Tyr Pro Asp Glu Val Phe Glu Ser Pro Ser Glu Ala Ala
        275                 280                 285
Leu Lys Asp Trp Glu Lys Ala Pro Glu Gln Ala Asp Leu Thr Gly Gly
    290                 295                 300
Ala Leu Asp Arg Ser Glu Leu Glu Arg Ser His Leu Met Leu Pro Leu
305                 310                 315                 320
Glu Arg Gly Trp Arg Lys Gln Lys Glu Gly Ala Ala Pro Gln Pro
                325                 330                 335
Lys Val Arg Leu Arg Gln Glu Val Val Ser Thr Ala Gly Pro Arg Arg
            340                 345                 350
Gly Gln Arg Ile Ala Val Pro Val Arg Lys Leu Phe Ala Arg Glu Lys
        355                 360                 365
Arg Pro Tyr Gly Leu Gly Met Val Gly Arg Leu Thr Asn Arg Thr Tyr
    370                 375                 380
Arg Lys Arg Ile Asp Ser Phe Val Lys Arg Gln Ile Glu Asp Met Asp
385                 390                 395                 400
Asp His Arg Pro Phe Phe Thr Tyr Trp Leu Thr Phe Val His Ser Leu
                405                 410                 415
Val Ala Ile Leu Ala Val Cys Ile Tyr Gly Ile Ala Pro Val Gly Phe
            420                 425                 430
Ser Gln His Glu Thr Val Asp Ser Val Leu Arg Asn Arg Gly Val Tyr
        435                 440                 445
Glu Asn Val Lys Tyr Val Gln Gln Glu Asn Phe Trp Ile Gly Pro Ser
    450                 455                 460
Ser Glu Ala Leu Ile His Leu Gly Ala Lys Phe Ser Pro Cys Met Arg
465                 470                 475                 480
Gln Asp Pro Gln Val His Ser Phe Ile Arg Ser Ala Arg Glu Arg Glu
                485                 490                 495
Lys His Ser Ala Cys Cys Val Arg Asn Asp Arg Ser Gly Cys Val Gln
            500                 505                 510
Thr Ser Glu Glu Glu Cys Ser Ser Thr Leu Ala Val Trp Val Lys Trp
        515                 520                 525
Pro Ile His Pro Ser Ala Pro Glu Leu Ala Gly His Lys Arg Gln Phe
    530                 535                 540
Gly Ser Val Cys His Gln Asp Pro Arg Val Cys Asp Glu Pro Ser Ser
545                 550                 555                 560
Glu Asp Pro His Glu Trp Pro Glu Asp Ile Thr Lys Trp Pro Ile Cys
                565                 570                 575
```

```
Thr Lys Asn Ser Ala Gly Asn His Thr Asn His Pro His Met Asp Cys
                580                 585                 590

Val Ile Thr Gly Arg Pro Cys Cys Ile Gly Thr Lys Gly Arg Cys Glu
            595                 600                 605

Ile Thr Ser Arg Glu Tyr Cys Asp Phe Met Arg Gly Tyr Phe His Glu
        610                 615                 620

Glu Ala Thr Leu Cys Ser Gln Val His Cys Met Asp Asp Val Cys Gly
625                 630                 635                 640

Leu Leu Pro Phe Leu Asn Pro Glu Val Pro Asp Gln Phe Tyr Arg Leu
                645                 650                 655

Trp Leu Ser Leu Phe Leu His Ala Gly Ile Leu His Cys Leu Val Ser
            660                 665                 670

Ile Cys Phe Gln Met Thr Val Leu Arg Asp Leu Glu Lys Leu Ala Gly
        675                 680                 685

Trp His Arg Ile Ala Ile Ile Tyr Leu Leu Ser Gly Val Thr Gly Asn
    690                 695                 700

Leu Ala Ser Ala Ile Phe Leu Pro Tyr Arg Ala Glu Val Gly Pro Ala
705                 710                 715                 720

Gly Ser Gln Phe Gly Ile Leu Ala Cys Leu Phe Val Glu Leu Phe Gln
                725                 730                 735

Ser Trp Gln Ile Leu Ala Arg Pro Trp Arg Ala Phe Phe Lys Leu Leu
            740                 745                 750

Ala Val Val Leu Phe Leu Phe Thr Phe Gly Leu Leu Pro Trp Ile Asp
        755                 760                 765

Asn Phe Ala His Ile Ser Gly Phe Ile Ser Gly Leu Phe Leu Ser Phe
    770                 775                 780

Ala Phe Leu Pro Tyr Ile Ser Phe Gly Lys Phe Asp Leu Tyr Arg Lys
785                 790                 795                 800

Arg Cys Gln Ile Ile Ile Phe Gln Val Val Phe Leu Gly Leu Leu Ala
                805                 810                 815

Gly Leu Val Val Leu Phe Tyr Val Tyr Pro Val Arg Cys Glu Trp Cys
            820                 825                 830

Glu Phe Leu Thr Cys Ile Pro Phe Thr Asp Lys Phe Cys Glu Lys Tyr
        835                 840                 845

Glu Leu Asp Ala Gln Leu His
    850                 855

<210> SEQ ID NO 42
<211> LENGTH: 619
<212> TYPE: PRT
<213> ORGANISM: Homo sapiens

<400> SEQUENCE: 42

Met Ser Val Ala His Met Ser Leu Gln Ala Ala Ala Leu Leu Lys
1               5                   10                  15

Gly Arg Ser Val Leu Asp Ala Thr Gly Gln Arg Cys Arg Val Val Lys
                20                  25                  30

Arg Ser Phe Ala Phe Pro Ser Phe Leu Glu Glu Asp Val Val Asp Gly
            35                  40                  45

Ala Asp Thr Phe Asp Ser Ser Phe Ser Lys Glu Glu Met Ser Ser
        50                  55                  60

Met Pro Asp Asp Val Phe Glu Ser Pro Leu Ser Ala Ser Tyr Phe
65                  70                  75                  80

Arg Gly Ile Pro His Ser Ala Ser Pro Val Ser Pro Asp Gly Val Gln
                85                  90                  95
```

-continued

```
Ile Pro Leu Lys Glu Tyr Gly Arg Ala Pro Val Pro Gly Pro Arg Arg
            100                 105                 110
Gly Lys Arg Ile Ala Ser Lys Val Lys His Phe Ala Phe Asp Arg Lys
            115                 120                 125
Lys Arg His Tyr Gly Leu Gly Val Gly Asn Trp Leu Asn Arg Ser
            130                 135             140
Tyr Arg Arg Ser Ile Ser Ser Thr Val Gln Arg Gln Leu Glu Ser Phe
145                 150                 155                 160
Asp Ser His Arg Pro Tyr Phe Thr Tyr Trp Leu Thr Phe Val His Val
                165                 170                 175
Ile Ile Thr Leu Leu Val Ile Cys Thr Tyr Gly Ile Ala Pro Val Gly
                180                 185                 190
Phe Ala Gln His Val Thr Thr Gln Leu Val Leu Arg Asn Lys Gly Val
                195                 200                 205
Tyr Glu Ser Val Lys Tyr Ile Gln Gln Glu Asn Phe Trp Val Gly Pro
            210                 215                 220
Ser Ser Ile Asp Leu Ile His Leu Gly Ala Lys Phe Ser Pro Cys Ile
225                 230                 235                 240
Arg Lys Asp Gly Gln Ile Glu Gln Leu Val Leu Arg Glu Arg Asp Leu
                245                 250                 255
Glu Arg Asp Ser Gly Cys Cys Val Gln Asn Asp His Ser Gly Cys Ile
                260                 265                 270
Gln Thr Gln Arg Lys Asp Cys Ser Glu Thr Leu Ala Thr Phe Val Lys
            275                 280                 285
Trp Gln Asp Asp Thr Gly Pro Pro Met Asp Lys Ser Asp Leu Gly Gln
            290                 295                 300
Lys Arg Thr Ser Gly Ala Val Cys His Gln Asp Pro Arg Thr Cys Glu
305                 310                 315                 320
Glu Pro Ala Ser Ser Gly Ala His Ile Trp Pro Asp Asp Ile Thr Lys
                325                 330                 335
Trp Pro Ile Cys Thr Glu Gln Ala Arg Ser Asn His Thr Gly Phe Leu
                340                 345                 350
His Met Asp Cys Glu Ile Lys Gly Arg Pro Cys Cys Ile Gly Thr Lys
            355                 360                 365
Gly Ser Cys Glu Ile Thr Thr Arg Glu Tyr Cys Glu Phe Met His Gly
            370                 375                 380
Tyr Phe His Glu Glu Ala Thr Leu Cys Ser Gln Val His Cys Leu Asp
385                 390                 395                 400
Lys Val Cys Gly Leu Leu Pro Phe Leu Asn Pro Glu Val Pro Asp Gln
                405                 410                 415
Phe Tyr Arg Leu Trp Leu Ser Leu Phe Leu His Ala Gly Val Val His
                420                 425                 430
Cys Leu Val Ser Val Val Phe Gln Met Thr Ile Leu Arg Asp Leu Glu
            435                 440                 445
Lys Leu Ala Gly Trp His Arg Ile Ala Ile Phe Ile Leu Ser Gly
450                 455                 460
Ile Thr Gly Asn Leu Ala Ser Ala Ile Phe Leu Pro Tyr Arg Ala Glu
465                 470                 475                 480
Val Gly Pro Ala Gly Ser Gln Phe Gly Leu Leu Ala Cys Leu Phe Val
                485                 490                 495
Glu Leu Phe Gln Ser Trp Pro Leu Leu Glu Arg Pro Trp Lys Ala Phe
            500                 505                 510
```

-continued

```
Leu Asn Leu Ser Ala Ile Val Leu Phe Leu Phe Ile Cys Gly Leu Leu
            515                 520                 525

Pro Trp Ile Asp Asn Ile Ala His Ile Phe Gly Phe Leu Ser Gly Leu
        530                 535                 540

Leu Leu Ala Phe Ala Phe Leu Pro Tyr Ile Thr Phe Gly Thr Ser Asp
545                 550                 555                 560

Lys Tyr Arg Lys Arg Ala Leu Ile Leu Val Ser Leu Leu Ala Phe Ala
                565                 570                 575

Gly Leu Phe Ala Ala Leu Val Leu Trp Leu Tyr Ile Tyr Pro Ile Asn
            580                 585                 590

Trp Pro Trp Ile Glu His Leu Thr Cys Phe Pro Phe Thr Ser Arg Phe
        595                 600                 605

Cys Glu Lys Tyr Glu Leu Asp Gln Val Leu His
610                 615

<210> SEQ ID NO 43
<211> LENGTH: 434
<212> TYPE: PRT
<213> ORGANISM: Homo sapiens

<400> SEQUENCE: 43

Met Gly Arg Gly Leu Trp Glu Ala Trp Pro Ala Gly Ser Ser Ala
1               5                   10                  15

Val Ala Lys Gly Asn Cys Arg Glu Glu Ala Gly Ala Glu Asp Arg
                20                  25                  30

Gln Pro Ala Ser Arg Arg Gly Ala Gly Thr Thr Ala Ala Met Ala Ala
            35                  40                  45

Ser Gly Pro Gly Cys Arg Ser Trp Cys Leu Cys Pro Glu Val Pro Ser
        50                  55                  60

Ala Thr Phe Phe Thr Ala Leu Leu Ser Leu Leu Val Ser Gly Pro Arg
65                  70                  75                  80

Leu Phe Leu Leu Gln Gln Pro Leu Ala Pro Ser Gly Leu Thr Leu Lys
                85                  90                  95

Ser Glu Ala Leu Arg Asn Trp Gln Val Tyr Arg Leu Val Thr Tyr Ile
            100                 105                 110

Phe Val Tyr Glu Asn Pro Ile Ser Leu Leu Cys Gly Ala Ile Ile Ile
        115                 120                 125

Trp Arg Phe Ala Gly Asn Phe Glu Arg Thr Val Gly Thr Val Arg His
    130                 135                 140

Cys Phe Phe Thr Val Ile Phe Ala Ile Phe Ser Ala Ile Ile Phe Leu
145                 150                 155                 160

Ser Phe Glu Ala Val Ser Ser Leu Ser Lys Leu Gly Glu Val Glu Asp
                165                 170                 175

Ala Arg Gly Phe Thr Pro Val Ala Phe Ala Met Leu Gly Val Thr Thr
            180                 185                 190

Val Arg Ser Arg Met Arg Arg Ala Leu Val Phe Gly Met Val Val Pro
        195                 200                 205

Ser Val Leu Val Pro Trp Leu Leu Leu Gly Ala Ser Trp Leu Ile Pro
    210                 215                 220

Gln Thr Ser Phe Leu Ser Asn Val Cys Gly Leu Ser Ile Gly Leu Ala
225                 230                 235                 240

Tyr Ala His Leu Leu Leu Phe His Arg Pro Leu Arg Ala Ser Gly Ala
                245                 250                 255

Glu Ala Arg Ser Asp Leu Pro Leu Gln Pro Asp Glu Glu Asp Ile Arg
            260                 265                 270
```

-continued

```
Val Gln Val Arg Leu Arg Val Phe Ser Arg Glu Glu Gly Ser Pro Glu
            275                 280                 285
Pro Glu Thr Glu Pro Gly Ala Trp Leu Leu Pro His Thr Glu Leu Pro
        290                 295                 300
Pro Ser Pro Val Pro Lys Pro Pro Cys Val Pro Asp Ala Ala Arg Gln
305                 310                 315                 320
Trp Ser Glu Ala Gly Leu Leu Ala Ser Cys Thr Pro Gly His Met Pro
                325                 330                 335
Thr Leu Pro Pro Tyr Gln Pro Ala Ser Gly Leu Cys Tyr Val Gln Asn
            340                 345                 350
His Phe Gly Pro Asn Pro Thr Ser Ser Val Tyr Pro Ala Ser Ala
        355                 360                 365
Gly Thr Ser Leu Gly Ile Gln Pro Pro Thr Pro Val Asn Ser Pro Gly
            370                 375                 380
Thr Val Tyr Ser Gly Ala Leu Gly His Gln Gly Leu Gln Ala Pro Arg
385                 390                 395                 400
Ser Pro Pro Gly Ser Pro Cys Pro Glu Arg Ile Ser Arg Glu Val Ile
                405                 410                 415
Ser Leu Gly Leu Leu Lys Val Leu Pro Lys Ser Leu Leu Thr Lys Val
            420                 425                 430
Thr Tyr

<210> SEQ ID NO 44
<211> LENGTH: 386
<212> TYPE: PRT
<213> ORGANISM: Homo sapiens

<400> SEQUENCE: 44

Met His Ala Arg Gly Pro His Gly Gln Leu Ser Pro Ala Leu Pro Leu
1               5                   10                  15
Ala Ser Ser Val Leu Met Leu Leu Met Ser Thr Leu Trp Leu Val Gly
            20                  25                  30
Ala Gly Pro Gly Leu Val Leu Ala Pro Glu Leu Leu Leu Asp Pro Trp
        35                  40                  45
Gln Val His Arg Leu Leu Thr His Ala Leu Gly His Thr Ala Leu Pro
    50                  55                  60
Gly Leu Leu Leu Ser Leu Leu Leu Pro Thr Val Gly Trp Gln Gln
65                  70                  75                  80
Glu Cys His Leu Gly Thr Leu Arg Phe Leu His Ala Ser Ala Leu Leu
                85                  90                  95
Ala Leu Ala Ser Gly Leu Leu Ala Val Leu Leu Ala Gly Leu Gly Leu
            100                 105                 110
Ser Ser Ala Ala Gly Ser Cys Gly Tyr Met Pro Val His Leu Ala Met
        115                 120                 125
Leu Ala Gly Glu Gly His Arg Pro Arg Pro Arg Gly Ala Leu Pro
    130                 135                 140
Pro Trp Leu Ser Pro Trp Leu Leu Ala Leu Thr Pro Leu Leu Ser
145                 150                 155                 160
Ser Glu Pro Pro Phe Leu Gln Leu Leu Cys Gly Leu Leu Ala Gly Leu
                165                 170                 175
Ala Tyr Ala Ala Gly Ala Phe Arg Trp Leu Glu Pro Ser Glu Arg Arg
            180                 185                 190
Leu Gln Val Leu Gln Glu Gly Val Leu Cys Arg Thr Leu Ala Gly Cys
        195                 200                 205
```

```
Trp Pro Leu Arg Leu Leu Ala Thr Pro Gly Ser Leu Ala Glu Leu Pro
    210                 215                 220
Val Thr His Pro Ala Gly Val Arg Pro Ile Pro Gly Pro Pro Tyr
225                 230                 235                 240
Val Ala Ser Pro Asp Leu Trp Ser His Trp Glu Asp Ser Ala Leu Pro
                245                 250                 255
Pro Pro Ser Leu Arg Pro Val Gln Pro Thr Trp Glu Gly Ser Ser Glu
            260                 265                 270
Ala Gly Leu Asp Trp Ala Gly Ala Ser Phe Ser Pro Gly Thr Pro Met
        275                 280                 285
Trp Ala Ala Leu Asp Glu Gln Met Leu Gln Glu Gly Ile Gln Ala Ser
    290                 295                 300
Leu Leu Asp Gly Pro Ala Gln Glu Pro Gln Ser Ala Pro Trp Leu Ser
305                 310                 315                 320
Lys Ser Ser Val Ser Ser Leu Arg Leu Gln Gln Leu Glu Arg Met Gly
                325                 330                 335
Phe Pro Thr Glu Gln Ala Val Val Ala Leu Ala Ala Thr Gly Arg Val
            340                 345                 350
Glu Gly Ala Val Ser Leu Leu Val Gly Gly Gln Val Gly Thr Glu Thr
        355                 360                 365
Leu Val Thr His Gly Lys Gly Gly Pro Ala His Ser Glu Gly Pro Gly
    370                 375                 380
Pro Pro
385

<210> SEQ ID NO 45
<211> LENGTH: 1413
<212> TYPE: DNA
<213> ORGANISM: Mus musculus

<400> SEQUENCE: 45
atggcctact gggagaagct tctgccgcac gtggtgcaag agctggacgc aggcagtggt      60
tctgggtcga gctgttcggt gggggacgat ctacccaggc agtgcgtcga gttggggccg     120
cgcgtgcgcg tgcaggatat gcgcgtactc tggctgtgtg cgcgctgggc tggcatctcg     180
gtgacgctgt ctgagctcgg ggagcgcaga gcagagcagg cggagcgggc cggccggggc     240
ggagcggagc ggtccgcaga gcagcccctc ccggcctcgg ccgaccccgg ccctcggccc     300
ggctctatgg acaggagctc gctgctgcag ctcattcagg agcagcagct ggatcctgag     360
aacacaggct tcatcggtgc ggacaccttc gctggtctgg tacacagcca tgagctgccc     420
ctggacccca ccaagttgga catgttggtg gctctggctc agagcaacga gcggggccag     480
gtctgctacc aggagctggt ggacctggtc agtgccatga tcagcagcaa gcgttccagc     540
agcttcaaga gagccattgc taacggacag cgggcactgc cccgagacgg actgctagat     600
gagccaggcc tgagtgtcta caagcggttt gtgcgctatg tggcctacga gatcctgccc     660
tgcgaggtgg accgccgctg gtacttctac aggcaccgca cctgcccacc cctgtgttc      720
atggcctcgg tcactcttgc ccagtgtccc cagatcatcg tgttcctgtg ctacggggca     780
cgtctcaaca gtgggtgct ccagacctac cacctgaat atatgaagag ccctctggtg      840
tatcacccag acaccgtgc tcgggcatgg cgcttcctca cctacatgtt catgcatgtc      900
gggctggagc agctagggtt caatgccctc ctgcagctga tgatcggtgt gccctggag     960
atggtacatg gcgtgcttcg catcagcctg ctctacctgg cgggcgtgct ggcaggctcc    1020
```

-continued

```
ctgactgtct ctatcacaga tatgcgtgcc cccgtggtag ggggctctgg aggggtctat    1080
gccctgtgct cagcacacct ggccaatgtt gtcatggtaa tgggactgcc tttctgggga    1140
gtgagttccg aagtgggccg ggctgtgtgg ctacgcttct ccccaccact gcctgcctca    1200
ggcccacagc ccagcttcat ggcacacctg gctggtgcag tggtaggtgt aagcatgggc    1260
cttaccatcc ttcggagcta tgaggaacgc ctgagggacc agtgcggctg gtgggtggtg    1320
ctacttgcct atggcacctt cctgcttttc gccatcttct ggaacgtctt tgcctatgac    1380
ctgctgggtg ccgatatccc ccctccacct tga                                 1413
```

<210> SEQ ID NO 46
<211> LENGTH: 470
<212> TYPE: PRT
<213> ORGANISM: Mus musculus

<400> SEQUENCE: 46

```
Met Ala Tyr Trp Glu Lys Leu Leu Pro His Val Gln Glu Leu Asp
 1               5                  10                  15

Ala Gly Ser Gly Ser Ser Ser Cys Ser Val Gly Asp Asp Leu Pro
                20                  25                  30

Arg Gln Cys Val Glu Leu Gly Pro Arg Val Arg Val Gln Asp Met Arg
                35                  40                  45

Val Leu Trp Leu Cys Ala Arg Trp Ala Gly Ile Ser Val Thr Leu Ser
 50                  55                  60

Glu Leu Gly Glu Arg Arg Ala Glu Gln Ala Glu Arg Ala Gly Arg Gly
 65                  70                  75                  80

Gly Ala Glu Arg Ser Ala Glu Gln Pro Leu Pro Ala Ser Ala Asp Pro
                85                  90                  95

Gly Pro Arg Pro Gly Ser Met Asp Arg Ser Ser Leu Leu Gln Leu Ile
                100                 105                 110

Gln Glu Gln Gln Leu Asp Pro Glu Asn Thr Gly Phe Ile Gly Ala Asp
                115                 120                 125

Thr Phe Ala Gly Leu Val His Ser His Glu Leu Pro Leu Asp Pro Thr
 130                 135                 140

Lys Leu Asp Met Leu Val Ala Leu Ala Gln Ser Asn Glu Arg Gly Gln
 145                 150                 155                 160

Val Cys Tyr Gln Glu Leu Val Asp Leu Val Ser Ala Met Ile Ser Ser
                165                 170                 175

Lys Arg Ser Ser Ser Phe Lys Arg Ala Ile Ala Asn Gly Gln Arg Ala
                180                 185                 190

Leu Pro Arg Asp Gly Leu Leu Asp Glu Pro Gly Leu Ser Val Tyr Lys
                195                 200                 205

Arg Phe Val Arg Tyr Val Ala Tyr Glu Ile Leu Pro Cys Glu Val Asp
                210                 215                 220

Arg Arg Trp Tyr Phe Tyr Arg His Arg Thr Cys Pro Pro Val Phe
 225                 230                 235                 240

Met Ala Ser Val Thr Leu Ala Gln Cys Pro Gln Ile Ile Val Phe Leu
                245                 250                 255

Cys Tyr Gly Ala Arg Leu Asn Lys Trp Val Leu Gln Thr Tyr His Pro
                260                 265                 270

Glu Tyr Met Lys Ser Pro Leu Val Tyr His Pro Gly His Arg Ala Arg
                275                 280                 285

Ala Trp Arg Phe Leu Thr Tyr Met Phe Met His Val Gly Leu Glu Gln
                290                 295                 300
```

```
Leu Gly Phe Asn Ala Leu Leu Gln Leu Met Ile Gly Val Pro Leu Glu
305                 310                 315                 320

Met Val His Gly Val Leu Arg Ile Ser Leu Leu Tyr Leu Ala Gly Val
            325                 330                 335

Leu Ala Gly Ser Leu Thr Val Ser Ile Thr Asp Met Arg Ala Pro Val
            340                 345                 350

Val Gly Gly Ser Gly Gly Val Tyr Ala Leu Cys Ser Ala His Leu Ala
            355                 360                 365

Asn Val Val Met Val Met Gly Leu Pro Phe Trp Gly Val Ser Ser Glu
            370                 375                 380

Val Gly Arg Ala Val Trp Leu Arg Phe Ser Pro Pro Leu Pro Ala Ser
385                 390                 395                 400

Gly Pro Gln Pro Ser Phe Met Ala His Leu Ala Gly Ala Val Val Gly
                405                 410                 415

Val Ser Met Gly Leu Thr Ile Leu Arg Ser Tyr Glu Glu Arg Leu Arg
            420                 425                 430

Asp Gln Cys Gly Trp Trp Val Val Leu Leu Ala Tyr Gly Thr Phe Leu
            435                 440                 445

Leu Phe Ala Ile Phe Trp Asn Val Phe Ala Tyr Asp Leu Leu Gly Ala
            450                 455                 460

Asp Ile Pro Pro Pro Pro
465                 470

<210> SEQ ID NO 47
<211> LENGTH: 34319
<212> TYPE: DNA
<213> ORGANISM: Mus musculus
<220> FEATURE:
<221> NAME/KEY: misc_feature
<222> LOCATION: (34274)..(34275)
<223> OTHER INFORMATION: "n" is A, C, G, or T
<221> NAME/KEY: misc_feature
<222> LOCATION: (34285)..(34285)
<223> OTHER INFORMATION: "n" is A, C, G, or T
<221> NAME/KEY: misc_feature
<222> LOCATION: (34297)..(34298)
<223> OTHER INFORMATION: "n" is A, C, G, or T
<221> NAME/KEY: misc_feature
<222> LOCATION: (34301)..(34301)
<223> OTHER INFORMATION: "n" is A, C, G, or T

<400> SEQUENCE: 47
actagtcctg caggtttaaa cgaattcgcc ctttccctcc tgagcctgcc ctcacccttg      60
tccagtgttc agccaagcac ttgaggaata tctcagagct gttctactat gcccagaagg     120
ctgttctgca tcccacagcc ccctttatg accctgaggc caaacaggta agtagtggat      180
gagggccaca cacctatttc tcgaaggccc atccatgtgg gccttggata aggagtacaa     240
gtaaatacgc gtaccgacag ggtggccagg aaaagggcca cttggtgttg tgtccctgca    300
gctcaggcct gcatgcgccc aggcgctcac acgcatcttc aggctgtcgg accaggaccg    360
agaccacggg ctgagcgacg aggaactcaa tgccttccag gtgtggtcct gccctgacac    420
cctagctgcc cttgtgagag ggtcatcagg atagctgact gatctgaagc actctcttac    480
cggaggcaga agtcctgctt tggccatccc ctggccccac aggccctgga ggatgtgaag    540
agggtggtgt gcaagaacgt gtcaggtggt gtgcagaatg accggctgac cctggaaggt    600
gaggcagaca tcaccttata tcctgatgtg tggggagtgg caaggcggtg tactaacctt    660
ccaccttccc acaggcttcc tcttcctgaa cacactcttc atccagcgtg gccggcacga    720
gaccacgtgg accatcctgc ggcgctttgg ttacagtgac tcactggagc taacgcccga    780
```

-continued

```
ctacctctat ccagcgtgag ttgtaggctg gtgggcagtg gtgcttatcc tcttggggtc      840
aatccttgtg gcctggggac tttagcttgg tctctgagca cacactcatt agctcccccc      900
ttgcttagcc ccaaccgtgt aaccagaggt tctgttggga gtgcctgact gcccaggcac      960
ttttaactgt cacaggtgac agtaaccctg ccttgtgaca gttaaagtgc atccccacag     1020
gctccatgtc cccctggct gcagcacaga gctcaaccat cgtggctacc agtttgtgca      1080
gcggatgttc gagaagcatg accaggtaag cacgtcacct cacgccttga caccccctccc    1140 cgcaaagaaa cttgtcacca tagccccttt gcctgtagga ccatgatggt gtcctctcgc     1200
ccacggaact acagaatctc ttcagtgtgt tctcaggtgc tccatggggc cctgaactct     1260
tacacacagt ccccactcag gctggctgtc tgcctttgca tggctatctc tgccagtgga     1320
cgtaagtaca gtccctgtct acctgtctgt ccctacccat cccatcttcc actctcctta    1380
gccctgtacc ctcctctact cccagcctca tgacctactt ggatgtccag caatgccttg    1440
cacaccttgg ctacctgggt taccctaccc tctgtgaaca ggactctcag gcacaggcta    1500
tcacaggtag gtgaccactt ttttggtccc tgggcccagc caaacccttc ttgatggcca    1560
acaccctcac gtgagcgcac cttttcagtt acccgcgaga agaagctgga ccaggagaaa    1620
gggcagacac agcgcagcgt tctcatgtgt aaggtgctgg gagcccgagg agtgggcaag    1680
tcagccttct tgcaagcctt ccttggcaac agccttgggg tgagaattat ggaggcccca    1740
gcccctacct gggaactcaa gggggcagag gggtgccaca gagaactctg ggccaaaaa     1800 ctcttcctgc tgtccacaca ggaagccagg gaccccctg agaaattccc cctgcatacc     1860
atcaatacag tgcgggtcaa cgggcaggag aagtacctga ttgtgagtga gggcctgtgc    1920
accatgtcct gaagggtata cctgtgacac ccatataccc atatattctt cctcctaatg    1980
gagctgtctc agggtggccc ttgagggatc cagctgtggg gaggccacta aagctactgt    2040
ttgtcccagc tgtgtgaagt gaatgctgac agcctgctgg acacctctct agacactacc    2100
tgtgatgtcg cctgcttaat gtttgacagc agtgatccca agacctttgt acactgtgct    2160
accatataca aggcaagccc tgacttgagg tcctgtgggg ggatcccagc catagcccag    2220
ttagccagca agctcagctc tcgaatgttt cttttttcct ggcagcgtta ttacatggat    2280
gggcagaccc cctgcctctt tattgcctcc aaagctgatc tccctgaagg tgttgccccc    2340
ccagggctgt cacccgctga gttctgccgg aggcaccggc tgcctgcccc agcttcattc    2400
tcctgcttgg gacccgcaat gcccagcaca gatgtctta cccaacttgc taccatggcc     2460
actttcccgt gagtataccg cagcctcaat gtgggtgggg cttagtctgt ctgggtacaa    2520
aggtgtcaga gctgtagacc cgtggcctgt ggcccagaga gctatgctgg atggcctctg    2580
gcttggcctc cgcctgcctg ggacgggttt tcagcagtga gcttttcgca agcacacgtc    2640
ttgagtatta ttcttttccac agacacctgg tgcacacaga gctgcacccc acctccttct    2700
ggctccgagg agtgctggtg gctgtcggca cggctgtggc tgctgtcctt agcttctcac    2760
tatacagggt cctagtgaag agccgatgac aaaggaccca tgagcctctc ctgccccag     2820 gcacagcaca ctgtggtgcc ttatgtgggc ccacacggca aagaagtatg ggctttcggc    2880
ctgttggagt aatatctgtg tggctggcta cagggtccct gggactgatg tgggttcctg    2940
ctcaggaact tggtatttag atcttggctt ccaaaagtct gttgccctat tccaggcctg    3000
tcctgctgag cctgagagta ctggtgccag gtgtgaggcc ttagccttgg agggaggggag   3060 gattgtgtgt aaggggctgg gctgtgggta aggaatccag tgaccaggac ccgaagttct    3120
```

```
cagggtgtgt tcccccccct tcctggttgt gcatggccag tggacatgta gagggcaaga      3180
ggtagtggtc aaatcaggga gggacccgat agtcacagag gtcccacctt tttgtcaggt      3240
gtggagcctt atccacactg cgccagctgc agagcaagcg gaactgactt tcctgattaa      3300
atttcacttg tcttttccat ctcttggatt ttgatctctc aatgcaactt actttctctc      3360
tttctctccc tcccttcctt ccttcctttc tccttcttc ctttcttctt tctttctttc       3420
tttctttctt tctttctttc tttctttctt tcaaaaatat gcttattttt atgagtttga      3480
gtgttttgcc tgcccatata tgtaagtgcc ccgtgtgtgt gcctggtacc gacagaagcc      3540
aaatgagtat gtcagagttc cctggaactg gagttaacta atgattgtga gccatcccgt      3600
gggtgttgga aacaaaccca ggtcctctgc agaggcagca agtgctctga accaccaagt      3660
cctctctcca gccccataaa aaatggcttt tcaatcgcaa tgtgactgct gttttgtgt       3720
gagttggaaa tgccacctga cccttctgag acgtctcccc tgtgtcctgg ttcccattct      3780
gtggtctcac tagtcatgct gattaatggc tacggaaggt ccagttaagg ggtctgctgt      3840
ctagtaatgc cagcatccat cagtgtcatg ggggtggggg tgtgtgtgag agggctcctg      3900
ctgcttctct gggaacattg cttctgctgt tggttcttca ttgccccaca ctccacacag      3960
cccaggcagc ctgcctggct ctgctgagaa cctgggcttt atgtgtagcc tggctgttac      4020
aagcaagggc cagccataga tctcaacctg gccagaagct gagtgaatga tggactcgga      4080
gttgatcctg tgacatgacc tcctaccacc aaagacaccc aaacaggaat ccatacactc      4140
aacgagtcac ttgggttggg tcaggtgggt tctctctgcc ccagaatgtc cacagaacag      4200
ggatccctga aaaatgaggc ctttgcctcc tgctccagtc ccaacctact ggcctgccgt      4260
cccactgagc atctaggcag gctgcttatt gtaggcagct gtattccctg tagaggccca      4320
tcgggcaaga ataactgcca tcccatcttt gcagtagcag attgttttga atgatacttg      4380
gggggggttgc catggttaca catcctattg gtctgtcacc ttcactgtcc tcaggagcac      4440
acccctccc ttatccaagc tgcagtcagt tctaccttca cgtggctatt tgtggctctt       4500
cctggctatc ccctgtgcct tcttgactgg tgttttgca ctggaggccc tgctatctca       4560
aatccaattc agggatgttt ggttagagct tccagccttg gccatgaata gggaacctgg      4620
ggcttcgttg ctggaacagt gcaaataagg acaagtgtgt ctactgaaag cagctccagc      4680
tcaggagaaa gtatgatggg agcaactgga ccttgacatt ctggggatgg gtcacagacc      4740
tattttagt agaaagaaag tatcctaggg aaggtaataa aacaggctgc ctaagagggt       4800
attgggtgct gcaggctgcc agctatggcc tactgggaga agcttctgcc gcacgtggtg      4860
caagagctgg acgcaggcag tggttctggg tcgagctgtt cggtggggga cgatctaccc      4920
aggcagtgcg tcgagttggg gccgcgcgtg cgcgtgcagg atatgcgcgt actctggctg      4980
tgtgcgcgct gggctggcat ctcggtgacg ctgtctgagc tcggggagcg cagagcagag      5040
caggcggagc gggccggccg gggcggagcg gagcggtccg cagagcagcc cctcccggcc      5100
tcggccgacc ccggccctcg gcccggctct atggacagga gctcgctgct gcagctcatt      5160
caggagcagg tgcgtggtgg gtgggagctg gcactgcctt ggcgcccttc cagccggtga      5220
ggggttcggg ggagggacca tgctcgcaga aggcccaggc agccgcctcc caaaccccc       5280
tccctgcacg accttggtct ctgagactcc cgaccccaag aaaggtctgg cttcatcggg      5340
tttccacgga aagctgggga tggagggtgg tggtccttgg acctaggtcc ttccccttc       5400
taggactggt agagcgaata tgaggtggta gaacagccaa accaggcacc ttgccctgcc      5460
agggcctggg aacaagctgg ttctagcaaa caggcactga ctggcacaaa ggtccagcct      5520
```

-continued

```
tcctagccag cctagctcag ccctgtggct gggagttggc ccaccctcta ctcccccacc      5580
acagcagctg gatcctgaga acacaggctt catcggtgcg gacaccttcg ctggtctggt      5640
acacagccat gagctgcccc tggaccccac caagttggac atgttggtgg ctctggctca      5700
gagcaacgag cggggccagg tctgctacca ggagctggtg gacctggtca gtgccatggt      5760
gtgtgggcag caggggaggg cccaggcctg gtcaagcgca gcaccctgac caaagctggg      5820
tgggcacaca gcttttact  gggtagggct tacagacctg ggcagtgtgg aagaccctca      5880
gaccattagc agccacacag ccaagtaagg tagggttcca caggaacaat actgtcacct      5940
acactaaggt tcctgccctt cagatcagca gcaagcgttc cagcagcttc aagagagcca      6000
ttgctaacgg acagcgggca ctgccccgag acggactgct agatgagcca ggcctgagtg      6060
tctacaagcg gtttgtgcgc tatgtggcct acgagatcct gccctgcgag gtggaccgcc      6120
gctggtactt ctacaggcac cgcacctgcc accccctgt  gttcatggcc tcggtcactc      6180
ttgcccaggt gggcctgcct acacattgcc ctggggcctc ctgagtccct agtcttgacc      6240
agccctaaca ctagtgtccc cagatcatcg tgttcctgtg ctacggggca cgtctcaaca      6300
agtgggtgct ccagacctac caccctgaat atatgaagag ccctctggtg tatcacccag      6360
gacaccgtgc tcgggcatgg cgcttcctca cctacatgtt catgcatgtc gggtaagtga      6420
gccttgcctt ccagagcctc ttctccactc ctaccccag  cacctgccca ctgactctga      6480
aggcttatct cccagctaag ttacactgcc tgaggtggtc tggagtaggc agggtaccca      6540
tctgaccacc tctgccatgc tcttctgtgg ccaggctgga gcagctaggg ttcaatgccc      6600
tcctgcagct gatgatcggt gtgccctgg  agatggtaca tggcgtgctt cgcatcagcc      6660
tgctctacct ggcgggcgtg ctggcaggtg agactggcat ataggtgggt gggtcccctg      6720
cctacctcac ctgctgaggg gagggccagc tgtgccctca cctctccctt gcccacagg      6780 ctccctgact gtctctatca cagatatgcg tgccccgtg  gtaggggct  ctggaggggt      6840 ctatgccctg tgctcagcac acctggccaa tgttgtcatg gtaatgggac tgcctttctg      6900
gggaggtggg aagggcccca ttggacatgc ttcacagcct gtctgcctgc ccccatcaga      6960
actgggctgg gatgcggtgt ccatacaagc tgctgaggat ggtgctggct ctggtgtgca      7020
gtgagtagtg gggcaggtgg ggcgctggga ggccctttac ctgcagacag ggcccctccc      7080
acctgttgct ccctctgcag tgagttccga agtgggccgg gctgtgtggc tacgcttctc      7140
cccaccactg cctgcctcag gcccacagcc cagcttcatg gcacacctgg ctggtgcagt      7200
ggtaggtgta agcatgggcc ttaccatcct tcggagctat gaggaacgcc tgagggacca      7260
gtgcggctgg tgggtggtgc tacttgccta tggcaccttc ctgcttttcg ccatcttctg      7320
gaacgtcttt gcctatgacc tgctgggtgc cgatatcccc cctccacctt gacctgctcc      7380
ctagggccat gtggctagag ccaggcacca ggtgggcctg catgtctgcc ctatatgaat      7440
ggacctctcg gctgcttttc cccacagggg cagggggcc  ctgtgatccc caccccag       7500 ctgaagccaa gtcttactgc agcccttgct gcaccccccc ccccaggct  ttccaggggg      7560 agggtgtta  ctgggccagg gctgggtgga ggaccttgag cgtggcccta gaggagaccc      7620
cttccctccc cactgacccc aggacttgca gtctgagcct ttttggagaa tgaataaata      7680
ttttacacag caccaggtag ctgtcctggg gctctgcagg cttgtctgcc ccctcaccca      7740
agctgtatga gacacctccc ctccaggacg gtctgtgctc cctctctccc ttcaagctct      7800
gcacctgact tgaggtggta gctttactcc tggccatggc cggaatccac aggaggtggg      7860
```

-continued

```
gccccctggga agaaactgtg gacttccagg tcagtccaag ttcagcaatc gtttattgtg      7920
ctacaagagc ttccaatctc ctgttctttc agcctcccct tccaaacgcaa gcccacaaca      7980
gagctaggtt cacttggcct gggtcctgta attcttggca ggtccttgtg ggaggcccag       8040
tcagggtgaa ggtcaggcag caggtctggg catacatctg ccccccaagt ttgcacaaga      8100
cgaaagagtct acaactctaa gacactcact agtgaggtcc acaagggttc tggggtcaag    8160
ttactaacca ccagaaccat gatggggccc tggatgacct ctcaggcccc gctcagcccc      8220
gctcagaaag gcagtgaact cttgcacctg ggctagaaac agcaagtagt gcttgagtgt      8280
gtactggagg gttagcaagc taggaactgt agccaccgcc tcttcgtata tgaaagctgc      8340
aaccccagaa acctctgcct ccaggaccac tgcaaagagt gacaaggagg ttctggggat      8400
agctttttt gagctcctag agcccccacc caacttgggc aaagatgcta cctactcact      8460
cgaggcagtg gcagaaacca cgcagcgaag tttgactgcg gcgcccagat cagcagaaag     8520
ccgagttctg cttctccaag tccggggttg ggggtgttag cggccaacag ctgatgcagc      8580
agcggctaga aatgcctcaa cgacagacca tggggtcaaa gggtcttggt gcaggcgctc      8640
tccaaggaaa ccagccggct ccgcccttga agaagctcct cccatgacc gcgagaaggg       8700
caagagtcca gccgtgcacc cgcagctact tctatagcaa ccgcagaagg tccttcggtg     8760
tcagcgtgtc acgtgcttgt ttctcagcca ttaatggccg caggcagctc ctcccgattc      8820
ccgaggaagc ccctcgagag cggtctgatc tgcgggcctc tcttctaccc tcaattccgc      8880
cttcctaccg gcggtccaga cgttcccagg ctgtcgcgtg agcccgtgtg tgccctggtg      8940
gtgcgctagg acccgggcct agtgaccggc cctcggaagg ccacttctca atgaccgctg      9000
ccacgttcgc ccagcttggg gccggagggc ggggcttgag cgccgatggg cggagccttg     9060
gtctgagcag ggtaggtctc ggttactgta gggcggggcc tgtagagcgc ggcggaagct     9120
tctcagagct aagggaactg gctcaatcca cgaggctccg cctttgctca cgtgtccccca   9180
tgccagctcc gccccacacc ggaagttccg gtggcggatc gccgaccggg cggagctgat    9240
cgctgcgcgg gctgcgagat ctaggtggcc gggcgcggag cccaagccgt gccgcgcggc    9300
gccatgaagg gcaaggagga aaaggagggc ggcgcgcggc tgggcactgg tggcggcggc     9360
agccctgata agagcccgag tgcgcaagag ctcaaggagc agggaaaccg gctcttcgtg     9420
ggccgcaagt acccggaggc ggcggcctgc tacggccgcg ccatcgtgag tgcgggaggg    9480
gcgggggcgg ggcccgatgt gcctcccagt tttgtgatcc cggacagggt ttctggcagc    9540
ctggactcga tggctcgctc gctcccctgg tgcccggatt gctgttcccg agtctagggc     9600
tgatttgact gggaactggc gggcgggatg cttgattaag taagactaag gatgacacca   9660
ggagctcttg ccccttgaga tttccaagcc cagagcttgt agaggggttg tgggatttct     9720
ctcaaaagca gttggaggca agaaagcatg ccagaatcc agagctcttg ataattcgga     9780
aatctccagt tcctctattc cagccatggg cccccaaagc tggagcattg accagatcat     9840
tggctttcag cttgctaaat gagaggggat caactgagcc cacactcttt gacgcctggt     9900
cttggtcccc agactcggaa cccacttgtg gcagtgtact acactaaccg ggccctgtgc     9960
tatctgaaga tgcagcagcc tgaacaggca cttgctgact gccggcgagc cctggagctg    10020
gacgggcagt ctgtgaaggc gcacttcttc ctggggcagt gccagctgga gatggagagt    10080
tatgatgagg ccattgccaa tctgcagcga ggtgggctga caagatgcaa ggttgagggc    10140
accttggggg accaggattg ttgacaagtg taaccaaaag tgtccactcc cctagcctat    10200
agtttggcca aggagcagcg actcaacttt ggggatgata ttcctagtgc ccttcgcatt    10260
```

-continued

```
gctaagaaga agcgctggaa cagtatcgag gaacggcgca tccaccagga gagtgagctg    10320
cattcatatc tcaccaggct cattgctgct gagcgagaga ggtgggtccc tcccccagca    10380
gacactgagt caccagcaca agtgttttta ttgaaggaca caaccggta catgggaagc     10440 ccaggaggaa agaggcctga gatggggcgg gctctgtgat ttcctggtca gggccatcac    10500
caactagctt ctggttaacc ctcagggaac tggaggagtg tcagcggaac cacgagggtc    10560
atgaagatga tggccacatc cgggcccagc aggcctgcat tgaggccaag cacgtgaggg    10620
tgcccctagt ccacatgtgg gtcattgtgt gtgtgtttgt gtgtggcatg aaaagtgccc    10680
cagcctttgg tggatctgtt ggcccatgca tgacatgagt gccctggtgg acagagtgtg    10740
tgtgtctgtg tggagacagg agttgcccac acatggcact caactctgca ggataaatac    10800
atggcagata tggatgagct cttctctcag gtggacgaga aaagaaaggt gaggaccccc    10860
ggaagctcat cggctgctgc tggtatggtg accccacag  ccccctccag ttctagacat    10920
tttccccttg tgctatagaa gcgagatatc cctgactact tgtgtggcaa gattagcttt    10980
gagctgatgc gggaaccctg cattacaccc agtggtatca cctatgaccg caaggacatt    11040
gaggagcacc tgcaggtaag gagggcccat ggagaccggg ccatggagag ccttggtacc    11100
cggatcggta tactcaggcc attgaacact cttgactctg ttgcagcgtg tgggccactt    11160
tgaccctgtg acccggagcc ctctgaccca ggaacagctc atccccaact tggccatgaa    11220
ggaagtcatt gacgctttca tctctgagaa cggctgggta gaggactatt gaggccccat    11280
gtcctgcctg gcaccctggc ccaggaggat ctggagacgg aagctccagt ccctgtatag    11340
tttgtgtccc tgggcctgcc cccatcggcc ctgctgatgg gttctgaact gctcccctcc    11400
tcagcatacc ccttgctgga ccatgagcct cccttgtccc ccttctgggc tggagagtgg    11460
gtgagggtgg gctgaggttg ctgctgctgc cactgtcctg taataaagtc tgtgagcact    11520
acattggcat gtgctggtgc agtgggcttg ccagttgcct gtctggctag ccaaggaagg    11580
tagaaatgaa gacactggtg tccagattga gtgtggcatg ccaccaccga tcaggaaaat    11640
acagtacctg ggagaaaaga aaaaaaaat  tttgattcat ggcttttttga gttagcccaa    11700 cccccaccta ccagctactg acttcaccag cctggatggt acattctaga ggccgtgctg    11760
acagggctag agatgggtat atttccagca gccaggccaa tgtggtcttg ttagggtgga    11820
actcaggtgt cttctcagga gggtagagga accagcgctg gaggcaggag tgtaaggtca    11880
ctatgtgtgc aatggactat agacaccaga tttacacaca cacataacac acacataaca    11940
ctgtactgac cttccgacca tagataacct ctgagaaacc aggcccatgc cagtggaagg    12000
gtaccccaga tccagctcct gtggggtcag ttatgaatag ctgatgaaca aaatatatat    12060
gggctccccc aagtttgttt tgaagtagcc cctacctgca attccaaagc tgtaagcagg    12120
ggtggttccc aggagacgga atggtggcgg agagtagtgc tggaagaggg atgcccactc    12180
agtgaagttg ttgtctccaa aaaagtacag ggtgtctgcc agcagagagg gtgataggca    12240
ggagtactgg caacagtggg ctcccaagta ccccactccc accgctgcct gggtctggct    12300
caccattgcc tagggatgca ggatcctggg gctgcagcag ctgttccaca tattcctgga    12360
agggcaggtc cactacaaga aggggagccc agtcgggact ggtcagttct gcctttgaga    12420
tgtgaaggca aaccttgcag ggtgtgtagc tcacctttct ggtaggagta ggtgttggct    12480
gtactcaagc gaacaatgtt gtccccgaac gaggctagca ggttttcccg ggaacacagg    12540 gccccggaact tctggggatg aaggataagg taactgagca cttggccaaa cagaagcagt    12600
```

-continued

```
tgcccacagg gtacgaatac tcaccgagtt gtccgtgagt ccttgcaaga tgacgggctt    12660
gaggaaggca tagctggggg gaaagaggag aatgttgcac tgagtttgaa ctctgcaggg    12720
gcctctccta cacaccaggc agtgagacct ccgcagccaa agaccatgat tggtagtatg    12780
cctagaatca tgctgagact tggggcaggc acacatactg ctgcatgaat tcggagtacg    12840
tgatgtgtgc ccgacgctcc actgtgcaac gctcctcctc cattactgct gctgcaattc    12900
ccagcccatt ctgtttcctg cagggacaac aggtcaggcc agtcaaagct ttaagttcag    12960
gctccctccc gccacccatt tcctatggct caccatcccc cttcgccaga ggcaggcaga    13020
atcacagtca ccatcatcca tagtacaaag agcaaaagca gaccgcgccg cccagccgcc    13080
gccatgaaca tacgggtgca ggcgcgcagc acgctgggaa ttctgtcgac acttgcgtaa    13140
ccacaagcca ttggcttatc atccggactg ctgtagctac ctgcaagcag tagccagccg    13200
gccttggaag tctcctcctt cttcatacaa gcgcattgta cacacacaca cacacacaca    13260
cacacatcca cacaacatcc ctatttaatc atttcctcaa ggcggaggga aaattgtatc    13320
gagcagccat tgactactgt gcgttaccat ggctacagcg cccctaccgg aagttcccat    13380
gtgctagaaa gttcccaccc aaggcgcaat gaaagtgaca agtggccaaa cagcagctct    13440 ggattttat tgggttaaaa agttgtagcc accttccatc ctggtacaca ggatgggtaa    13500
ggggctgtga gcctagtccg gtggacatcg ggatcgagct gaggacgctg catcagcctt    13560
agggaaggcc aggtcaggag tattcacaga ggtggccgca gcctgcaggg cagtgggagc    13620
tgccttccag ccatttcatg atgtgctgaa gatggccacc atgactgcaa ccctgacacc    13680
acacgaacag gcctttaacc acatgatggc agacagcaca catgctggca cagcggtggc    13740
acctgggaat ggggagggctg ttcagctggg gagctctggg ctgcctccct tccaacctcc    13800
ccaactgcac catcgcacct gtcacagacc cagccgcggc tgctcatggg ccgcttgcag    13860
tgactacagt tgacatgcag cgtggtggag gcttggttga ggcagctaac tgccctgctg    13920
gtgctcagct tcaccacctc attggacaca ttccagaggc agaagcgctg cagcagatct    13980
atgtaggatg tgtaccagtg ctcctggtgg ggagggacag gctcaggtta gtgtttccag    14040
gaacactagg gtgtgtgtgt gggggggggg gggggtacag tggaaaagaa acaggctcag    14100
atgagggaac cagcagccag tctggggaga ccctcccccct gccccgcccc gatccatcac    14160
acacctgggt ctgctcatcg atgtcctttc gcactctctc acccagcacg atgagaacag    14220
acacagccat ctgcacgtcg ccctgctcag cgtagaagcg caacatgtcc cgtaccaata    14280
cactgaagaa gtcaggtggc aggcggctgt catagagtgc atgtgagacg gagaggaggg    14340
aggaggagga gtccaccggg gctaatgaag ctgtgtctgc ctcattgccg ctcacgtgcg    14400
gagagtccgc cttgtcctgc agatgctcgg gcccagatgg tgtgtctaca atttcatggc    14460
gcagtgggaa ggcctcttgt ggcagcacat attcaggctc ctcggctggg aggcaggggt    14520
gaggaaagat ggacctgagt gtaggcttcc cgctccactc agctcctgct cacagagcca    14580
tgttctgggt tggacccctc tatagctgac ccagccccta ctcacagtgc acatgttctg    14640
tgtcaagtgg gtacagctca tcgtcctctc cttctacgtc acccagcagg tagtcagcag    14700
gcacatcact cccttctgtt tcctcattat ctgcccagca gggaagggag gtcattcagg    14760
gagtggcacc ccagccttttt cccatcagca tccctgccta ccctcattgg tgacgagtgt    14820
ggctgaagag tcaagcagcg ccgcatcact ccgtgtgtcc cctttgctgc gatccagccg    14880
tgtctcactg cccagccccg ggcccatatc cttcagattg aagctatagg aagggaaggc    14940
ttgtgggtgg ccaggccccg gcagtccact ctggggaggg ggcaggaagt agccaaggat    15000
```

-continued

```
ctacctgttc atgagcggta ggccgcagga gctgcctttg ccgacgctgt ggttgagatt    15060
ggcagaggat accaagccag ggctacagta gataatccgt aacatggtcc atgtctgtgc    15120
cacctagggg gagggaccaa ccactcaggg gtctccatct cctgagcaga gtcatatacc    15180
aacccatggc ctgatctact accacccagg aaactggccc ctggaaagag cagtgtccac    15240
tctacagtag cacatctgtg aggtgtctgg tgctaagatt agcaatggaa cagatatggg    15300
gaagagagag agcagaaggc agctccaaca ccaagaacga ggtagaagag cgggctgtag    15360
gcacgggact ccttggcctc caccctgagt ttgggctagt ctggttccca tgatctttac    15420
actgtcaaat actgtgacag aggctgccac tgtgactgag ctcagggggg ttgtgggcat    15480
gatgccccaa ctacagcagc agtctcggac cctgggtctc cagcttcaca tacctgattg    15540
cggccaagct cccgagccac ttttgcattg tgatcacaga gctcggctag tggccggcca    15600
gccagaacat aacgttcagc tgtatccacg aaccagctca tgctgccacc gctagactcc    15660
gtctcaaaga cgctcagtgc actggaagcg aggccagaaa aaggttctgc agggtccaac    15720
ttgcgcttga agaagatggg gtggcgccgg tcaccagcat agggtttacg tccagattca    15780
gcagccacca ggctttcctt aacagcaaag gccaggtccc caaagaggcc atagcagaga    15840
ccctcagggt tggcacgctc aacaggctga ctggcatccc gaaacaggtg ctggcataac    15900
gtgctgtcct tggagccgga gagcaggaaa gagggtcat gcggatgacg ccaggcaatg    15960
cctgttgtga catcacgatg ctcttcaaac atagcagctg gcacgaaggg gcggcgtaca    16020
tcccatacat agatgttgtg gtccaccatc atggaacacg tggccaggtg gtggcggcat    16080
tcaggccgcc acttgactcg ggccactgaa gcgattgtct gcacacagtg tatctctttg    16140
gcacgatgtg tggtcatgtc ccagaccttt accatcttgt cacgtccacc cgtggccagc    16200
cagcccctgc ggagaatgtc ccactcaagc tgtcagtgac ctctcccatg ggaaaggaga    16260
ccctgccaca cccaaaggca tcgtttagcc tccagcctta aggcccatct tctccccaca    16320
ccacacctgt cctctgggtg ccaatcacag cagaagacag gcccattgtg ggctgtgaac    16380
atcctctcac agcggtcggg tcggcggatg tcccagagct gtacgttgcc attctcaaag    16440
gtggaagcaa aggtaaagta gtcacggata ctgaactgca catcccgcac gctctcagac    16500
tggcctgtgg gcacacagtg gtacagacat aagtgagggg ctggccccca gggcgtgggg    16560
gagcccttgg agtggctcca accatgttat tcaccagcct atagcccagc ccagaaacac    16620
aggactggag aaacaccacc aaaatctgcc taggccagag tatgccaggt agtttcagtg    16680
cagactccca gcctcagttc cctagattct gcacaggcaa agctgcagac ctgcctcaga    16740
aggctatgtg tgagcactgg aggcacagga gctcaccctc gttggctgtc tatatgtccc    16800
aggccaaggc ttgtggaaga cccaacgaat ggaagaggag gctcctcgtg ctctgctcaa    16860
tgccctgcca gctgcctagt tagcctcgaa ggaccgaaga gctcagagac catacccacc    16920
ttaaaagatc gccaaacaag gagcctgcgg gtacagtgtc cagtgctttt ccctgccaca    16980
gacagctcaa ggtctgttgt aacccccaaa ttctccaggc cccaaggctc tgcctgcgca    17040
tcatttggtc tcattaaaga tctgagagag gggaatgagg gctgaatgca gacagcttgg    17100
cctgccatga aagggcgct gtgtactccc cacctcactc tgagtcccgg tctgagtcct    17160
gaagacacaa ggctccgcca ctcactacgg tgtgtctgaa ggctccgcct tcccattag    17220 ccacacccac cacccagtct caatttccac tggtctgacc tcctgcctcg cccccccccc    17280
caccccaaca gcagtgttgg gcttatcctt ctcaggggc caaccgttcc catttccacc    17340
```

```
actctttctg ggctgttccg cctctgaggg tccatctgag ggcctctgat ggacacacat   17400
ttcagcctgc ctgtcaggtc taacacctac agagatccag atgtacccc aacttcctct    17460
gtgggcctca ccagagaagg tgctgacaga gtccttcctt cggaggtcaa agcacttcat   17520
gaagccatcc tgagagccac tgagcagcac atgggcctcg gtgggatgga aacagacttt   17580
gttcactgtg cgcttgtgtt ctgtgaacag ctgatcctgc ttgttgcggg atggccgacc   17640
taggttccat gtaaccacca caccattggt ggctgctgtg ccagcagat tctcatccat    17700
ctggtgccag accacatcag cacagctcag gttgagcgag gcttcctac ccacacgtaa    17760
attcagcttc tctacgaact gctcctcctc aatggcataa atcttgaaga tgcttcggcc   17820
tgccacgaca acctgggcag cgtcgcggca cacgctgatg gcattagctg cgcgtccag    17880
atggcagtgc atggttcggc ccgtcagagc actgccgctc agggctgtgc taactcggga   17940
catcttttcc atgtctgcac aggtatcaga ggcaggagga ggtcagtgaa gtgtgctgac   18000
ctggtcagcc atggtgtcct aacaattcag gttcagtctc ctctcgaacc ttcggcctga   18060
gatggtccat cagccagtcg ttatcttagg aaggttcaca ttcattggag ttctccagaa   18120
ggctccagag ctaacctgag gttcgtcagc accatatctg acgtctcccg attctatgtg   18180
gttaattctc catcagtgag atcctggggg cggggagtgg ctcctgactt cacagcccca   18240
tgcctccgag gattgcgggg cttccaagag gaaaaacaac cgagtggaaa gggcagagaa   18300
gctagatggg tatggactga gttcatacac cttggaatgc agaagagagg ctacagcaat   18360
aagtgcaggt gtctaattgc accgtgcagc ggcaactgag ggaccagaac caggtgctag   18420
aaaagcctct gccccgtcgc acgccagtca tttaccgaaa gcacagagtg gtcttcagct   18480
acagtaccgg aagagactca cctactgccc gcccattacc ggaagtagtc ctttcttatt   18540
ctcacttcgc cggaagtgag tgacaactcg tctttcacac cataagagtt ccgtgtctgc   18600
gaacagcgct tctgcagagc aaacggacca gaattgggct ccctggtttt aacttggtta   18660
tatatgtccg ctattgatcg tttggttagg gtttctgttt tgttttgttt tgttttgttt   18720
tgttttatgg ttctggaaat cgagcccgag agacaagttc tctaccaact aggctatgtt   18780
tattttaatc tcaatatctt aataccagta cttaaacctt tcctccggtc ttggagaagt   18840
aatttcttt tctttttttt ctttctttct ttttcttttct tttttctttt tctttttttt   18900
ttctttttg gttttttgtt tttgtttgt ttgttttgt tgttttgttt tgtttttgt       18960
ttttcgagac agggtttctt tgtacatccc tggctgtact ggaattcact ctgtagacca   19020
ggctggcctc gaactcagaa atccgtactg ggattaaagg cgtgcaccac cactgcccgg   19080
cgaggagaaa ttttctaagg agaccttgag ttccaccact ctgccacagt gccacttccc   19140
ctacggaagc actagcagcc tggtgccttt tctactctag gtcattattt cactgtgtat   19200
aggtctcaga gacctgaccc tgacctttct ggctcatctg cagctctacc tttcttggct   19260
cctcctttct cagcttgttt ctatcccagc ttccttccct ctgagtattt tccttcttct   19320
ttcacagttc atcagctgtg ttataaaacc atggcttcta cctatggctt ctaccccctgc  19380
agaaggtgtc tcctttacac ataggtaggc acttagctca aatgcctacc atcttaggcc   19440
atccttgcca ccccagtcta atgtctcctt tgtctactgt ggtttgtatg attacacctg   19500
ttttggtact ttcagagcct gacaaccagt catcagtggc ttagtagatt tagtctccat   19560
tgtaagaaat cagtgttggc tgaggagcct caagaccaag ttctcagcat aaagaaagat   19620
tgtttgcccc aaagggacaa aggctaggca atagggacag acagcagata gagggtcagg   19680
gaggagaggg agtagggata tttgaccaga ggggataaag aactgcctct ggatagaaag   19740
```

```
gagacagaca tggcctatag acaaatgaca ctttatgact ttataagtgt aagagggaga   19800
aacaccatgt tagaatgagg tatttaattt tgattagaca ggttaattaa gtgaacccat   19860
gggggctttt gattgctgga cctcaatact ttgatagctg ggccttcatc gccagcctca   19920
ggagtagaag tggccaaata agggaacata ccatggtggc tagctctagg aatataatct   19980
aaggttttta gcaagacaga aggcattgca gagaaggaca aagctggcta gcagtcctcc   20040
cttcagcact tgccctttct cttgaggtgg acacaatagt cttgatcttc tagcagtctg   20100
tgattattta tttatttaat cttatttga gtgtgtgcac atgtaaatgc aaaaatgtgc   20160
ctgtgtgagt ttttatttgt accaatgtgt gttcaggttc cctaggcggc cagagaacat   20220
catatcccta aagctagagt tactgggcag cttaaaggca tctgacgtga gtgctgggaa   20280
actgacccca ggtcttctgt aggaacagta gattctttgc actaccgagc catctatcca   20340
gcatcactgg attattttag aacatcacaa tccctcactt agtgacccg tgcagaagat    20400 aaggctcatt tctgctcttg gatagcaaga tcctagatcc ttgttttctt tttctttttt   20460
ttttcttttt tcttttttt tcttttttct ttttcttttt cttttctttt tttttctga     20520 gacagggttt ctctgtgtag ttctggctgt cctggaactc actctgtaga ccaggatgac   20580
cttgaactca gaaatccgcc tgcctctgtc tcccaagtgc tgggattaaa ggtgtgcgcc   20640
accaccgccc ctagatcctt tggaagacct acattttgac atcaaacaca ttgttccctt   20700
ttgtgcattc aggacattag agaacttatg ttcgtcagtt gctaaggttc cagtccagcc   20760
ctgagcctcc aacctctcct gtttatggag tacctctaat gatttaggag gcaggaagac   20820
ccagagacct gggccatcca gggcagagtt atcccttcca acttggtcag gtgaccaaaa   20880
aataataacc cacttgtgtt tttacaactt ttttaatata tattttttata aacaggtcac   20940 gtgataaaat agcacaagaa acacttacca aatataaggt tatatcttcc gcatatacag   21000
gagaatgagg tcgttatgta caataagaaa atgattttag gggttggttg gttttgtttg   21060
tgttcctctc tcccttaaa ttttcctcct acagtcattg gaaatatcac agcttcagtt    21120
gcattaatac tttgggcaaa tggacagctt ccccctccct gttggggac tgtgggaaga    21180 ggggctgaca aatctggctc ctgaccactt cagcctgggg cctccctggc caacactgca   21240
ggggcaggga actctttggg ctgttgaatc tttacttttc gtcaacagca tctctctctc   21300
tcctctctct ctctctctct ctctctctct ctctctctct ctctctctcc ctctggctct   21360
ctgggaatta gtttactctc ttccaaccag atagggtgt cccaagatta gttgtgggtg    21420
ctgtgtctcc tggggttcaa ggttgggagg gaaggttccc agtcccttcc tcggtattgt   21480
cacctatatg ccaggatccc ctaggacttc caaatttctt gagacctgac agaacatggt   21540
cacaaaccct ttgggcaggc aaaggttttg gaagctggga gaactaaagg aggactggga   21600
aggagccctc cttccctggg gtgtgaaggg ggtgctggcc actgggagat cagaatcgct   21660
ggtcagtact gaccctgact catggccagg ccctctgcag attccacctg aggagaccta   21720
tccagggaga agcacagtgc tgagaggcct gagctcagct ggggtagggg ctcaaatggg   21780
tgggctgatc ccaaggcctg atagccctgt gggtggctcc agattggggt ctgccaggtg   21840
cctattccac ccttgcactt aggtggatgg gcaccggtta ggctaatgtt gattgttcca   21900
aggtctgcgt cctcctaaag ctgtcccaac ctggccaggg cccaaggatc tgtaggccag   21960
ggggaaagaa ggagatacgg gggtaggggc gcaggataca gaggacaaga actgacctat   22020
atggcaacaa ggaagaaggg aagccactag gtcaggtggg catggggagt tgggctcctc   22080
```

-continued

```
aggggggccat ggctttggca gtggcctgtg gcgcctcata cccttttggag ggctccaggc   22140
gcggtgcagt ggaagatgtg ggaggccctt gggggctctt ccaggcccct aagtcctggg   22200
ggaccaatcc ctccatcccc ttgggccctg cccgggatgg ggggacagcg agggggaggca   22260
gagagcagaa tgaagtgggg aagccagtga gggcatatgc actcaaagca tccccaaaag   22320
gacctagacc cccagaaggc gggcgagtga tggcggcggc tgtggcatgg tggagggcgg   22380
gcgtgcagtg cgggcacgag gggcatgcac aaagtccccg agtgtgcgtg cgtgcgtggg   22440
gctggcccct ctgcctcttg ccccagacag ggaaggagca gttgagcaga ggagcaaggg   22500
aggcacgggg cgggatttcc ctcagcttgc cccgcctcca gcgcagggcg agaagagat   22560
gctccggcag ggatggaaga agggctactg cccagggcgt ggccggttcc cgcggccggg   22620
tcgggaagcc tgcgctattc aatgacgagg cagcgcggca ggtgctgcga gaagtacttg   22680
aagagctcgg gtgtggctcc agggcagttg gtcagctcca gctcctccag ctcttgcagt   22740
tgcacgaggc cagatagccc ggtggtagtt aggagcgggc agcctgcaag catgaggcac   22800
ggggacagcc gctcagcagt tcagttccgc ctggcgggag gactggactg ggctgggcag   22860
gtgggaaagg ctgaagagga caatgacctg ctaggggtgg attctactgg gcttgctgaa   22920
tgaggcggga cctgtaccgg gcgtggaggg gtgggaatct gacaggatgg gcgggacctc   22980
caccagggaa ggatgtgttc agacttggcc tgatgcaggg tagatctgag cagggcgtca   23040
ccaacagggc ttggattcac cctctaaccc gctacctggg atgcgatttg ccaaaacctg   23100
aaatgaatct atctgcacaa aggacctgat gggggtgggg gtcagagtga gtgggcatcg   23160
ttgcccatga ggcatgcggg ggtgggggggt gtctcacctg ctagagacaa gagtcgcaaa   23220
tttctcatgg ctaagaggtg cttcaacccg aagtcctgca cctgggcggg agtgagagga   23280
ggtcgtgtta acttatttcc acttgcttgg gacctggagc cactagaggg gcaggaggta   23340
ggggttcaaa atggagattt ctcagtccca cccccacccc ccgtagactg gaagcaccaa   23400
gagggccttg gggaatctgg aacccaatga ttctgcttag tttggctgct ggttctagag   23460
gactctgaat gaggcggggt gaagttcaag gataatctgt actggtcctc caccctgtcc   23520
tgtcccgcca ccaaccacgc tctaatttcc agatccctgg gggcatggag gtacctggca   23580
gcaccatcgc aggtagaggc tgcggagaga cgacatggtg gacaaatagc tgagaccagt   23640
gtccgtgatg cgtacacacc tgtggttgca ccagaagggg gactgcccac ctttaaatca   23700
ctttacccca tccccaccta ggtccttccc ccttttcag aggtgtccct agagcaagtc   23760
tctgcccac acaccaatgc cctattcttc ccctggtccc accccgtggc ctcccctttt   23820
ggaatatggc ttttcctcca gttttgggca ctctattcta tgtggttttc cccatccccg   23880
aagcctgtga accgggcacc acccactcta ggcttccagt tcctggagat cccaccagta   23940
cccgcctgga gtgtagggat gtgtgcacct gtccagcacg agctcctcca gtcggtgcaa   24000
gtcgcaggcc acatactcca gtgccatatc ggtgatccga gggcaccagg aaaggtcaag   24060
gctgcgcaat ttgcgcaggt tctcagctac aagctccact ccatcatcag tgaccttaga   24120
gcagcctgag aggctgagtg aggtgaggtt ggcagactg tgcaccacat tgaccacccc   24180
atggttggtt atctcccagc aggaaagcag gcgcagcgtg tgggtgctgt ggccctggcg   24240
tgctgtgaag taggccaggg ccgtgtcagt cacgtgatag gcctgaaggc ttagctctgc   24300
caggttgggt agaagttgtg agatggcagc gattgcatca tctgccacat tgatgcagtc   24360
actgacgctc aggaggtgaa tacgggcact gaggctggac cacaggccag cctcggtgaa   24420
atcgttgcag cctgacagct ccagacgcac cactccctgc atctgctcca gcatcaccta   24480
```

```
caggcaggta caaatcagac taagtcagct ccctggctca cgcctgcccg aagaagtttc    24540
tgggattctg gaagcggtgg tctctcaggc gtgggcttgt gcaagcatgc atcaggctga    24600
actccaagga atgcacttaa actgcttgtt atactttccc aatattccaa gggggggaggc   24660 agggcacagg ggacacaagc cagggtgtgg ccagtgcagg tgtttagaac agatgatttg    24720
aatattaaaa ttacaatcca ggtccagggg tgtggggagg cagggcaggg tgcttctagg    24780
agactcttag ctacccctcc acacaccagc ccagcagccc attcaccaag gcagcttcac    24840
aagcaagcag acacccacat gtaattgact actctcttgc accaaccttg acatcttaat    24900
cactttttaa caagcccaca ttttcacttt gcattaggcc ccgaaatacc atccttgctg    24960 cttttatcc tgtatacacc tgagtatctt ccaggcccct caacctccca tgtccataag     25020
gttgcttctg catgttcccc accccctcc ccagacccag acccatctgg tcatagccaa     25080
ttttgggaca cacctctaga ccagcgtcag tgatggtgga gcgcttgaga ctcatggcct    25140
tgactccctt cttagagaga gaatagttgt cgatgaactc gcagatgtct aagtcggaga    25200
caccaactag gcagaagccc tcaaaacctc tagcagcaaa gccctgcagg ttcacaaact    25260
ccttctcgcc tccaggcagc acgttgtaca gctccttggc atgcagcaca ggcgtgaggc    25320
ccgcccagaa cttgggctgg tagagcacac gccgccaagc cttgcacacc tgagctagta    25380
tgcacttctc acatgctgag aaataccaga aaagcccatt aaggatcttc tcgtctgtgg    25440
ccagtggtgg ccgctccact gggggtccag acactggacc cgaggctggt ccactggctg    25500
gggggcatgg ccccccggcc agagcaaccc gggatagtgg tgtagccagg cttggaggtg    25560
ggagggtcgg tgggggtggt ggctggcaag gacggttctt ggcagcaggt gtgcccttgg    25620
tgatgctggc tgcacctagg ccgttgggct ggccaggcag cttcaccaga ccgtttcgag    25680
gcaagcatgg aggcttgggg tcaccatcga taccggggct cgacattttt cttgcacgct    25740
ctgtggatga gacaggagga acaaataagt gtgccaggct ctggaggaac tggagagcta    25800 acctttctc atcctcgagg ctcctcaccc aaagcatttc caggaccact aacagaaca     25860 gatcctagta tgcgcctttc tctgtctgca caagaggcaa gctggccaca ttcacagcta    25920
gctcaagtgt ccacatcctc tctctgtcct attcactggc tcagcctgcc ttgctcaaag    25980
gtgctttctg atgctctgat tcccatcgag gcttggggag atggaatcct ttttttttt     26040 tttttttttt cgttttcaa gaagacaggg tttctctgtg tagccctggt tgtcctgtag     26100
accaggctgg ccttgaactc agaaatctgt ctgcctctgc ttcccgagtg ctgggattaa    26160
aggcatgcgc caccatgccc ggtggtagat ggaatcctta actgttcctt tcacctccaa    26220
tcctctgatg ccccttcctg gagtttatct tgaggactag gatcggagaa cccagagaag    26280
aaaggtgctt gaatagccct gagtcacaga ccagctctcc aaaatctgtg cacctagtca    26340
gtggtggcac atgccagtgc ttgggaggca gaggcaggca gatctctgag ttcaagagca    26400
gccttgtaca gagagagttc caggacagcc aggactacac agaggagccc aatctcaaaa    26460
gagaaaaaaa atctgtatcc ctataaaagg ctctgaggct cagtcgcatc ccctgtatag    26520
ctgactgtgc taccagcaca gtgatacttg gacacatgct ttttcatatt taaaaattt    26580 aaaattttct gtgtacgggt gttctcttgc atgtgtacca catacatatc tgtgaattc     26640 agaagaggac atagatctcc tggagctgga gttacaggcc tctaggtcct ctgtaaaagc    26700
agcaggcacc caagcactga ggcacttctc cagcctgctg gacacatgct ctaatccccc    26760
acccgagtca acgcaaacag tgctgtgctg tctctgtaca accaaggaag tagaggccaa    26820
```

```
gaccaagaga actatctgac taagctcatg gccgatagtt aagtggtaga gctaaaattc    26880
ggatcagaac tggaggagga aggtcatatg gaaggccagc atgaccaaca tgtctgaatc    26940
actccctccc tgttcccctc agactcccag gcctgtgact gggttgcaga ggacactgtg    27000
agtggacagc acggagggaa agagcagtga gactctcata atgccatgat ctctgtctgc    27060
tctgcattcc agacatcaca cccaccacca cccagcatcc agaaggatgt gattttccca    27120
tggatttcac ctgcagatga aatgctcaat gcaacactta aaacattcaa aggcaatact    27180
ctggactcca gatggcccct tctataaatg agtgctcttg gctagcctct ggtgagtcca    27240
tttcctcaac atgaaatctg ggaggtgaca ccacaaactc cttcctgtgg gagggatttg    27300
cagtctatgg tagtgtaaat cctgagtccc agagctgacc caagggcaag gcagggtttc    27360
cctttctgtg tgtataggtg atcccaggat gagcaggatg cacacatgaa ttgtcagttt    27420
ttgccctaca atctccaggg agtcaacaaa agcctctacc aaaccttcag tcataccttc    27480
atacctggct ttggtggctc ataaccttgc cagggagcct ggagcaatac caagggctac    27540
atgaagaagc ttcccaagtg gtgggcactg aagtacacag accctcagca gagaaagact    27600
catgttaccc tttaggttga ccccctttc tggagctaca gggccaagga aattggctac     27660
tctttcttat actctggctt gacacaagag aagtagacaa gaactacctt ctgcctttat    27720
tttgcaattc tgtctctatg gttccctata ttgcacatgc aatctgtgct agtttcccac    27780
ctctgggaag ggaaagtccc gggttaagct ctccccagaa catggtcctc atgatgaacc    27840
tagttctgtg tctaaggatg gccattggca gtccaccta aggccctcag tactgtctcc     27900
tgattactcc ctttctcaat atgactctta agacctgggg agtaggccag ctattcccta    27960
aaggtttcag accttggctg ctctttgtgc tcaagaacag gcaatagtag ctacaaaaaa    28020
aaaaaaaaaa aaaaaaaaa aaaaaaaaa agccagtata gcaagtagca atgctaacac      28080
ttgccaaatg cacactggtt caatcacata agaacccgag gctctgaaga gttatagttt    28140
gcatgctacg gtaagggaag tctaaagtgt ggttacccca attccctgga gcaatatagg    28200
gaagctggcc tgttgcggga cagcagcatc catgatggga aaggatgaga ttcttcctta    28260
tgtgctccaa ttcttatcca gtaccaccg cattcctggg aactgtgctg agggtggaga     28320
gacagcccca gcctgagtac cagccatata ctaagtcttg gtctacctct agactgccca    28380
tggaacctca gccactaggc gcagaatcag cgctctcgga accccgcaag cagcaccacg    28440
gacagctccc gcgctcaatg tggtcagccg ggctttctgc accagagaca gtggagcgga    28500
ggaggaatga tcggtggctc cggcaaaccc agctccacag gaagaggcag agggagaagc    28560
cgcccgcttg gctaggatct ggaggaggct gcggaggcgg tgccagggga gaaataatcc    28620
aagagctgtg ccgatttagg ctgaaaatgc tcccagccgc gggtgtgcac gtggagcgcc    28680
tgagttgctg ggggttgggg gggagatgca cgtggatgcc ccgggcatct gcagggctcc    28740
tttctgcccc tctctgcagc tctggagatt cacgtttcca gaagcacacg atcgacccc     28800 ttcccacctt ccagacttgg gtcacatagg tgaatccagg ccagattcag tgtctaattc    28860
ccccatccag gccctgtcc ttggtggaag cctcatctcc acaaagtcaa cctcgctttg     28920
tgattagaga ggttctcact tattctttct ctttgacatt aaccaagcct gagaacccca    28980
caggcgtcca aaaatggaaa cagttacacc tgaactcaag ggctgaggct ttcagagaaa    29040
gctaagcaca cactggaaga ctggaacttt cttgccaggt gagcaagagg ttattgaggg    29100
gttctaagca aggatcactc cacctggccc tgccatctca ccagatgatg acataaggtc    29160
tgctcccagg tatcgttcta tagcccaggc tggccttgta tttacagcca tcctacctct    29220
```

-continued

```
ctgggattac aaatatgtac tgccatgcct agctagagct ccttaatgat gctgcaactc    29280
ctgcttccta ggagggggt gggggatgg atcagtggcc aagtgaccca ggttgtctct      29340
cccttcacgg acaagcacct caggagctaa tactgaggag aggccttctg gaatgatgtc    29400
cgaactggca cagcactcag ccccaggccc agtatgtcct gtgcttggtt tggagtagaa    29460
ttctgggtca tctctagact gcaggggagc ttgagatggg actccctagg tccatcctgg    29520
gctaggaagg gacagtgaca acttcctcag ctgctgtgtc ttcatcagcc cgtctcatca    29580
aggtgctctc cgggagcact gactgtagtc tttgccctct ctagaggact cattgtggac    29640
ataaggaaca tggagggtac aatgggtctc ctgggaaagt tccagtactt ggtgatttcc    29700
agattggcat tccacagagt ctgatgctga accacgagga cttgcctctt ttgtatatcc    29760
agtcatcaaa agagtctcct ggcctcatct ccatccattc ctccttccct agccagaccc    29820
ctgctcttca ttctcccacc cccctcacc tggacaagtg gcggtgccct gcttgtctca     29880
taggctttct cagtgccgag cttgctgcct gcctccatag ataggatccc ctagtactct    29940
gaaaaagcac ctccaggtgt cacctggaga tgtcatcact gtttctaccc gtggcctggt    30000
aactccttga agacaaatag caccatgagt gtgtggcttc tgggtactgc tgaaggaatg    30060
gacaagaaat ggtcacctga accattcagg ttcaggggtg cagctgcccg aggctgagag    30120
ccttggctgg ttggcgggc aggagaagca caagaattta actccgggta tgcttgtggt     30180
cagcatttgt tcaaagaaa tagattggtg ccagcaccta gctccccaga cccgctgatc     30240
ttgaggtgca ggtactcagg gagaggagat cttttggcta agtccctctt ctggggtttc    30300
atggctaagg aatctgactg gctgacccc aaaatctgac ctgatcctag gaaaaagaga     30360
caggagtcac caaggagatg ccttcctcca acatccctgc ctcatgactt cctagagcac    30420
caccgttcaa aacaagcctc agaaagggat ggatctttct gatgctgcag agaactgcca   30480
cttgtcccaa gaccccaaag cactcagact aggaacacat ctgttgtacc ttgtgtcttt    30540
ttcttctgcc tcactgggtc ctgtgttttc ctatgatttg actagtggcc tctgcacaca    30600
gctatcttcc agcggggtca ctgctgttac cctgaaatct taaagaccgc caactacaca   30660
ctcaccaatg tctcacccgt catctctctc agtctaggga ctctttccct gagtctgtgc    30720
acaggtcagt atgaaggcca ccttggaggc tggcttctgg cctgcatagc acctgccctg    30780
atcagctcct caggtttgaa aaggacaacc aaaacaccca tctccagttc agtctgtagt    30840
ggcagccccg tggcctgggg tgacgaccag ggtatctgag attgggggca cagagcaggc    30900
aacatgttct gtgacagtgc tgtgactcag gcacattcac atccctgcca cttttgcacgt   30960
gtcaaccaca gcacttttct tccaccccct gctggagctg cctctggggt gtgtgtgtgc    31020
cagggacttg gggataggga gaccttggc ccaggaggta aacagaccca ggttgaacct     31080
aggtcaatgc tccagaagat caaactaatg ctctgtgacc aaactaaggg caaatagtca    31140
cgacaggctt catcttatca cgcccccct cccgctgttc tgtagaatat gagaccttca     31200
aaacccaagg ctcctttaga cacctgccaa gtgaggccca cctgcactct ctgcagccag    31260
tttggccatc tgaccactaa tggggacagt tcagggctgc tcactgacct cctgaccttg    31320
ctttgctgcc ttccccccc ccccccagtg ccagtcccgg aaggttcatc agtgactctc     31380
agaggtgaag gcttatggtc aggaaggttg agtgatgccc accagaagcc ccttctagtg    31440
cctctgaaat agagagccca atctctcagg gctacctaga tgcacttgtt ttaacttcat    31500
cagtgcgaga cggaccctgt tcaggtgtat ttgggagaac aggtgagtgc atacgtgtcc    31560
```

```
tggacttaca gtatgggtga ctggggaggc aaatagtgag ggtggcagga aatgaggctg     31620
ctgaatcttg ggctatctca acatcaccca cgttttcaac cttgactttc cctctcttct     31680
cccaatggct cccagcccgg ccctcaggcc acgtctaggc aggaaatcga ggctccacca     31740
tgcctctgac ctgatctagg cagcccctaa tcatccaggc tcctgtccca acaccggccc     31800 ccccccccg ccctcccccc ctgctgcgat gaggctgctg tccagcactt catcaaagtg     31860
ttgggctgga acagagggtc ccgtgtcccg aaggggcagc agggaggcct gagaagaccc     31920
tggtcagtgg gccctgggac aagatggcag tggaagtcgg gcctccagga gggagcaggt     31980
gaagtggcat ctgccatctg ctcctgggag gtcagctgct ggctcgggct gggaggggct     32040
agcaggaggg ctgctaggcc agatccaggc ctcaacagtg cagccttctc tcctgggatg     32100
acgggtgggg aggatccccc actgactaac atcctagaag acatggaag ccctgctcag      32160 caatctcagg atgcccattc cccattttga agccttccaa tcttggccaa ggcccatttt     32220 cttttttctag aaccaaagac atgccagccc actccctggt atagagctgt gggcggcagc     32280
tctataccag ctcatgtcca gaaggcgtcc aggacccta ggccacatat ccacatggct       32340
cctccctttt aattgtatca acacctgtca cgtcctccag tccgccggag gctcataggg     32400
ctggagtggg gagagcccag agccaagcca gaaggagtgg gggctgacgg cctgcagttc     32460
cgcgtcctcg cagccaccgt gcttcctctc agcaattccg tggtacggag atacagcctg     32520
accgcgctgc cggtagcgag cggggcgcaa tcaggccggc cactagggtt aggggctgcg     32580
gaaccgctgc tcagcggcc gaaggtgag gtggggaagg ggctgcgatt acgtaagccc        32640
tgctcaggcg gcggcggccg cggcgcagtc ccaagtcccc accccgcccc ctcctcattg     32700
tagccttcgc ggaggcagtg gctcgacctg gaccctcccc tccccgcagc ctggccgcgc     32760
gcgcacacac accttacctc ggccagggct tctggctcat gccacgctgt ccgccgggcg     32820
acctcgcgtc atgggagct cagcaccga gccgctagc gcggaggcgg ccagggtgct         32880
ggactggcta gcagggcccg actgcgcccc gcgcccggcg ccccgcgcca gggccctctc     32940
cgcagagttc cgagcggagc tccccggtgg gagaggatct gccgccctga gcctcccacc     33000
ggggaggctg aggctgtgcc cagataaata aggccgcttt gcagggaacc cggcgggcgc     33060
ctcctccctc cccttcccct cctccctgcg ctcctcctcc gcgctcctcc ccgcgctcct     33120
ccgcggccgc cgccggcgcc gcgcgtgccc cccgcccggc cctaagagcc gcgccctcgc     33180
gcgctcccgg cgtccggacc aatccgggtt ctagagccag gctgaggtgt cgagaatccc     33240
caaccccgcc ccgctcctct ccgcgcgctc ccggtgcggt accgacgggc acgcgccagg     33300
cggcagcacc cgctcagcgg ccggtgttcg cacaataaca aacccgtag gccgcgcggc       33360 cgaagagcag cttcgagtgt cccatctgca caaagtggtg gcgacccaga atcttgccag     33420
ctgaggagaa ttgcggtcct tggcgcgagc ggttggcagt ggggttccgg atcctgcgca     33480
gatgcaactg gccctatgtg cccttgcttg gattgccacc tgtgagggcg aggaaagaga     33540
agccgagtgg agacatcgac atcgtcgcac ctccacacac acacacacac accctcctta     33600
tggcccctag gattcatatc ccttccgatc ctgttgcgag tcaggcagaa gaatccctgt      33660
tctgggtgac atagtcacac acttgcaagc aagtgactaa agcaagcgtc aatgaaaaca     33720
caagacagtg gagtgatagt ggggaggggt tacttctgac aatgtcacaa atgatctgag     33780
acgccctctc tgtccccata gcacttggta ggaatggttc gagaatcgac ctgccttatg     33840
gagttccaca ggttcgctct gagatgaagt agaggtcagg tggtggcagc ctgtatggac     33900
cagggagggt ggtttgtgta aaaggaccca ttaagggctg ctggagagcc agacctctca     33960
```

```
gcaggctaaa gggaccccaa tctgggtctc tcttgagacc agaaacagca gatgttggga    34020
cagcagagta gcgtcttgga agagaaggag cttcagggtg gaatgtcctc agatgagacc    34080
aactgctgtg gagatgggag gtctgtctcc tgggaatgat gtgaggccta ggggcaataa    34140
gaaagggaag taagctgtat cctagctggt gtgtgtgtgt gtgtgtgtgt gtgtgtgtgt    34200
gtgtgtgtgt gtgtgtgtgt ggtgtatgat catatatgtg aagggcgaat tcgtttaaac    34260
ctgcaggact agtnnccctt agtgnagggg ttaattnntg nagcctgggc gtataccta     34319

<210> SEQ ID NO 48
<211> LENGTH: 21
<212> TYPE: DNA
<213> ORGANISM: Artificial Sequence
<220> FEATURE:
<223> OTHER INFORMATION: human and rat origin

<400> SEQUENCE: 48
cacccaccag ccgcactggt c                                              21

<210> SEQ ID NO 49
<211> LENGTH: 19
<212> TYPE: DNA
<213> ORGANISM: Artificial Sequence
<220> FEATURE:
<223> OTHER INFORMATION: human and rat origin

<400> SEQUENCE: 49
gagcagctag ggttcaatg                                                 19

<210> SEQ ID NO 50
<211> LENGTH: 32
<212> TYPE: DNA
<213> ORGANISM: Artificial Sequence
<220> FEATURE:
<223> OTHER INFORMATION: mouse origin

<400> SEQUENCE: 50
ggttaattaa ccaccctcca tccccagctt tc                                  32

<210> SEQ ID NO 51
<211> LENGTH: 37
<212> TYPE: DNA
<213> ORGANISM: Artificial Sequence
<220> FEATURE:
<223> OTHER INFORMATION: mouse origin

<400> SEQUENCE: 51
agctttggcc ggcctggtcc ttggacctag gtccttc                             37

<210> SEQ ID NO 52
<211> LENGTH: 32
<212> TYPE: DNA
<213> ORGANISM: Artificial Sequence
<220> FEATURE:
<223> OTHER INFORMATION: mouse origin

<400> SEQUENCE: 52
aaggcgcgcc cctggaagtc cacagtttct tc                                  32

<210> SEQ ID NO 53
<211> LENGTH: 35
<212> TYPE: DNA
<213> ORGANISM: Artificial Sequence
<220> FEATURE:
```

```
<223> OTHER INFORMATION: mouse origin

<400> SEQUENCE: 53
agctttgcga tcgctcagtc caagttcagc aatcg                          35

<210> SEQ ID NO 54
<211> LENGTH: 38
<212> TYPE: DNA
<213> ORGANISM: Artificial Sequence
<220> FEATURE:
<223> OTHER INFORMATION: mouse origin

<400> SEQUENCE: 54
atagtttagc ggccgcccgg taggaaggcg gaattgag                       38

<210> SEQ ID NO 55
<211> LENGTH: 35
<212> TYPE: DNA
<213> ORGANISM: Artificial Sequence
<220> FEATURE:
<223> OTHER INFORMATION: mouse origin

<400> SEQUENCE: 55
atagtttagc ggccgccagt tcccttagct ctgag                          35

<210> SEQ ID NO 56
<211> LENGTH: 20
<212> TYPE: DNA
<213> ORGANISM: Artificial Sequence
<220> FEATURE:
<223> OTHER INFORMATION: mouse origin

<400> SEQUENCE: 56
tatcacaggt aggtgaccac                                           20

<210> SEQ ID NO 57
<211> LENGTH: 21
<212> TYPE: DNA
<213> ORGANISM: Artificial Sequence
<220> FEATURE:
<223> OTHER INFORMATION: mouse origin

<400> SEQUENCE: 57
acagccctgg gggggcaaca c                                         21

<210> SEQ ID NO 58
<211> LENGTH: 20
<212> TYPE: DNA
<213> ORGANISM: Artificial Sequence
<220> FEATURE:
<223> OTHER INFORMATION: mouse origin

<400> SEQUENCE: 58
gagccattgc taacggacag                                           20

<210> SEQ ID NO 59
<211> LENGTH: 20
<212> TYPE: DNA
<213> ORGANISM: Artificial Sequence
<220> FEATURE:
<223> OTHER INFORMATION: mouse origin

<400> SEQUENCE: 59
cctcatagct ccgaaggatg                                           20
```

```
<210> SEQ ID NO 60
<211> LENGTH: 20
<212> TYPE: DNA
<213> ORGANISM: Artificial Sequence
<220> FEATURE:
<223> OTHER INFORMATION: mouse origin

<400> SEQUENCE: 60
cagacgttcc caggctgtcg                                              20

<210> SEQ ID NO 61
<211> LENGTH: 20
<212> TYPE: DNA
<213> ORGANISM: Artificial Sequence
<220> FEATURE:
<223> OTHER INFORMATION: mouse origin

<400> SEQUENCE: 61
ctacagtaac cgagacctac                                              20

<210> SEQ ID NO 62
<211> LENGTH: 34
<212> TYPE: DNA
<213> ORGANISM: Artificial Sequence
<220> FEATURE:
<223> OTHER INFORMATION: mouse origin

<400> SEQUENCE: 62
agctttgttt aaactcaata cagtgcgggt caac                              34

<210> SEQ ID NO 63
<211> LENGTH: 20
<212> TYPE: DNA
<213> ORGANISM: Artificial Sequence
<220> FEATURE:
<223> OTHER INFORMATION: mouse origin

<400> SEQUENCE: 63
cgacagcctg ggaacgtctg                                              20

<210> SEQ ID NO 64
<211> LENGTH: 22
<212> TYPE: DNA
<213> ORGANISM: Artificial Sequence
<220> FEATURE:
<223> OTHER INFORMATION: mouse origin

<400> SEQUENCE: 64
cctcgaatcg tggatccact ag                                           22

<210> SEQ ID NO 65
<211> LENGTH: 19
<212> TYPE: DNA
<213> ORGANISM: Artificial Sequence
<220> FEATURE:
<223> OTHER INFORMATION: mouse origin

<400> SEQUENCE: 65
tccctgcacg accttggtc                                               19

<210> SEQ ID NO 66
<211> LENGTH: 20
<212> TYPE: DNA
<213> ORGANISM: Artificial Sequence
<220> FEATURE:
<223> OTHER INFORMATION: mouse origin
```

-continued

```
<400> SEQUENCE: 66
gttctaccac ctcatattcg                                               20

<210> SEQ ID NO 67
<211> LENGTH: 20
<212> TYPE: DNA
<213> ORGANISM: Artificial Sequence
<220> FEATURE:
<223> OTHER INFORMATION: mouse origin

<400> SEQUENCE: 67
tttggaaggg aggctgaaag                                               20

<210> SEQ ID NO 68
<211> LENGTH: 20
<212> TYPE: DNA
<213> ORGANISM: Artificial Sequence
<220> FEATURE:
<223> OTHER INFORMATION: mouse origin

<400> SEQUENCE: 68
ggaagaaact gtggacttcc                                               20

<210> SEQ ID NO 69
<211> LENGTH: 20
<212> TYPE: DNA
<213> ORGANISM: Artificial Sequence
<220> FEATURE:
<223> OTHER INFORMATION: mouse origin

<400> SEQUENCE: 69
gtgaacctag ctctgttgtg                                               20

<210> SEQ ID NO 70
<211> LENGTH: 20
<212> TYPE: DNA
<213> ORGANISM: Artificial Sequence
<220> FEATURE:
<223> OTHER INFORMATION: mouse origin

<400> SEQUENCE: 70
accttggtct ctgagactcc                                               20
```

RRP SEQUENCES AND KNOCKOUT MICE AND USES THEREOF

REFERENCE TO RELATED APPLICATIONS

This application is a Continuation In Part of U.S. utility patent application Ser. No. 09/908,419, entitled "Human RRP Sequences and Methods of Use" filed Jul. 18, 2001, which claims priority to U.S. provisional patent applications Nos. 60/219,289, filed Jul. 19, 2000, 60/277,487, filed Mar. 21, 2001, 60/277,471, filed Mar. 21, 2001, and 60/304,863, filed Jul. 12, 2001.

Priority is also claimed to U.S. provisional patent applications Nos. 60/296,076 filed Jun. 5, 2001, 60/305,017 filed Jul. 12, 2001, 60/328,605 filed Oct. 10, 2001, and 60/328,491 filed Oct. 10, 2001. The contents of the prior applications are hereby incorporated in their entirety.

BACKGROUND OF THE INVENTION

Signal transduction pathways are made up of growth factors, their receptors, upstream regulators of the growth factors, and downstream intracellular kinase networks. These pathways regulate many cellular processes, including proliferation, and appear to play a key role in oncogenesis.

The epidermal growth factor receptor (EGFR) and its pathway members are among the most widely explored signaling pathways. Signaling through this pathway elicits diverse biological responses whose manifestations can include mitogenesis or apoptosis, enhanced cell motility, protein secretion, and differentiation or dedifferentiation. Up-regulated EGFR signaling has been implicated in organ morphogenesis, maintenance and repair, and is correlated with invasion and metastasis of many types of tumors. Upregulated EGF and EGFR in various tumor types leads to increased expression of p21/Waf1/Cip1, leading to an arrest in the G1 phase of the cell cycle (Reddy K B et al., (1999) Int. J. Cancer 15:301–306).

Signal transduction pathways, such as the EGFR pathway, are evolutionarily conserved among species as distant as the worm Caenorhabditis elegans, the fruit fly Drosophila melanogaster, and vertebrates (Duffy J B, and Perrimon N, Curr. Opin. Cell Biol. (1996) 8:231–238). In fact, ligands for the Drosophila EGFR (DER), known as Spitz (Rutledge B, et al, Genes Dev. (1992) 6:1503–1517) and Gurken (Neuman-Silberberg F S, and Schupbach T, Cell (1993) 75:165–174), are both similar to TGFα (transforming growth factor alpha), the ligand for the vertebrate EGFR (Massague J, J Biol Chem. (1990) 265:21393–21396). The rhomboid gene, which encodes a transmembrane protein, is another upstream member of this pathway (Bier E., et al., Genes Dev. (1990) 4:190–203). In Drosophila, rhomboid protein is a transmembrane serine protease, cleaves Spitz, and transforms Spitz from a membrane-bound to a secreted form, and thus triggers and upregulates the DER signaling pathway (Wasserman J D et al, Genes Devel (2000) 14:1651–1663; Lee J R, et al., (2001) Cell 107:161–171; Urban S, et al., (2001) Cell 107: 173–182). DNA sequences related to rhomboid have been identified in C. elegans (Wasserman J D, and Freeman M, Trends Cell Biol (1997) 7:431–436), and in mammals (Pascall J C, and Brown K D, FEBS letters (1998) 429:337–340; human: GI#3287191 and GI#7020534, among others; and rat: GI#3297936;), suggesting that rhomboid function may be evolutionarily conserved. Modulation of EGF-receptor related activity by synthetic peptides or humanized monoclonal antibodies inhibit tumor growth (Baselga J, et al., (1998) Cancer Research 58:2825–2831; Park B-W, et al., (2000) Nature Biotechnology 18:194–197).

The p53 gene is mutated in over 50 different types of human cancers, including familial and spontaneous cancers, and is believed to be the most commonly mutated gene in human cancer (Zambetti and Levine, FASEB (1993) 7:855–865; Hollstein, et al., Nucleic Acids Res. (1994) 22:3551–3555). Greater than 90% of mutations in the p53 gene are missense mutations that alter a single amino acid that inactivates p53 function. Aberrant forms of human p53 are associated with poor prognosis, more aggressive tumors, metastasis, and short survival rates (Mitsudomi et al., Clin Cancer Res 2000 Oct; 6(10):4055–63; Koshland, Science (1993) 262:1953).

The human p53 protein normally functions as a central integrator of signals including DNA damage, hypoxia, nucleotide deprivation, and oncogene activation (Prives, Cell (1998) 95:5–8). In response to these signals, p53 protein levels are greatly increased with the result that the accumulated p53 activates cell cycle arrest (through activation of p21/Waf1/Cip1) or apoptosis depending on the nature and strength of these signals. Indeed, multiple lines of experimental evidence have pointed to a key role for p53 as a tumor suppressor (Levine, Cell (1997) 88:323–331). For example, homozygous p53 "knockout" mice are developmentally normal but exhibit nearly 100% incidence of neoplasia in the first year of life (Donehower et al., Nature (1992) 356:215–221).

The biochemical mechanisms and pathways through which p53 functions in normal and cancerous cells are not fully understood, but one clearly important aspect of p53 function is its activity as a gene-specific transcriptional activator. Among the genes with known p53-response elements are several with well-characterized roles in either regulation of the cell cycle or apoptosis, including GADD45, p21/Waf1/Cip1, cyclin G, Bax, IGF-BP3, and MDM2 (Levine, Cell (1997) 88:323–331).

Modulating signal transduction pathway activity involved in tumor growth and development is essential in understanding the development of many cancers, and eventually, for the treatment of cancer. The ability to manipulate the genomes of model organisms such as Drosophila provides a powerful means to analyze signal transduction pathwasy that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551–1557; Gateff E. 1982 Adv. Cancer Res. 37: 33–74; Watson K L., et al., 1994 J Cell Sci. 18: 19–33; Miklos G L, and Rubin G M. 1996 Cell 86:521–529; Wassarman D A, et al., 1995 Curr Opin Gen Dev 5: 44–50; and Booth D R. 1999 Cancer Metastasis Rev. 18: 261–284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry, the gene is identified as a "modifier" involved in the same or overlapping pathway as the genetic entry point. When the genetic entry point is an ortholog of a human gene implicated in a disease pathway, such as p53 or p21, modifier genes can be identified that may be attractive candidate targets for novel therapeutics.

All references cited herein, including sequence information in referenced Genbank identifier numbers and website references, are incorporated herein in their entireties.

SUMMARY OF THE INVENTION

We have discovered genes that modify the p53 or p21 pathway in *Drosophila*, and identified their mammalian orthologs, hereinafter referred to as Rhomboid Related Proteins (RRP), and more specifically, RRP1–RRP8, and mouse RRP1 (mRRP1). The invention provides isolated nucleic acid molecules that comprise nucleic acid sequences encoding RRP protein as well as fragments and derivatives thereof. Vectors and host cells comprising the RRP nucleic acid molecules are also described.

The invention provides methods for utilizing these p53 or p21 modifier genes and polypeptides to identify RRP modulating agents, which are candidate therapeutic agents that can be used in the treatment of disorders associated with defective p53 or p21 function.

In one embodiment, candidate p53 or p21 modulating agents are tested with an assay system comprising a RRP polypeptide or nucleic acid. Candidate agents that produce a change in the activity of the assay system relative to controls are identified as candidate p53 or p21 modulating agents. The assay system may be cell-based or cell-free. Candidate modulating agents include small molecule modulators, antibodies, and nucleic acid modulators. In one specific embodiment, a small molecule modulator is identified using a protease assay. In specific embodiments, the screening assay system is selected from an apoptosis assay, a cell proliferation assay, an angiogenesis assay, and a hypoxic induction assay.

In another embodiment, candidate p53 or p21 pathway modulating agents are further tested using a second assay system that detects changes in the p53 or p21 pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the p53 or p21 pathway, such as an angiogenic, apoptotic, or cell proliferation disorder (e.g. cancer).

The invention further provides methods for modulating the p53 or p21 pathway in a mammalian cell by contacting the mammalian cell with an agent that specifically binds a RRP polypeptide or nucleic acid. The agent may be a small molecule modulator, a nucleic acid modulator, or an antibody and may be administered to a mammalian animal predetermined to have a pathology associated the p53 or p21 pathway.

Modulating agents identified using the methods of the invention can be used to specifically inhibit growth of tumor cells that overexpress an RRP protein.

The invention also provides transgenic knockout mice harboring disrupted RRP genes. The disruption may be heterozygous, leading to decreased expression of RRP, or homozygous, leading to lack of expression of the RRP gene. Cells from the mice as well as cells harboring disrupted RRP genes are also provided. Methods of producing antibody to RRP using the mice of the invention are also provided.

Targeting vectors to produce transgenic knockout mice are also provided. Preferably, a targeting vector is provided that allows sequential deletion of vector sequences from the same cell in the generation of the knockout mice.

BRIEF DESCRIPTION OF THE DRAWINGS

FIG. 4 depicts the target allele after HR, after FLP induced deletion, and after Cre induced deletion. The expected sizes of the genomic fragments after digestion with the indicated restriction enzymes and Southern hybridization are indicated for the target allele in each of the following states: WT, HR, FLP deleted, and Cre deleted.

DETAILED DESCRIPTION OF THE INVENTION

Figure 1:
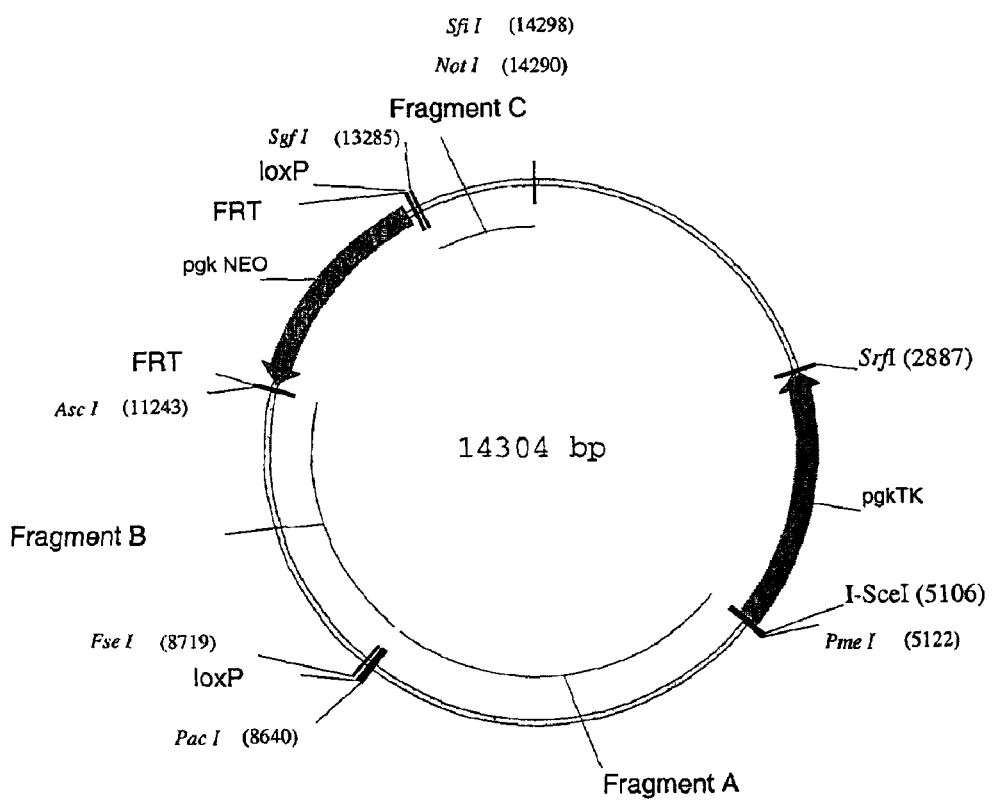
FIG. 1 depicts the targeting vector, pEasyfloxFRTGK12 mRRP1.

Genetic screens were designed to identify modifiers of the p53 or p21 pathways in *Drosophila*. Genetic modifier screens were carried out in which p53 (Ollmann M, et al., Cell 2000 101: 91–101) or p21 (Bourne H R, et al., Nature (1990) 348(6297):125–132; Marshall C J, Trends Genet (1991) 7(3):91–95) were overexpressed. *Drosophila* rhomboid genes were identified as modifiers of the p53 or p21 pathways. Accordingly, vertebrate orthologs of these modifiers, hereinafter referred to as RRP genes (i.e., nucleic acids and polypeptides), are attractive drug targets for the treatment of pathologies associated with a defective p53 or p21 signaling pathways, such as cancer. Further, gene targeting in mice is an ideal method to investigate the function of a distinct protein in wild type and disease states. In order to study the RRP1 function in mammals we generated the genomic sequence of the RRP1 region in mice, deduced its cDNA and protein sequence, and then produced targeted RRP1 knockout (KO) mice.

In vitro and in vivo methods of assessing RRP function as provided herein, and modulation of the RRP or their respective binding partners is useful for understanding the association of the p53 or p21 pathways and their members in normal and disease conditions and for developing diagnostics and therapeutic modalities for p53 or p21 related pathologies. RRP-modulating agents that act by inhibiting or enhancing RRP expression, directly or indirectly, for example, by affecting an RRP function such as enzymatic (e.g., catalytic) or binding activity, can be identified using methods provided herein. RRP-modulating agents include RRP related proteins (e.g. dominant negative mutants, and biotherapeutics); RRP-specific antibodies; RRP-specific antisense oligomers; and chemical agents that specifically bind RRP or compete with RRP binding target. The invention provides methods of identifying and making RRP modulating agents, and their use in diagnosis, therapy and pharmaceutical development.

Preferred RRP-modulating agents specifically bind to RRP polypeptides and enhance or inhibit RRP function. Other preferred RRP-modulating agents are antisense oligomers and RNAi that repress RRP gene expression or product activity by, for example, binding to and inhibiting the respective nucleic acid (i.e. DNA or mRNA). RRP-specific modulating agents may be evaluated by any convenient in vitro or in vivo assay for molecular interaction with an RRP polypeptide or nucleic acid.

The method of this invention is useful in the therapy of malignant or benign tumors of mammals that overexpress RRP gene products.

Nucleic Acids and Polypeptides of the Invention

Sequences related to RRP nucleic acids (RRP1: SEQ ID NO:1, RRP2: SEQ ID NO:3, RRP3: SEQID NO:5, RRP4: SEQ ID NO:7, RRP5: SEQ ID NO:9, RRP6: SEQ ID NO:11, RRP7: SEQ ID NO:13, and RRP8: SEQ ID NO:15) and polypeptides (RRP1: SEQ ID NO:2, RRP2: SEQ ID NO: 4, RRP3: SEQID NO:6, RRP4: SEQ ID NO:8, RRP5: SEQ ID NO:10, RRP6: SEQ ID NO:12, RRP7: SEQ ID NO:14, and RRP8: SEQ ID NO:16) are available in the public databases (for RRP1: cDNA: GI#3287190, SEQ ID NO:18; proteins GI#3287191, SEQ ID NO:36; for RRP2: cDNAs: GI#s: 12762689 (SEQ ID NO:19), 12096415 (SEQ ID NO:20), 6657080 (SEQ ID NO:21), 7947756 (SEQ ID NO:22), 3117010 (SEQ ID NO:23), 9339870 (SEQ ID NO:24), 7152496 (SEQ ID NO:25), 11317512 (SEQ ID NO:26), 11317513 (SEQ ID NO:27), and 11317511 (SEQ ID NO:28); proteins: GI#s:8923409 (SEQ ID NO:37), 12719522 (SEQ ID NO:38), and 11421817 (SEQ ID NO:39); for RRP3: cDNA: GI#10199673 (SEQ ID NO:29) and GI#2003992 (SEQ ID NO:30); for RRP4: cDNA GI#11066249 (SEQ ID NO:31) and protein GI#11066250 (SEQ ID NO:40); for RRP5: cDNA GI#11967982 (SEQ ID NO:32) and protein GI#11967983 (SEQ ID NO:41); for RRP6: cDNA GI#10438685 (SEQ ID NO:33) and protein GI#10438686 (SEQ ID NO:42); for RRP7: cDNA GI#10190733 (SEQ ID NO:34) and protein GI#10190734 (SEQ ID NO:43); and for RRP8: cDNA GI#1 1072100 (SEQ ID NO:35) and protein GI#11072101 (SEQ ID NO:44)). Sequences of human and rat RRP1 were used to deduce the mouse RRP1 (mRRP1) cDNA (SEQ ID NO:45), polypeptide (SEQ ID NO:46), and genomic (SEQ ID NO:47) sequences, as described in Example VII. The mRRP1 cDNA sequence shares 69% identity with human RRP1 and 88% identity with rat partial RRP1 for nucleotides 884–1340 of the mouse RRP1. The mRRP1 protein shares 80% identity with human RRP1 and 88% identity with rat partial RRP1 for amino acids 297–448 of mRRP1.

RRPs are a family of integral membrane proteins that contain five or more transmembrane domains and three strongly conserved histidine residues in the putative transmembrane regions. In a preferred embodiment, the invention provides RRP proteins which comprise or consist of an amino acid sequence of SEQ ID NOs:4, 6, or 46, or fragments or derivatives thereof.

The term "RRP polypeptide" refers to a full-length RRP protein or a functionally active fragment or derivative thereof. A "functionally active" RRP fragment or derivative exhibits one or more functional activities associated with a full-length, wild-type RRP protein, such as antigenic or immunogenic activity, enzymatic activity, ability to bind natural cellular substrates, etc. The functional activity of RRP proteins, derivatives and fragments can be assayed by various methods known to one skilled in the art (Current Protocols in Protein Science (1998) Coligan et al., eds., John Wiley & Sons, Inc., Somerset, N.J.) and as further discussed below. For purposes herein, functionally active fragments also include those fragments that comprise one or more structural domains of an RRP, such as a protease or rhom-boid domain a binding domain. Catalytic and other domains can be identified using the PFAM program (Bateman A., et al., Nucleic Acids Res, 1999, 27:260-2). Methods for obtaining RRP polypeptides are also further described below. Preferred fragments are functionally active, domain-containing fragments sharing at least 80% sequence identity or similarity, preferably at least 85%, more preferably at least 90%, and most preferably at least 95% sequence identity or similarity with a contiguous stretch of at least 25 amino acids, preferably at least 50 amino acids, more preferably at least 100 amino acids, and in some cases, the entire length of any one of SEQ ID NOs:2, 4, 6, 8, 10, 12, 14, 16, and 46. In further preferred embodiments, the fragment comprises the entire rhomboid domain (PFAM 01694).

RRP protein derivatives typically share a certain degree of sequence identity or sequence similarity with SEQ ID NOs:2, 4, 6, 8, 10, 12, 14, 16, or 46 or a fragment thereof. RRP derivatives can be produced by various methods known in the art. The manipulations which result in their production can occur at the gene or protein level. For example, a cloned RRP gene sequence can be cleaved at appropriate sites with restriction endonuclease(s) (Wells et al., Philos. Trans. R. Soc. London SerA (1986) 317:415), followed by further enzymatic modification if desired, isolated, and ligated in vitro, and expressed to produce the desired derivative. Alternatively, an RRP gene can be mutated in vitro or in vivo, to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. (1986) 13:4331), use of TAB® linkers (available from Pharmacia and Upjohn, Kalamazoo, Mich.), etc.

At the protein level, manipulations include post translational modification, e.g. glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known technique (e.g. specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.). Derivative proteins can also be chemically synthesized by use of a peptide synthesizer, for example to introduce nonclassical amino acids or chemical amino acid analogs as substitutions or additions into the RRP protein sequence.

Chimeric or fusion proteins can be made comprising an RRP protein or fragment thereof (preferably comprising one or more structural or functional domains of the RRP protein) joined at its amino- or carboxy-terminus via a peptide bond to an amino acid sequence of a different protein. Chimeric proteins can be produced by any known method, including: recombinant expression of a nucleic acid encoding the protein (comprising a RRP-coding sequence joined in-frame to a coding sequence for a different protein); ligating the appropriate nucleic acid sequences encoding the desired amino acid sequences to each other in the proper coding frame, and expressing the chimeric product; and protein synthetic techniques, e.g. by use of a peptide synthesizer.

The subject RRP polypeptides also encompass minor deletion mutants, including N-, and/or C-terminal truncations. Such deletion mutants are readily screened for RRP competitive or dominant negative activity.

The term "RRP nucleic acid" refers to a DNA or RNA molecule that encodes a RRP polypeptide. In preferred embodiments, the nucleic acid encodes a polypeptide selected from the group consisting of SEQ ID NOs:2, 4, 6, 8, 10, 12, 14, 16, and 46. In some embodiments, the nucleic acid comprises a sequence selected from the group consisting of SEQ ID NO:1, 3, 5, 7, 9, 11, 13, 15, and 45. In a specific embodiment, the invention provides an isolated nucleic acid which encodes a human RRP3 as shown in SEQ ID NO:5, and also an isolated nucleic acid that encodes a mouse RRP (mRRP1) as shown in SEQ ID NO:45.

The invention includes a fragment of a nucleic acid, such as a fragment that encodes a binding domain of one of the full-length sequences of the invention. Fragments of an RRP nucleic acid sequence can be used for a variety of purposes. As an example, interfering RNA (RNAi) fragments, particularly double-stranded (ds) RNAi, can be used to generate loss-of-function phenotypes; which can, in turn, be used, among other uses, to determine gene function. Certain "antisense" fragments, i.e. that are reverse complements of portions of the coding and/or untranslated regions (e.g. 5' UTR) have utility in inhibiting the function of RRP proteins. The fragments are of length sufficient to specifically hybridize with the corresponding RRP sequence. The fragments consist of or comprise at least 12, preferably at least 24, more preferably at least 36, and more preferably at least 96 contiguous nucleotides of RRP. When the fragments are flanked by other nucleic acid sequences, the total length of the combined nucleic acid sequence is less than 15 kb, preferably less than 10 kb or less than 5 kb, more preferably less than 2 kb, and in some cases, preferably less than 500 bases.

In other specific embodiments, preferred fragments of SEQ ID NO:5 encode extracellular or intracellular domains which are located at approximately nucleotides 248–598, 665–796, 862–870, 934–943, 1006–1138, 1201–1225, and 1289–1336. Additional preferred fragments of SEQ ID NO:45 encode extracellular or intracellular domains which are located at approximately nucleotides 1–714, 774–912, 972–984, 1044–1089, 1149–1212, 1272–1305, 1365–1408. Preferred fragments may also include a binding domain or an RRP motif (e.g. PFAM 01694). These domains may be useful to locate the function and/or binding partners of a protein. For example, a nucleic acid that encodes an extracellular or intracellular domain of a protein may be used to screen for binding partners related to the protein.

The subject nucleic acid sequences may consist solely of the RRP nucleic acid or fragments thereof. Alternatively, the subject nucleic acid sequences and fragments thereof may be joined to other components such as labels, peptides, agents that facilitate transport across cell membranes, hybridization-triggered cleavage agents or intercalating agents. The subject nucleic acid sequences and fragments thereof may also be joined to other nucleic acid sequences (i.e. they may comprise part of larger sequences) and are of synthetic/non-natural sequences and/or are isolated and/or are purified, i.e. unaccompanied by at least some of the material with which it is associated in its natural state. Preferably, the isolated nucleic acids constitute at least about 0.5%, and more preferably at least about 5% by weight of the total nucleic acid present in a given fraction, and are preferably recombinant, meaning that they comprise a non-natural sequence or a natural sequence joined to nucleotide(s) other than that which it is joined to on a natural chromosome.

The subject nucleic acids find a wide variety of applications including use as translatable transcripts, hybridization probes, PCR primers, diagnostic nucleic acids, etc.; use in detecting the presence of RRP genes and gene transcripts and in detecting or amplifying nucleic acids encoding additional RRP homologs and structural analogs. In diagnosis, RRP hybridization probes find use in identifying wild-type and mutant RRP alleles in clinical and laboratory samples. Mutant alleles are used to generate allele-specific oligonucleotide (ASO) probes for high-throughput clinical diagnoses. In therapy, therapeutic RRP nucleic acids are used to modulate cellular expression or intracellular concentration or availability of active RRP. In a preferred embodiment, the mouse RRP1 sequence is used to produce a targeting vector for production of mice that are deficient in RRP1 in a heterozygous or homozygous (i.e., knockout) manner.

In one preferred embodiment, the derivative nucleic acid encodes a polypeptide comprising a RRP3 amino acid sequence of SEQ ID NO:6, an mRRP1 amino acid sequence of SEQ ID NO:46, or a fragment or derivative thereof. A derivative RRP3 nucleic acid sequence, or fragment thereof, may comprise 100% sequence identity with SEQ ID NO:5 or 45, but be a derivative thereof in the sense that it has one or more modifications at the base or sugar moiety, or phosphate backbone. Examples of modifications are well known in the art (Bailey, Ullmann's Encyclopedia of Industrial Chemistry (1998), 6th ed. Wiley and Sons). Such derivatives may be used to provide modified stability or any other desired property.

Preferably, the RRP polypeptide nucleic acid, fragment, ortholog, or derivative thereof has at least 70% sequence identity, preferably at least 80%, more preferably 85%, still more preferably 90%, and most preferably at least 95% sequence identity with RRP. Normally, orthologs in different species retain the same function, due to presence of one or more protein motifs and/or 3-dimensional structures. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et at., J. Mol. Biol. (1997) 215:403–410 ) with all the search parameters set to default values. The HSP S and HSP S2 parameters are dynamic values and established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided the local homology algorithm of Smith and Waterman (Smith and Waterman, 1981, Advances in Applied Mathematics 2:482–489; database: European Bioinformatics Institute; Smith and Waterman, 1981, of Molec. Biol., 147:195–197; Nicholas et al., 1998, "A Tutorial on Searching Sequence Databases and Sequence Scoring Methods" and references cited therein.; W. R. Pearson, 1991, Gen mics 11:635–650). This algorithm can be applied to amino acid sequences by using the scoring matrix developed by Dayhoff (Dayhoff: Atlas of Protein Sequences and Structure, M. O. Dayhoff ed., 5 suppl. 3:353–358, National Biomedical Research Foundation, Washington, D.C., USA), and normalized by Gribskov (Gribskov 1986 Nucl. Acids Res. 14(6):6745–6763). The Smith-Waterman algorithm is used to search databases for sequences similar to a query sequence. Smith-Waterman uses dynamic programming to determine how an optimal alignment between the query sequence and a database sequence can be produced. This alignment is obtained by determining what transformations the query sequence would need to undergo to match the database sequence. Transformations include substituting one character for another and inserting or deleting a string of characters. A score is assigned for each character-to-character comparison—positive scores for exact matches and some substitutions, negative scores for other substitutions and insertions/deletion. The first character in an insertion or deletion gap is scored with a gap open penalty and subsequent characters are scored with a gap extension penalty. Scores are obtained from statistically-derived scoring matrices. The combination of transformations that results in the highest score is used to generate an alignment between the query sequence and database sequence. Smith-Waterman algorithm may be employed where default parameters are used for scoring (for example, gap open penalty of 12, gap extension penalty of two). From the data generated the "Match" value reflects "sequence identity."

Derivative nucleic acid molecules of the subject nucleic acid molecules include sequences that hybridize to the nucleic acid sequence of SEQ ID NOs:1, 3, 5, 7, 9, 1, 13, 15, or 45. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs:1, 3, 5, 7, 9, 11, 13, 15, or 45 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18–20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.2×SSC and 0.1% SDS (sodium dodecyl sulfate).

In other embodiments, moderately stringent hybridization conditions are used that comprise: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 μg/ml denatured salmon sperm DNA; hybridization for 18–20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

Isolations, Production, Expression, and Mis-expression of RRP Nucleic Acids and Polypeptides RRP nucleic acids and polypeptides, useful for identifying and testing agents that modulate RRP function and for other applications related to the involvement of RRP in the p53 or p21 pathways. RRP nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of an RRP protein for assays used to assess RRP function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York; U.S. Pat. No. 6,165,992). In particular embodiments, recombinant RRP is expressed in a cell line known to have defective p53 or p21 function (e.g. for p53: SAOS-2 osteoblasts, H1299 lung cancer cells, C33A and HT3 cervical cancer cells, HT-29 and DLD-1 colon cancer cells, among others, and for p21: HCT116 colon cancer cells, among others, available from American Type Culture Collection (ATCC), Manassas, Va.). The recombinant cells are used in cell-based screening assay systems of the invention, as described further below.

The nucleotide sequence encoding an RRP polypeptide can be inserted into any appropriate expression vector. The necessary transcriptional and translational signals, including promoter/enhancer element, can derive from the native RRP gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. A host cell strain that modulates the expression of, modifies, and/or specifically processes the gene product may be used.

To detect expression of the RRP gene product, the expression vector can comprise a promoter operably linked to an RRP gene nucleic acid, one or more origins of replication, and, one or more selectable markers (e.g. thymidine kinase activity, resistance to antibiotics, etc.). Alternatively, recombinant expression vectors can be identified by assaying for the expression of the RRP gene product based on the physical or functional properties of the RRP protein in in vitro assay systems (e.g. immunoassays).

The RRP protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105–111).

Once a recombinant cell that expresses the RRP gene sequence is identified, the gene product can be isolated and purified using standard methods (e.g. ion exchange, affinity, and gel exclusion chromatography; centrifugation; differential solubility; electrophoresis, cite purification reference). Alternatively, native RRP proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of RRP or other genes associated with the p53 or p21 pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter RRP expression may be used in in vivo assays to test for activity of a candidate p53 or p21 modulating agent, or to further assess the role of RRP in a p53 or p21 pathway process such as apoptosis or cell proliferation. Preferably, the altered RRP expression results in a detectable phenotype, such as decreased or increased levels of cell proliferation, angiogenesis, or apoptosis compared to control animals having normal RRP expression. The genetically modified animal may additionally have altered p53 or p21 expression (e.g. p53 or p21 knockout). Preferred genetically modified animals are mammals such as primates, rodents (preferably mice), cows, horses, goats, sheep, pigs, dogs and cats. Preferred non-mammalian species include zebrafish, C. elegans, and Drosophila. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761–763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438–4442 (1985), U.S. Pat. Nos. 4,736,866 and 4,870,009, both by Leder et al., U.S. Pat. No. 4,873,191 by Wagner et al., U.S. Pat. No. 6,127,598, by German et al., and Hogan, B., Manipulating the Mouse Embryo, Cold Spring Harbor Laboratory Press, Cold Spring Harbor, N.Y., (1986); for particle bombardment see U.S. Pat. No. , 4,945,050, by Sandford et al.; for transgenic Drosophila see Rubin and Spradling, Science (1982) 218:348–53 and U.S. Pat. No. 4,670,388; for transgenic insects see Berghammer A. J. et al., A Universal Marker for Transgenic Insects (1999) Nature 402:370–371; for transgenic Zebrafish see Lin S., Transgenic Zebrafish, Methods Mol Biol. (2000);136:375–3830); for microinjection procedures for fish, amphibian eggs and birds see Houdebine and Chourrout, Experientia (1991) 47:897–905; for transgenic rats see Hammer et al., Cell (1990) 63:1099–1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810–813; and PCT International Publication Nos. WO 97/07668 and WO 97/07669).

In one embodiment, the transgenic animal is a "knock-out" animal having a heterozygous or homozygous alteration in the sequence of an endogenous RRP gene that results in a decrease of RRP function, preferably such that RRP expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse RRP gene is used to construct a homologous recombination vector suitable for altering an endogenous RRP gene in the mouse genome as shown in Example VII. Detailed methodologies for homologous recombination in mice are available (see Capecchi, Science (1989) 244:1288–1292; Joyner et al., Nature (1989) 338:153–156). Procedures for the production of non-rodent transgenic mammals and other animals are also available (Houdebine and Chourrout, supra; Pursel et al., Science (1989) 244:1281–1288; Simms et al., Bio/ Technology (1988) 6:179–183). In a preferred embodiment, knock-out animals, such as mice harboring a knockout of a specific gene, may be used to produce antibodies against the human counterpart of the gene that has been knocked out (Claesson M H et al. (1994) Scand J Immunol 40:257–264; Declerck P J, et al., (1995) J Biol Chem 270:8397–8400).

In another embodiment, the transgenic animal is a "knock-in" animal having an alteration in its genome that results in altered expression (e.g., increased (including ectopic) or decreased expression) of the RRP gene, e.g., by introduction of additional copies of RRP, or by operatively inserting a regulatory sequence that provides for altered expression of an endogenous copy of the RRP gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232–6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351–1355; U.S. Pat. No. 5,654,182). In a preferred embodiment, both Cre-LoxP and Flp-Frt are used in the same system to regulate expression of the transgene, and for sequential deletion of vector sequences in the same cell, such as shown in Example VII.

The genetically modified animals can be used in genetic studies to further elucidate the p53 or p21 pathway, as animal models of disease and disorders implicating defective p53 or p21 function, and for in vivo testing of candidate therapeutic agents, such as those identified in the screens described below. Gene targeting in mice is an ideal method to investigate the function of a distinct protein in wild type and disease states. Further, animal models deficient in rhomboid RRP sequence and function are desirable tools for modulating the EGFR signaling pathway, for testing the effect of candidate compounds against RRP, and for production of antibodies against human RRP, among others. The candidate therapeutic agents are administered to a genetically modified animal having altered RRP function and phenotypic changes are compared with appropriate control animals such as genetically modified animals that receive placebo treatment, and/or animals with unaltered RRP expression that receive candidate therapeutic agent.

In additional to the above-described genetically modified animals having altered RRP function, animal models having defective p53 or p21 function (and otherwise normal RRP function), can be used in the methods of the present invention. For example, a p53 or p21 knockout mouse can be used to assess, in vivo, the activity of a candidate p53 or p21 modulatory agent identified in one of the in vitro assays described below. p53 or p21 knockout mice are described in the literature (p53: Jacks et al., Nature 2001;410:1111–1116, 1043–1044; Donehower et al., supra; p21:Umanoff H, et al., Proc Natl Acad Sci USA Feb. 28, 1995; 92(5):1709–13).

Modulating Agents

The invention provides methods to identify agents that interact with and/or modulate the function of RRP and/or the p53 or p21 pathway. Such agents are useful in a variety of diagnostic and therapeutic applications associated with the p53 or p21 pathways, as well as in further analysis of the RRP protein and its contribution to the p53 or p21 pathways. Accordingly, the invention also provides methods for modulating the p53 or p21 pathway comprising the step of specifically modulating RRP activity by administering an RRP-interacting or -modulating agent.

In a preferred embodiment, RRP-modulating agents inhibit or enhance RRP activity or otherwise affect normal RRP function, including transcription, protein expression, protein localization, and cellular or extra-cellular activity. In a further preferred embodiment, the candidate p53 or p21 pathway-modulating agent specifically modulates the function of the RRP. The phrases "specific modulating agent", "specifically modulates", etc., are used herein to refer to modulating agents that directly bind to the RRP polypeptide or nucleic acid, and preferably inhibit, enhance, or otherwise alter, the function of the RRP. The term also encompasses modulating agents that alter the interaction of the RRP with a binding partner or substrate (e.g. by binding to a binding partner of an RRP, or to a protein/binding partner complex, and inhibiting function).

Preferred RRP-modulating agents include small molecule compounds; RRP-interacting proteins, including antibodies and other biotherapeutics; antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., $^{19}$th edition.

Small Molecule Modulators

Small molecules, are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Synthetic compounds may be rationally designed or identified based on known or inferred properties of the RRP protein or may be identified by screening compound libraries. Alternative appropriate modulators of this class are natural products, particularly secondary metabolites from organisms such as plants or fungi, which can also be identified by screening compound libraries for RRP-modulating activity. Methods for generating and obtaining compounds are well known in the art (Schreiber S L, Science (2000) 151: 1964–1969; Radmann J and Gunther J, Science (2000) 151:1947–1948).

Small molecule modulators identified from screening assays, as described below, can be used as lead compounds from which candidate clinical compounds may be designed, optimized, and synthesized. Such clinical compounds may have utility in treating pathologies associated with the p53 or p21 pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific RRP-interacting proteins are useful in a variety of diagnostic and therapeutic applications related to the p53 or p21 pathway and related disorders, as well as in validation assays for other RRP-modulating agents. In a preferred embodiment, RRP-interacting proteins affect normal RRP function, including transcription, protein expression, protein localization, and cellular or extra-cellular activity. In another embodiment, RRP-interacting proteins are useful in detecting and providing information about the function of RRP proteins, as is relevant to p53 or p21 related disorders, such as cancer (e.g., for diagnostic means).

An RRP-interacting protein may be endogenous, i.e. one that naturally interacts genetically or biochemically with an RRP, such as TGFα, EGF, amphiregulin, heregulin, a member of the RRP pathway that modulates RRP expression, localization, and/or activity. RRP-modulators include dominant negative forms of RRP-interacting proteins and of RRP proteins themselves. Yeast two-hybrid and variant screens offer preferred methods for identifying endogenous RRP-interacting proteins (Finley, R. L. et al. (1996) in DNA Cloning-Expression Systems: A Practical Approach, eds. Glover D. & Hames B. D (Oxford University Press, Oxford, England), pp. 169–203; Fashema S F et al., Gene (2000) 250:1–14; Drees B L Curr Opin Chem Biol (1999) 3:64–70; Vidal M and Legrain P Nucleic Acids Res (1999) 27:919–29; and U.S. Pat. No. 5,928,868). Mass spectrometry is an alternative preferred method for the elucidation of protein complexes (reviewed in, e.g., Pandley A and Mann M, Nature (2000) 405:837–846; Yates J R $3^{rd}$, Trends Genet (2000) 16:5–8).

An RRP-interacting protein may be an exogenous protein, such as an RRP-specific antibody or a T-cell antigen receptor (see, e.g., Harlow and Lane (1988) Antibodies, A Laboratory Manual, Cold Spring Harbor Laboratory). RRP antibodies are further discussed below.

In preferred embodiments, an RRP-interacting protein specifically binds an RRP protein. In alternative preferred embodiments an RRP-modulating agent binds an RRP substrate, binding partner, or cofactor.

Antibodies

In another embodiment, the protein modulator is an RRP specific antibody agonist or antagonist. The antibodies have therapeutic and diagnostic utilities, and can be used in screening assays to identify RRP modulators. For example, uses for antibodies include the detection of an RRP protein in a biological sample and the inhibition of RRP activity, for instance, to block the development of an oncogenic disorder. The antibodies can also be used in dissecting the portions of the RRP pathway responsible for various cellular responses and in the general processing and maturation of the RRP.

Antibodies that specifically bind RRP polypeptides can be generated using known methods. Preferably the antibody is specific to a mammalian ortholog of RRP polypeptide, and more preferably, to human RRP. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, Antibodies: A Laboratory Manual, CSH Laboratory (1988); Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of RRP or substantially purified fragments thereof. If RRP fragments are used, they preferably comprise at least 10, and more preferably, at least 20 contiguous amino acids of an RRP protein. In a particular embodiment, RRP-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols. In a preferred embodiment, due to close similarity of RRP sequences from mice and humans, transgenic mice that are RRP deficient or RRP knockout, such as those generated in the present invention (Example VIII), are used to produce antibodies against human RRP.

The presence of RRP-specific antibodies is assayed by an appropriate assay such as a solid phase enzyme-linked immunosorbant assay (ELISA) using immobilized corresponding RRP polypeptides. Other assays, such as radioimmunoassays or fluorescent assays might also be used.

Chimeric antibodies specific to RRP polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851–6855; Neuberger et al., Nature (1984) 312:604–608; Takeda et al., Nature (1985) 31:452–454). Humanized antibodies, which are a form of chimeric antibodies, can be generated by grafting complementary-determining regions (CDRs) (Carlos, T. M., J. M. Harlan. 1994. Blood 84:2068–2101) of mouse antibodies into a background of human framework regions and constant regions by recombinant DNA technology (Riechmann L M, et al., 1988 Nature 323: 323–327). Humanized antibodies contain ~10% murine sequences and ~90% human sequences, and thus further reduce or eliminate immunogenicity, while retaining the antibody specificities (Co MS, and Queen C. 1991 Nature 351: 501–501; Morrison S L. 1992 Ann. Rev. Immun. 10:239–265). Humanized antibodies and methods of their production are well-known in the art (U.S. Pat. No. 5,530,101; U.S. Pat. No. 5,585,089; U.S. Pat. No. 5,693,762, and U.S. Pat. No. 6,180,370).

RRP-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423–426; Huston et al., Proc. Natl. Acad. Sci. USA (1988) 85:5879–5883; and Ward et al., Nature (1989) 334:544–546).

Other suitable techniques for antibody production involve in vitro exposure of lymphocytes to the antigenic polypeptides or alternatively to selection of libraries of antibodies in phage or similar vectors (Huse et al., Science (1989) 246:1275–1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131–134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg—to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml–to about 10 mg/ml. Immunotherapeutic methods are further described in the literature (U.S. Pat. No. 5,859,206; WO0073469).

The selection of an appropriate antibody subclass for therapy will depend upon the nature of the tumor antigen. For example, an IgM may be preferred when the antigen is highly specific for the tumor target and rarely occurs on normal cells. However, the IgG subclass may be preferred when the tumor-associated antigen is also expressed in normal tissues, even at much lower levels. The binding of at least two IgG molecules in close proximity is required to activate complement, a serum protein that combines with antibodies to form a defense against cellular antigens. The normal tissues that express smaller amounts of the antigen and bind fewer IgG molecules may thus incur less complement-mediated damage. Furthermore, since IgGs are smaller than IgMs, they may more readily localize to tumor tissue.

Immune responses may assist in the delivery or efficacy of an anti-tumor treatment. There is evidence that complement activation leads to an inflammatory response and macrophage activation (Uananue and Benecerraf, Textbook of Immunology, 2nd Edition, Williams & Wilkins, p. 218 (1984)). Activated macrophages more preferentially destroy tumor cells than normal cells (Fidler and Poste, Springer Semin. Immunopathol. 5, 161 (1982)). Also, the increased vasodilation accompanying inflammation may increase the ability of anti-cancer agents, such as chemotherapeutic drugs or radiolabeled antibodies to localize in tumors. While a significant detriment of standard chemotherapy or radiation treatment is damage to healthy cells, the antigen-antibody combinations specified by this invention may circumvent many of the problems normally caused by the heterogeneity of tumor cell populations. Additionally, purified antigens (Hakomori, Ann. Rev. Immunol. (1984) 2:103) or the related anti-idiotypic antibodies (Nepom et al., Proc. Natl. Acad. Sci, (1985) 81:2864; Koprowski et al., Proc. Natl. Acad. Sci. (1984) 81:216) which recognize the hypervariance among the same epitopes in different individuals could be used to induce an active immune response in human cancer patients. Such a response includes the formation of antibodies capable of activating human complement and mediating antibody-dependent cell-mediated cytotoxicity and by such mechanisms cause tumor destruction.

Specific Biotherapeutics

In a preferred embodiment, an RRP-interacting protein may have biotherapeutic applications. Biotherapeutic agents formulated in pharmaceutically acceptable carriers and dosages may be used to activate or inhibit signal transduction pathways. This modulation may be accomplished by binding a ligand, thus inhibiting the activity of the pathway; or by binding a receptor, either to inhibit activation of, or to activate, the receptor. Alternatively, the biotherapeutic may itself be a ligand capable of activating or inhibiting a receptor. Biotherapeutic agents and methods of producing them are described in detail in U.S. Pat. No. 6,146,628.

Since RRP is a receptor, its ligand(s), antibodies to the ligand(s) or the RRP itself may be used as biotherapeutics to modulate the activity of RRP in the p53 or p21 pathway.

Nucleic Acid Modulators

Other preferred RRP-modulating agents comprise nucleic acid molecules, such as antisense oligomers or double stranded RNA (dsRNA), which generally inhibit RRP activity.

Preferred antisense oligomers that interfere with the function of the RRP nucleic acid such as DNA replication, transcription, translocation of the RRP RNA to the site of protein translation, translation of protein from the RRP RNA, splicing of the RRP RNA to yield one or more mRNA species, and catalytic activity which may be engaged in or facilitated by the RRP RNA. Double-stranded RNA inhibition (dsRNAi) is another preferred RRP-modulating agent. For convenience, the term "antisense modulator", as used herein, includes antisense oligomers and dsRNAi.

In one embodiment, the antisense oligomer is an oligonucleotide that is sufficiently complementary to an RRP mRNA to bind to and prevent translation, preferably by binding to the 5' untranslated region. RRP-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3) :271–281; Summerton J, and Weller D. 1997 Antisense Nucleic Acid Drug Dev. ;7:187–95, U.S. Pat. No. 5,235,033; and U.S. Pat. No. 5,378,841).

Antisense oligomers are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Antisense oligomers are also used, for example, to distinguish between functions of various members of a biological pathway. Antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923–1937; Tonkinson J L et al., Antisense Oligodeoxynucleotides as Clinical Therapeutic Agents, Cancer Invest. (1996) 14:54–65). Accordingly, in one aspect of the invention, an RRP-specific antisense oligomer is used in an assay to further elucidate the role of the RRP in the p53 or p21 pathway, and/or its relationship to other members of the pathway. In another aspect of the invention, an RRP-specific antisense oligomer is used as a therapeutic agent for treatment of p53 or p21-related disease states.

Alternative preferred RRP-modulating agents are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans, Drosophila*, plants, and humans are known in the art (Fire A, et al., 1998 Nature 391:806–811; Fire, A. Trends Genet. 15, 358–363 (1999); Sharp, P. A. RNA interference 2001. Genes Dev. 15, 485–490 (2001); Hammond, S. M., et al., Nature Rev. Genet. 2, 110–1119 (2001); Tuschl, T. Chem. Biochem. 2, 239–245 (2001); Hamilton, A. et al., Science 286, 950–952 (1999); Hammond, S. M., et al., Nature 404, 293–296 (2000); Zamore, P. D., et al., Cell 101, 25–33 (2000); Bernstein, E., et al., Nature 409, 363–366 (2001); Elbashir, S. M., et al., Genes Dev. 15, 188–200 (2001); WO0129058; WO9932619; Elbashir S M, et al., 2001 Nature 411:494–498).

Assay Systems

The invention provides assay systems for identifying specific modulators of RRP activity. As used herein, an "assay system" encompasses all the components required for performing and analyzing results of an assay that detects and/or measures a particular event. In general, primary assays are used to identify or confirm a modulator's specific biochemical or molecular effect with respect to the RRP nucleic acid or protein. In general, secondary assays further assess the activity of a RRP modulating agent identified by a primary assay and may confirm that the modulating agent affects RRP in a manner relevant to the p53 or p21 pathway. In some cases, RRP modulators will be directly tested in a secondary assay.

In a preferred embodiment, the screening method comprises contacting a suitable assay system comprising an RRP polypeptide with a candidate agent under conditions whereby, but for the presence of the agent, the system provides a reference activity (e.g. protease activity), which is based on the particular molecular event the screening method detects. A statistically significant difference between the agent-biased activity and the reference activity indicates that the candidate agent modulates RRP activity, and hence the p53 or p21 pathway.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384–91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified cellular extracts, or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

In a preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730–4; Fernandes P B, Curr Opin Chem Biol (1998) 2:597–603; Hertzberg R P and Pope A J, Curr Opin Chem Biol (2000) 4:445–451).

Cell-based screening assays usually require systems for recombinant expression of RRP and any auxiliary proteins demanded by the particular assay. Cell-free assays often use recombinantly produced purified or substantially purified proteins. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when RRP-interacting proteins are used in screens to identify small molecule modulators, the binding specificity of the interacting protein to the RRP protein may be assayed by various known methods such as substrate processing (e.g. ability of the candidate RRP-specific binding agents to function as negative effectors in RRP-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit RRP specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a RRP polypeptide, a fusion protein thereof, or to cells or membranes bearing the polypeptide or fusion protein. The RRP polypeptide can be full length or a fragment thereof that retains functional RRP activity. The RRP polypeptide may be fused to another polypeptide, such as a peptide tag for detection or anchoring, or to another tag. The RRP polypeptide is preferably human or mouse RRP, or is an ortholog or derivative thereof as described above. In a preferred embodiment, the screening assay detects candidate agent-based modulation of RRP interaction with a binding target, such as an endogenous or exogenous protein or other substrate that has RRP-specific binding activity, and can be used to assess normal RRP gene function.

Suitable assay formats that may be adapted to screen for RRP modulators are known in the art. Preferred screening assays are high throughput or ultra high throughput and thus provide automated, cost-effective means of screening compound libraries for lead compounds (Fernandes P B, 1998, supra; Sundberg S A, Curr Opin Biotechnol 2000, 11:47–53).

A variety of suitable assay systems may be used to identify candidate RRP and p53 or p21 pathway modulators (e.g. U.S. Pat. No. 6,020,135 (p53 modulation), U.S. Pat. No. 6,114,132 (phosphatase and protease assays)). Specific preferred assays are described in more detail below.

Protease Assays. Proteases are enzymes that cleave protein substrates at specific sites. Exemplary assays detect the alterations in the spectral properties of an artificial substrate that occur upon protease-mediated cleavage. In one example, synthetic caspase substrates containing four amino acid proteolysis recognition sequences, separating two different fluorescent tags are employed; fluorescence resonance energy transfer detects the proximity of these fluorophores, which indicates whether the substrate is cleaved (Mahajan N P et al., Chem Biol (1999) 6:401–409).

Endogenous protease inhibitors may inhibit protease activity. In an example of an assay developed for either proteases or protease inhibitors, a biotinylated substrate is coated on a titer plate and hydrolyzed with the protease; the unhydrolyzed substrate is quantified by reaction with alkaline phosphatase-streptavidin complex and detection of the reaction product. The activity of protease inhibitors correlates with the activity of the alkaline phosphatase indicator enzyme (Gan Z et al., Anal Biochem 1999) 268:151–156).

Apoptosis assays. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730–41). An apoptosis assay system may comprise a cell that expresses an RRP, and that optionally has defective p53 or p21 function (e.g. p53 or p21 is over-expressed or under-expressed relative to wild-type cells). A test agent can be added to the apoptosis assay system and changes in induction of apoptosis relative to controls where no test agent is added, identify candidate p53 or p21 modulating agents. In some embodiments of the invention, an apoptosis assay may be used as a secondary assay to test a candidate p53 or p21 modulating agents that is initially identified using a cell-free assay system. An apoptosis assay may also be used to test whether RRP function plays a direct role in apoptosis. For example, an apoptosis assay may be performed on cells that over- or under-express RRP relative to wild type cells. Differences in apoptotic response compared to wild type cells suggests that the RRP plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell Proliferation may also be examined using [$^3$H]-thymidine incorporation (Chen, J., 1996, Oncogene 13:1395–403; Jeoung, J., 1995, J. Biol. Chem. 270:18367–73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman L S 3800 Liquid Scintillation Counter).

Cell proliferation may also be assayed by colony formation in soft agar (Sambrook et al., Molecular Cloning, Cold Spring Harbor (1989)). For example, cells transformed with RRP are seeded in soft agar plates, and colonies are measured and counted after two weeks incubation.

Involvement of a gene in the cell cycle may be assayed by flow cytometry. Cells transfected with an RRP may be stained with propidium iodide and evaluated in a flow cytometer (available from Becton Dickinson).

Accordingly, a cell proliferation or cell cycle assay system may comprise a cell that expresses an RRP, and that optionally has defective p53 or p21 function (e.g. p53 or p21 is over-expressed or under-expressed relative to wild-type cells). A test agent can be added to the assay system and changes in cell proliferation or cell cycle relative to controls where no test agent is added, identify candidate p53 or p21 modulating agents. In some embodiments of the invention, the cell proliferation or cell cycle assay may be used as a secondary assay to test a candidate p53 or p21 modulating agents that is initially identified using another assay system such as a cell-free kinase assay system. A cell proliferation assay may also be used to test whether RRP function plays a direct role in cell proliferation or cell cycle. For example, a cell proliferation or cell cycle assay may be performed on cells that over- or under-express RRP relative to wild type cells. Differences in proliferation or cell cycle compared to wild type cells suggests that the RRP plays a direct role in cell proliferation or cell cycle. A cell proliferation assay may also be used to identify candidate agents that modulate cell proliferation. For example, cells that have decreased expression of RRP or that are RRP knockouts, such as mouse cells generated in the present invention (Example VIII) are treated with candidate agents. Changes in cell proliferation relative to control cells where no agent is added indicate that the candidate agent modulates cell proliferation.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses an RRP, and that optionally has defective p53 or p21 function (e.g. p53 or p21 is over-expressed or under-expressed relative to wild-type cells). A test agent can be added to the angiogenesis assay system and changes in angiogenesis relative to controls where no test agent is added, identify candidate p53 or p21 modulating agents. In some embodiments of the invention, the angiogenesis assay may be used as a secondary assay to test a candidate p53 or p21 modulating agents that is initially identified using another assay system. An angiogenesis assay may also be used to test whether RRP function plays a direct role in cell proliferation. For example, an angiogenesis assay may be performed on cells that over- or under-express RRP relative to wild type cells. Differences in angiogenesis compared to wild type cells suggests that the RRP plays a direct role in angiogenesis.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumor cell survival, such as those encoding glyolytic enzymes and VEGF. Induction of such genes by hypoxic conditions may be assayed by growing cells transfected with RRP in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses an RRP, and that optionally has a mutated p53 or p21 (e.g. p53 or p21 is over-expressed or under-expressed relative to wild-type cells). A test agent can be added to the hypoxic induction assay system and changes in hypoxic response relative to controls where no test agent is added, identify candidate p53 or p21 modulating agents. In some embodiments of the invention, the hypoxic induction assay may be used as a secondary assay to test a candidate p53 or p21 modulating agents that is initially identified using another assay system. A hypoxic induction assay may also be used to test whether RRP function plays a direct role in the hypoxic response. For example, a hypoxic induction assay may be performed on cells that over- or under-express RRP relative to wild type cells. Differences in hypoxic response compared to wild type cells suggest that the RRP plays a direct role in hypoxic induction.

Cell adhesion. Cell adhesion assays measure adhesion of cells to purified adhesion proteins, or adhesion of cells to each other, in presence or absence of candidate modulating agents.

Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May–Jun;12(3):346–53).

Certain screening assays may also be used to test antibody and nucleic acid modulators; for nucleic acid modulators, appropriate assay systems involve RRP mRNA expression.

Primary Assays for Antibody Modulators

For antibody modulators, appropriate primary assays test is a binding assay that tests the antibody's affinity to and specificity for the RRP protein. Methods for testing antibody affinity and specificity are well known in the art (Harlow and Lane, 1988, 1999, supra). The enzyme-linked immunosorbant assay (ELISA) is a preferred method for detecting RRP-specific antibodies; others include FACS assays, radioimmunoassays, and fluorescent assays.

Primary Assays for Nucleic Acid Modulators

For nucleic acid modulators, primary assays may test the ability of the nucleic acid modulator to inhibit or enhance RRP gene expression, preferably mRNA expression. In general, expression analysis comprises comparing RRP expression in like populations of cells (e.g., two pools of cells that endogenously or recombinantly express RRP) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that RRP mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; Blohm D H and Guiseppi-Elie, A Curr Opin Biotechnol 2001, 12:41–47). Protein expression may also be monitored. Proteins are most commonly detected with specific antibodies or antisera directed against either the RRP protein or specific peptides. A variety of means including Western blotting, ELISA, or in situ detection, are available (Harlow E and Lane D, 1988 and 1999, supra).

Secondary Assays

Secondary assays may be used to further assess the activity of RRP-modulating agent identified by any of the above methods to confirm that the modulating agent affects RRP in a manner relevant to the p53 or p21 pathway. As used herein, RRP-modulating agents encompass candidate clinical compounds or other agents derived from previously identified modulating agent. Secondary assays can also be used to test the activity of a modulator on a particular genetic or biochemical pathway or to test the specificity of the modulator's interaction with RRP.

Secondary assays generally compare like populations of cells or animals (e.g., two pools of cells or animals that endogenously or recombinantly express RRP) in the presence and absence of the candidate modulator. In general, such assays test whether treatment of cells or animals with a candidate RRP-modulating agent results in changes in the p53 or p21 pathway in comparison to untreated (or mock- or placebo-treated) cells or animals. Certain assays use "sensitized genetic backgrounds", which, as used herein, describe cells or animals engineered for altered expression of genes in the p53 or p21 or interacting pathways.

Cell-based Assays

Cell based assays may use a variety of mammalian cell lines known to have defective p53 or p21 function (e.g. for p53: SAOS-2 osteoblasts, H1299 lung cancer cells, C33A and HT3 cervical cancer cells, HT-29 and DLD-1 colon cancer cells, among others, and for p21: HCT116 colon cancer cells, among others, available from American Type Culture Collection (ATCC), Manassas, Va.). Cell based assays may detect endogenous p53 or p21 pathway activity or may rely on recombinant expression of p53 or p21 pathway components. Any of the aforementioned assays may be used in this cell-based format. Candidate modulators are typically added to the cell media but may also be injected into cells or delivered by any other efficacious means.

Animal Assays

A variety of non-human animal models of normal or defective p53 or p21 pathway may be used to test candidate RRP modulators. Models for defective p53 or p21 pathway typically use genetically modified animals that have been engineered to mis-express (e.g., over-express or lack expression in) genes involved in the p53 or p21 pathway. Assays generally require systemic delivery of the candidate modulators, such as by oral administration, injection, etc.

In a preferred embodiment, p53 or p21 pathway activity is assessed by monitoring neovascularization and angiogenesis. Animal models with defective and normal p53 or p21 are used to test the candidate modulator's affect on RRP in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the RRP. The mixture is then injected subcutaneously into the female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5–12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on RRP is assessed via tumorigenicity assays. In one example, xenograft human tumors are implanted subcutaneously (SC) into female athumic nude mice, 6–7 week old, as single cell suspensions either from a pre-existing tumor or from in vitro culture. The tumors which express the RRP endogenously are injected in the flank, $1 \times 10^5$ to $1 \times 10^7$ cells per mouse in a volume of 100 μL using a 27 gauge needle. Mice are then ear tagged and tumors are measured twice weekly. Candidate modulator treatment is initiated on the day the mean tumor weight reaches 100 mg. Candidate modulator is delivered intravenously (IV), subcutaneously (SC), intraperitoneously (IP), or orally (PO) by bolus administration. Depending upon the pharmacokinetics (PK) of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohischemistry staining, xenograft tumors are fixed in 4% paraformaldehyde, 0.1M phosphate, PH 7.2, for 6 hours at 4° C., immersed in 30% sucrose in PBS, and rapidly frozen in isopetane cooled with liquid nitrogen.

Diagnostic and Therapeutic Uses

Specific RRP-modulating agents are useful in a variety of diagnostic and therapeutic applications where disease or disease prognosis is related to defects in the p53 or p21 pathway, such as angiogenic, apoptotic, or cell proliferation disorders. Accordingly, the invention also provides methods for modulating the p53 or p21 pathway in a cell, preferably a cell pre-determined to have defective p53 or p21 function, comprising the step of administering an agent to the cell that specifically modulates RRP activity.

The discovery that RRP is implicated in p53 or p21 pathway provides for a variety of methods that can be employed for the diagnostic and prognostic evaluation of diseases and disorders involving defects in the p53 or p21 pathway and for the identification of subjects having a predisposition to such diseases and disorders.

Various expression analysis methods can be used to diagnose whether RRP expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; Blohm and Guiseppi-Elie, Curr Opin Biotechnol 2001, 12:41–47). Tissues having a disease or disorder implicating defective p53 or p21 signaling that express an RRP, are identified as amenable to treatment with an RRP modulating agent. In a preferred application, the p53 or p21 defective tissue overexpresses an RRP relative to normal tissue. For example, a Northern blot analysis of mRNA from tumor and normal cell lines, or from tumor and matching normal tissue samples from the same patient, using full or partial RRP cDNA sequences as probes, can determine whether particular tumors express or overexpress RRP. Alternatively, the TaqMan® is used for quantitative RT-PCR analysis of RRP expression in cell lines, normal tissues and tumor samples (PE Applied Biosystems).

Various other diagnostic methods may be performed, for example, utilizing reagents such as the RRP oligonucleotides, and antibodies directed against an RRP, as described above for: (1) the detection of the presence of RRP gene mutations, or the detection of either over- or under-expression of RRP mRNA relative to the non-disorder state; (2) the detection of either an over- or an under-abundance of RRP gene product relative to the non-disorder state; and (3) the detection of perturbations or abnormalities in the signal transduction pathway mediated by RRP.

Thus, in a specific embodiment, the invention is drawn to a method for diagnosing a disease in a patient, the method comprising: a) obtaining a biological sample from the patient; b) contacting the sample with a probe for RRP expression; c) comparing results from step (b) with a control; and d) determining whether step (c) indicates a likelihood of disease. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *Drosophila* p53 and p21 Screens

The *Drosophila* p53 gene was overexpressed specifically in the wing using the vestigial margin quadrant enhancer. Increasing quantities of *Drosophila* p53 (titrated using different strength transgenic inserts in 1 or 2 copies) caused deterioration of normal wing morphology from mild to strong, with phenotypes including disruption of pattern and polarity of wing hairs, shortening and thickening of wing veins, progressive crumpling of the wing and appearance of dark "death" inclusions in wing blade. In a screen designed to identify enhancers and suppressors of *Drosophila* p53, homozygous females carrying two copies of p53 were crossed to 5663 males carrying random insertions of a piggyBac transposon (Fraser M et al., Virology (1985)

145:356–361). Progeny containing insertions were compared to non-insertion-bearing sibling progeny for enhancement or suppression of the p53 phenotypes. Sequence information surrounding the piggyBac insertion site was used to identify the modifier genes. Modifiers of the wing phenotype were identified as members of the p53 pathway.

An overexpression screen was carried out in *Drosophila* to identify genes that interact with the cyclin dependent kinase inhibitor, p21 (Bourne H R, et al., Nature (1990) 348(6297):125–132; Marshall C J, Trends Genet (1991) 7(3):91–95). Expression of the p21 gene in the eye causes deterioration of normal eye morphology. Modifiers of the eye phenotype were identified as members of the p21 pathway.

II. High-Throughput In Vitro Fluorescence Polarization Assay

Fluorescently-labeled RRP peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of RRP activity.

III. High-Throughput In Vitro Binding Assay.

$^{33}$P-labeled RRP peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate p53 or p21 modulating agents.

IV. Immunoprecipitations and Immunoblotting

For coprecipitation of transfected proteins, 3×10$^6$ appropriate recombinant cells containing the RRP proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Expression Analysis

All cell lines used in the following experiments are NCI (National Cancer Institute) lines, and are available from ATCC (American Type Culture Collection, Manassas, Va. 20110–2209). Normal and tumor tissues were obtained from Impath, UC Davis, Clontech, Stratagene, and Ambion.

TaqMan analysis was used to assess expression levels of the disclosed genes in various samples.

RNA was extracted from each tissue sample using Qiagen (Valencia, Calif.) RNeasy kits, following manufacturer's protocols, to a final concentration of 50ng/µl. Single stranded cDNA was then synthesized by reverse transcribing the RNA samples using random hexamers and 500 ng of total RNA per reaction, following protocol 4304965 of Applied Biosystems (Foster City, Calif.).

Primers for expression analysis using TaqMan assay (Applied Biosystems, Foster City, Calif.) were prepared according to the TaqMan protocols, and the following criteria: a) primer pairs were designed to span introns to eliminate genomic contamination, and b) each primer pair produced only one product.

Taqman reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples) >2×STDEV(all normal samples)).

Results are shown in Table 1. Data presented in bold indicate that greater than 50% of tested tumor samples of the tissue type indicated in row 1 exhibited over expression of the gene listed in column 1, relative to normal samples. Underlined data indicates that between 25% to 49% of tested tumor samples exhibited over expression. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE I

| Gene Name | Breast Matched | Breast Total | Colon Matched | Lung Matched | Ovary Matched | Ovary Total | Kidney Matched |
|---|---|---|---|---|---|---|---|
| RRP1 | 0/3 | 0/5 | 11/26 | 8/14 | 1/4 | 3/14 | 2/19 |
| RRP2 | 1/3 | 1/5 | 3/26 | 7/14 | 2/4 | 9/14 | 12/19 |
| RRP3 | 0/3 | 0/5 | 4/26 | 4/14 | 1/4 | 3/14 | 4/19 |
| RRP4 | 0/3 | 0/5 | 3/26 | 3/14 | 1/4 | 5/14 | 4/19 |
| RRP5 | 0/3 | 0/5 | 6/26 | 1/14 | 1/4 | 1/14 | 4/19 |
| RRP6 | 2/3 | 3/5 | 10/26 | 5/14 | 0/4 | 0/14 | 13/19 |
| RRP7 | 0/3 | 0/5 | 6/26 | 1/14 | 1/4 | 1/14 | 1/19 |
| RRP8 | 1/3 | 1/5 | 6/26 | 5/14 | 0/4 | 0/14 | 3/19 |

VI. Cell Biology and Functional Characterization

RRP Localization. In *Drosophila*, rhomboid is a cell surface protein. However, localization of human RRPs has not happened to date. Furthermore, in humans, it is not known whether each of the termini of the rhomboids is intracellular or extracellular. To answer these questions, RRP1 was subcloned into pcDNA expression vector (Invitrogen) in frame with myc-his tag at the c-terminus, according to manufacturer's protocols. The resulting expression vector was transiently transfected using Lipofectamine Plus reagent (Life technologies) into human embryonic kidney HEK-293 cells. Immunofluorescence staining using anti-myc antibody was then carried out on the cells to localize RRP1. Results of these experiments indicated that RRP1 is expressed at the cell surface. Furthermore, permeabilized (0.1% triton in PBS) and non-permeabilized cells show the same staining pattern, indicating that the c-terminus of the protein is outside, and the N-terminus, inside. RRP2–RRP8 are also subcloned and tagged at the c-terminus for localization of each protein, and also to assess the direction of the protein ends in each case.

Involvement of RRP in EGFR signaling pathway. While *Drosophila* rhomboid is essential in the EGFR pathway, the function of human RRPs have not been assessed to date. To assess the role of human RRPs in the EGFR signaling pathway, RRP1 was stably transfected using CaPO4 transfection kit (Clontech) into Hela cells, which have endogenous EGFR activity. Pooled stable cells were then examined in the following assays.

EGFR Activation as Measured by Tyrosine Phosphorylation

Hela cells overexpressing RRP1 and parental Hela cells were tested for EGFR tyrosine phosphorylation by immunoblot against anti-phosphotyrosine using anti-phosphotyrosine antibody (Upstate Biotechnology). Cells overexpressing RRP1 demonstrated up to two-fold increase in EGFR tyrosine phosphorylation as compared to parental Hela controls.

EGFR Expression in Cells Overexpressing RRP1.

Expression of EGFR was increased when tested by immunoblot using anti-EGFR antibody against direct cell lysates in cells overexpressing RRP1. Furthermore, expression of EGFR was also increased in tumor samples overexpressing RRP1, by TaqMan® analysis. The correlation of both in-vitro and in-vivo results for concordant overexpression of EGFR and RRP1 is quite significant, and provides a tool for assessing the functional relationship of the two proteins in any tumor sample or cell line.

Cell Proliferation and Migration.

Hela cells overexpressing RRP1 demonstrate a two-fold increase in cell proliferation compared to Hela parental cells as measured by Procheck (Intergen) and AlamarBlue (Biosource International) chemiluminescent assays. In addition, Fluroblok (BD Biosource) analysis showed a slight increase in motility in cells overexpressing RRP1 compared to Hela parental cells.

Taken together, these results demonstrate a strong functional conservation of rhomboids across evolution. Furthermore, increased RRP1 expression in tumor samples and cell lines, concurrent increased expression of EGFR, and increased proliferation and motility of cells expressing RRP1 suggest involvement of RRP1 in various cancers. RRP1 expression levels can thus be used to screen for tumors with defective EGFR pathways, to identify tumors amenable to treatment with the compounds and antibodies identified by the methods of the present invention. Same aforementioned experiments are performed with RRP2-RRP8 to assess their involvement in the EGFR signaling pathway.

RRP1 binding target. In *Drosophila*, rhomboid transforms Spitz (homolog of human TGF-α) from a membrane-bound to a secreted form, and thus triggers and upregulates the DER (*Drosophila* EGFR) pathway. No such function has been shown for human rhomboids. HEK293 cells were transiently co-transfected with RRP1 and TM-TGF-α transmembrane-bound TGF), then immunoprecipitated with anti-myc antibody (for RRP1) and immunoblotted with anti-TGF-α. Cells transfected with vector alone, RRP1 alone, or TM-TGF-α, alone were used as controls. A band corresponding to the size of TGF-α was recognized by anti-TGF-α antibody, while no bands were detected in the control lanes. This data indicates that RRP1 physically interacts with TGF-α. The same experiments are performed with RRP2-RRP8 to determine their binding partners.

Antibodies against human rhomboids. A peptide antibody, SEQ ID NO: 17, and referred to as peptide 1, was made against the N-terminus of RRP1. This antibody displayed strong affinity for denatured RRP1, such as in cells fixed with formalin or proteins on western blots. In addition, staining pattern remained the same when permeabilized cells were co-stained with anti-myc antibodies (for the c-terminus of RRP1) and peptide 1, suggesting that Peptide 1 does recognize RRP1. Furthermore, the cells were significantly immunostained only when they were permeabilized, suggesting that the N-terminus of RRP1 is inside the cells. This result correlates with the previous staining pattern using anti-myc antibody for the C-terminus.

RRP1 protein expression in tumors was examined by Immunohistochemistry (IHC) using peptide 1. Positive staining on epithelial cells of colon adenocarcinoma tissue sections were observed as compared to background staining in preimmune serum, suggesting the antibody is specific for its target, RRP1, in colon cancer cells. Moreover, increased staining of colorectal adenocarcinomas was observed compared to matched normal tissues using peptide 1 antibody.

Taken together, these results suggest that peptide 1 antibody is a powerful tool to assess expression levels of RRP1 in tumor samples. Antibodies are also produced against the rest of RRPs to assess their expression levels in tumors.

VII. Mouse RRP1 (mRRP1) Gene Structure

A BAC shotgun sequencing approach (for a review, see Green E D. (2001) Nature Review Genetics 2:573–583) was used to determine the intron-exon structure of the murine RRP1 gene. Based upon the genebank entries of a partial rat cDNA and the human gene structure, a PCR primer pair was designed that allowed the amplification of a part of the murine RRP1 gene from mouse genomic DNA. (RRP1s (SEQ ID NO:48): 5'-CACCCACCAGCCGCACTGGTC; RRP8as (SEQ ID NO:49): 5'-GAGCAGCTAGGGTTCAATG, 95° C. 120 sec, 95° C. 45 sec, 60° C. 45 sec, 72° C. 45 sec, 40 cycles, 1.5 mM MgCl2). This PCR primer set was then used to screen a commercially available ES-129SvJ BAC library from Incyte Genomics (St. Louis, USA). 2 PCR positive clones were identified (clone addresses 178/O15 and 195/D15). Clone 195/D15 was chosen to construct a shotgun sequencing library according to standard procedures (TOPO Shotgun Subcloning Kit, #K-7000-01, Invitrogen). Upon sequence assembly, a contiguous 30 Kilobases (kb) genomic sequence was identified that carried the entire mRRP1 gene. Subsequently, the DNA from clone 195/D15 BAC served as a PCR template to amplify mRRP1 genomic regions used for the gene targeting approach. The mRRP1 gene contains 8 exons, which span a genomic region of at least 2.6 kb. The translation start on the sequence stretch defined as exon 1 has not been identified so that additional 5' exons may exist.

VIII. Generation of the Mice

Targeting Strategy

We utilized a targeting strategy that allows sequential deletion of vector sequences in the same cells. Chimeras generated by injection of mRRP1 targeted ES-cells can be used to create i) KO mice harboring a completely inactivated mRRP gene by breeding to Cre-deleter mice (described below) as well as ii) mice with functional mRRP1 that can be deleted in a tissue specific or time specific manner by breeding to FLP-deleter mice (described below).

This strategy has the advantage that the NEO selection cassette is removed in both chimeras, thus avoiding potential hypomorphic effect of the selection marker.

Targeting Vector

The targeting vector, comprising the nucleotide sequence to be incorporated into the wild-type (WT) genomic sequence, and one or more selectable markers (FIG. 1) was made based on a BAC genomic clone from the mouse strain 129SvJ background obtained from Incyte Genomics. The mRRP1 targeting vector was designed such that exons 2–8 of the mRRP1 gene were flanked with Cre recombinase recognition sequences (loxP sites) after homologous recombination. Exons 2–8 of the murine RRP encode the rhomboid domain which provide protein activity, therefore a deletion of exons 2–8 results in a null allele. Three genomic fragments were amplified by PCR and cloned individually in reversed orientation into the base vector pEasyflox-FRTGK12 (FIG. 1). This base vector has: an ampicillin resistance gene; an orign of replication; a pgtN29 plasmid (New England Biolabs), used as the source of pgk neo; pGT60mcs plasmid (InvivoGen), used as the source for TK reading frame; and LoxP and FRT sites, introduced by synthetic oligonucleotides. The 5' region of homology (fragment A) amplified with oligo 164 (SEQ ID NO:62) and oligo 144 (SEQ ID NO:50) covered a 3.5 kb fragment that was inserted into PacI/PmeI sites upstream the $2^{nd}$ loxP site of pEasyfloxFRTGK12. A 2.5 kb 3' fragment encompassing exons 2–8 (fragment B) and amplified with oligos 145 (SEQ ID NO:51) and 146 (SEQ ID NO:52) was cloned into a AscI/FseI I sites downstream of $2^{nd}$ loxP site and upstream of $2^{nd}$ FRT site and PGK-neo cassette of pEasyflox-FRTGK12. An additional 1.0 kb fragment further 3' (fragment C) and amplified with oligos 147 (SEQ ID NO:53) and 148 (SEQ ID NO:54) was inserted into NotI/SgfI sites located downstream the $1^{st}$ FRT and $1^{st}$ loxP site of pEasyfloxFRTGK12. The loxP- and FRT-flanked neomycin resistance cassette downstream of exons 2–8 of the RRP gene allowed genomic selection for homologous recombination and a PGK-thymidine kinase gene cassette (PGK-TK) inserted at the 5' end of the construct was used to select against random integration events.

In order to establish a positive control for the PCR screen on ES cell clones showing homologous recombination events, an additional 1.25 kb fragment was amplified using oligo 147 (SEQ ID NO:53) and oligo 149 (SEQ ID NO:55) and cloned into NotI/SgfI sites in pEasyfloxFRTGK12. This fragment extended the 3' homology region of the final targeting vector by 250 base pairs, allowing establishment of PCR screening with a vector specific oligo 174 (SEQ ID NO:64) and RRP gene specific oligo 169 (SEQ ID NO:63) located 3' external in relation to the targeting vector.

Generation of Targeted ES-cells

Three parental embryonic stem (ES) cell lines B6-2 (EUROGENETEC, Ref: TG-ES01-02, derived from mouse strain C57BL/6 N TacfBr), SvEv (EUROGENETEC, Ref: TG-ES01-01, derived from mouse strain 129S6/SvEvTacfBr), and E-14 ((Hooper et al., (1987) *Nature (London)* 326, 292–295); derived from mouse strain 129P2/OlaHsd) were employed for targeting of the mRRP1 locus.

All ES cell lines were cultured and electroporated under the conditions described in Torres, R. M. & Kuehn, R. Laboratory Protocols for Conditional Gene Targeting, *Oxford, New York, Tokyo:* 1997. In brief, for electroporation $1×10^7$ cells were mixed with 30 µg of SfiI linearized targeting DNA in a total volume of 800 µl transtection buffer and electroporated using a Bio-Rad Gene Pulser (0,24 kV, 500 µF, 0,4 cm electrode distance). Cells were reseeded on 10-cm tissue culture dishes, containing selection resistant mouse embryonic fibroblast feeder cells (prepared from targeted mouse strain L4 pepneo; Mueller et al., (1992) *Eur. J. Immunol.* 21: 921–25) at a density of $2.5×10^6$ cells per plate. Drug selection (G418 (Gibco/BRL #10131–019)), 200 mg/ml) was started after 1 day. ES cell clones were negatively selected the $3^{rd}$ day after electroporation with the antibiotic Gancyclovir (Cymeven, Roche), 2 µM). After 8 days, resistant colonies were randomly picked and individually expanded. Correctly targeted ES clones were obtained for all 3 ES cell lines employed in the experiment.

Figure 2:
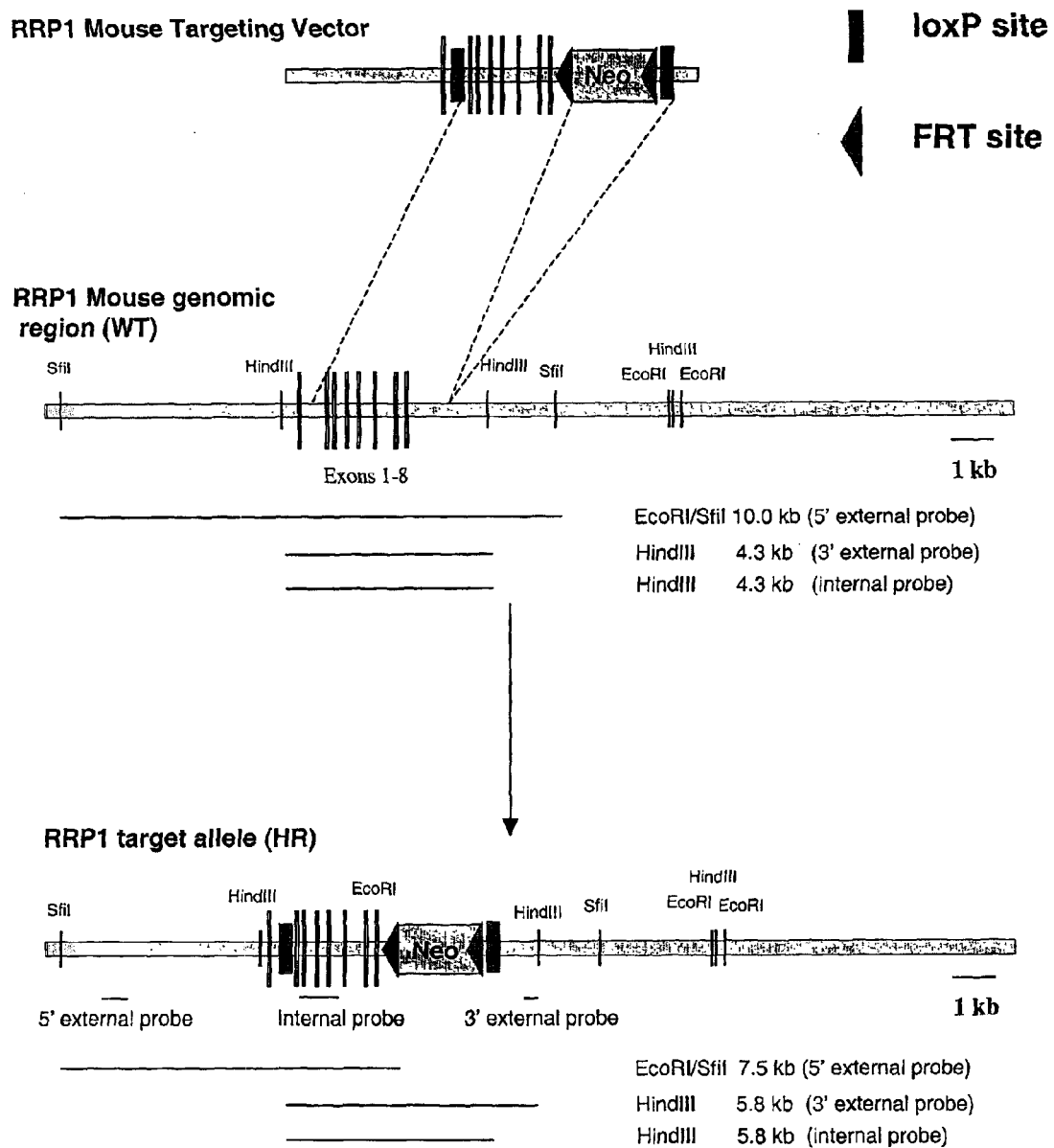
FIG. 2 shows the mRRP1 mouse targeting vector, the mRRP1 wild type (WT) genomic region and the locations to which the vector is targeted, and the mRRP1 target allele after homologous recombination (HR). Locations of the 5' external probe, the internal probe, and the 3' external probe are underlined. The expected sizes of the genomic fragments after digestion with the indicated restriction enzymes and Southern hybridization are also indicated.

Successful targeting of the mRRP gene was detected in resistant ES clones by PCR-screening with primer oligo 174 (SEQ ID NO:64) and oligo 169 (SEQ ID NO:63). Corecombination of the distal loxP site was detected by using oligo 200 (SEQ ID NO:65) and oligo 201 (SEQ ID NO:66). PCR-positive clones were expanded and confirmed by EcoRI/SfiI restriction enzyme digestion and Southern hybridization employing the 5' external probe amplified with oligos 152 (SEQ ID NO:56) and 153 (SEQ ID NO:57). Upon homologous recombination, the wild type 10.0 kb band was reduced to 7.5 kb (FIG. 2). Corecombination of the $2^{nd}$ loxP site in homologous recombinants was confirmed by HindIII and 3' external probe amplified with oligos 160 (SEQ ID NO:60) and 162 (SEQ ID NO:61)(FIG. 2). Upon corecombination of the $2^{nd}$ loxP site, the wildtype 4.3 kb band was increased to 5.8 kb (FIG. 2). Single integration of the targeting vector was confirmed by HindIII digestion and Southern hybridization using the internal probe amplified with oligos 154 (SEQ ID NO:58) and 155 (SEQ ID NO:59) (FIG. 2).

Table 2 provides a summary of these experiments.

TABLE 2

Homologous recombination of the RRP-1 targeting construct in various ES cells

| ES Cell | strain | # cells × $10^7$ | G418 res. Clones | anal. | HR | 2.loxP # | Clone |
|---|---|---|---|---|---|---|---|
| B6-2 | C57BL/6 | 4 | 2000 | 876 | 3 | 2 | G-D5 E-D9 |
| SvEv | 129S6 | 2 | Not counted | 95 | 1 | 0 | |
| | | 3 | Not counted | 295 | 1 | 1 | D-E7 |
| E-14 | 129P2 | 6 | Not counted | 641 | 11 | 3 | B-E2 E-F2 C-C8 |

Generation of mRRP1 Chimeras

Chimeras were generated by injection of targeted ES cells into Balb/C host embryos (Hogan, B., Beddington, R., Costantini, F. & Lacy, E. eds. Manipulating the Mouse Embryo, a Laboratory Manual. $2^{nd}$ ed. Cold Spring Harbor, N.Y.: Cold Spring Harbor, Laboratory Press, 1994). Germline transmission was obtained by breeding chimeric mice to C57BL/6 females, resulting in mRRP1 heterozygous animals on a pure C57BL/6 strain background and hybrid (C57B/L6×129SvEv)$_{F1}$ and (C57B/L6×129P2/Ola)$_{F1}$ background.

Resulting animals were typed by Southern blot hybridization on tail DNA after digestion with HindIII with the 3' external probe. In heterozygote animals for the target allele, the 4.3 kb wild type band was increased to 5.8 kb.

Table 3 provides a summary of these experiments.

TABLE 3

Summary of chimera production and germline transmission of the target

| Clone | blastocysts transf. | pups born | # of chimeras | GL transmis.. | heterozyg mice |
|---|---|---|---|---|---|
| B6-2 | | | | | |
| G-D5 | 246 | 37 | 32 | 10/11 | yes |
| E-D9 | 372 | 103 | 70 | 6/10 | yes |
| Total | 618 | 140 | 102 | 17/21 | |
| SvEv | | | | | |
| D-E7 | 302 | 71 | 40 | 8/10 | yes |
| E-14 | | | | | |
| B-E2 | 64 | 17 | 14 | 8/10 | yes |
| Grand Total | 984 | 228 | 156 | 33/41 | |

Figure 3:
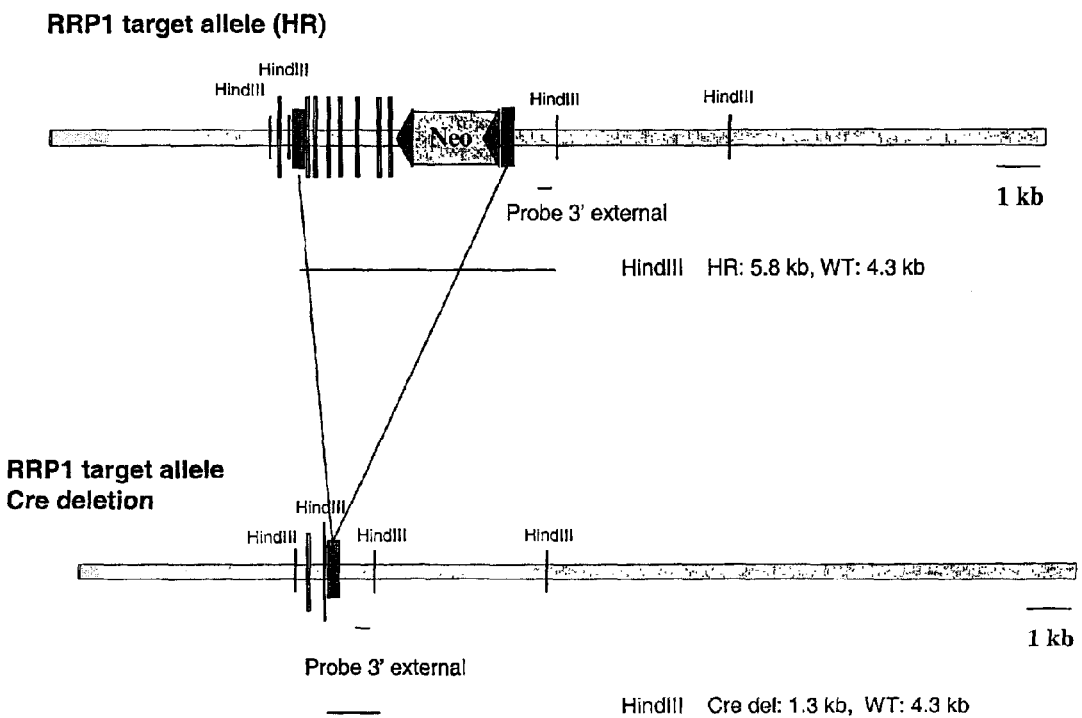
FIG. 3 depicts the target allele after HR and after Cre induced deletion. The expected sizes of the genomic fragments after digestion with restriction enzymes and Southern hybridization are indicated for the target allele in each of the following states: WT, HR, and Cre deleted.

Heterozygous Animals by In Vivo Deletion.
Target Allele with Cre Directed Deletion An in vivo deletion approach was pursued to generate C57BL/6 mice carrying the target alleles with Cre-directed deletion from mRRP1. Using this approach, the Cre transgene directs the removal of the sequences flanked by the LoxP sites, and thus, creates an RRP1 knockout in every cell of the animal (FIG. 3).

Heterozygote mice carrying the mRRP1 target allele (mRRP1$^{targ/+}$) from the B6-2 clones G-D5 and E-D9 (Table 2) were bred with transgenic C57BL/6-Cre-Deleter mice (Schwenk et al, NAR (95) Vol. 23, No 24, 5080–5081). This deleter mice have been crossed back to B6 for 10 generations, to establish the transgene on an congenic C57BL/6 background. This was done to maintain the C57BL/6 background after the in vivo deletion of the mRRP1 targeted allele. Resulting pups were genotyped on tail DNA for the presence of the target allele with Cre-directed deletion of mRRP1 by Southern Blot hybridization and by PCR for the presence of the Cre transgene.

Tail DNA was digested with HindIII and hybridized with the 3' external probe. In heterozygote animals the 5.8 kb band was reduced to a 1.3 kb band for the target allele. Alternatively animals were typed by PCR.

Target Allele with Flp-directed Deletion

An in vivo deletion approach was pursued, to generate C57BL/6 mice carrying the target allele with Flp directed deletion of the Neo marker from RRP1. In this case, the mRRP1 gene is still functional in every cell, but the animals may later be crossed with conditional Cre deleter mice for tissue specific or time-specific deletion of the sequences flanked by LoxP to create conditional mRRP1 knockout mice.

To avoid any potential hypomorphic effects, the Frt flanked Neo selection marker was removed in vivo by Flp recombination. Heterozygote mice carrying the mRRP1 target allele from the B6-2 clones G-D5 and E-D9 (Table 2) were bred with transgenic C57BL/6 mice heterozygous for the CAAGS-FLPe transgene (Rodriguez et al., (2000) Nat Genet 25:139–140). Resulting pups were genotyped on tail DNA for the presence of the target allele by Southern Blot hybridization and by PCR for the presence of the CAAGS-Flp transgene.

Tail DNA was digested with HindIII and hybridized the 3' external probe. In heterozygote animals the 4.3 kb target allele band was reduced to a 3.8 kb band after the removal of the Frt-flanked Neo marker (FIG. 4). Alternatively animals were typed by PCR.

Homozygous Animals
Target Allele with Cre Directed Deletion

To generate mice homozygous for the mRRP1 knockout allele on the C57BL/6 background, heterozygous animals derived from the in vivo deleted clones G-D5 and E-D9 were intercrossed. From this cross 17 litters were born, giving rise to 106 pups. 28 of these pups died pre-weaning. Two of these pups were recovered and genotyped by PCR as homozygous complete KO. 49 of the living animals were weaned and 14 animals were genotyped on tail DNA with the 3' external probe after digestion with HindIII. In homozygous animals the original 4.3 kb wild type band was reduced to a 1.3 kb band. Alternatively animals were typed by PCR.

From the 14 animals 3 typed as homozygous mutant, 7 typed as heterozygous mutant and 4 typed as wildtype. These numbers matched the expected Mendelian distribution. The homozygous animals appear to be normal. No gross difference was detected in comparison to their wild-type littermates.

To test for the fertility of the homozygous mutant animals and to increase further the colony, homozygous mutant animals for the mRRP1 derived from the in vivo deleted clones G-D5 were intercrossed. To date, 14 pups have been born from these intercrosses, and 4 have been weaned, demonstrating the fertility of the homozygous mRRP1 KO mice.

The homozygous mRRP1 KO mice and cells are used to analyze mRRP1 function in mammals. Data from Example VI show that overexpression of human RRP1 in HeLa cells results in enhanced phosphorylation of EGFR. Inactivation of mRRP1 gene function should therefore result in attenuated phosphorylation of EGFR and or MAPK in tissues obtained from mRRP1 KO mice.

Growth factors like EGF, PDGF cause proliferation in fibroblast cell culture. As *Drosophila* Rhomboid and mammalian RRPs are thought to release membrane-bound growth factors by cleavage, RRP function with regard to cell cycle progression and proliferation is analyzed with embryonic and adult fibroblasts isolated from mRRP1 KO mice.

Direct effects of RRP function on tumor development is analyzed by crossing mRRP1 KO mice with APCMin mice, a model for human colon cancer. As the mRRP1 KO strain and the APCmin (Moser A R et al., (1993) Proc Natl Acad Sci USA 90:8977–81) strain are both on C57BL/6 background, tumor formation can be analyzed on pure genetic backgrounds, and thus side effects resulting from mixed genetic backgrounds can be excluded. A strong reduction of small intestinal tumor formation in mRRP1 −/−, APCMin +/− mice versus APCMin +/− mice is expected, demonstrating that mRRP1 is a powerful target for anti-cancer drug development.

RRP is located at the cell surface and therefore a target for antibody therapy. As the extracellular loops of mouse and human RRP protein are strongly conserved, it is difficult to generate antibodies against human RRP in mice, as mice will recognize the human RRP as self. Therefore, RRP KO mice are used for the production of monoclonal antibodies directed against human RRP protein.

What is claimed is:

1. A method of screening for agents that modulates the interaction of Rhomboid Related Protein (RRP) polypeptide with an RRP binding target comprising:
   a) expressing a recombinant polypeptide,
   b) incubating the recombinant RRP polypeptide with an RRP binding target and a candidate RRP modulating agent, and
   c) determining whether said candidate RRP modulating agent modulates the binding of RRP polypeptide with the RRP binding target,
   wherein RRP is SEQ ID No: 2 (RRP1).

2. The method according to claim 1 wherein said binding target is selected from the group consisting of TGFα, EGF, and amphiregulin.

3. The method according to claim 1 wherein said binding target is TGFα.

4. The method according to claim 1 wherein said candidate RRP modulating agent is an antibody.

5. The method according to claim 1 wherein said candidate RRP modulating agent is a small organic molecule.

* * * * *